US011911619B2

(12) United States Patent
Chang

(10) Patent No.: US 11,911,619 B2
(45) Date of Patent: Feb. 27, 2024

(54) METHOD OF NEURAL INTERVENTION FOR THE TREATMENT OF AFFECTIVE NEUROPSYCHIATRIC DISORDERS

(71) Applicant: The Regents of the University of California, Oakland, CA (US)

(72) Inventor: Edward F. Chang, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 85 days.

(21) Appl. No.: 16/498,282

(22) PCT Filed: Apr. 6, 2018

(86) PCT No.: PCT/US2018/026612
§ 371 (c)(1),
(2) Date: Sep. 26, 2019

(87) PCT Pub. No.: WO2018/187785
PCT Pub. Date: Oct. 11, 2018

(65) Prior Publication Data
US 2020/0038657 A1 Feb. 6, 2020

Related U.S. Application Data

(60) Provisional application No. 62/483,046, filed on Apr. 7, 2017.

(51) Int. Cl.
*A61N 1/36* (2006.01)
*A61N 1/05* (2006.01)

(52) U.S. Cl.
CPC ....... *A61N 1/36025* (2013.01); *A61N 1/0531* (2013.01); *A61N 1/0534* (2013.01); *A61N 1/36021* (2013.01)

(58) Field of Classification Search
CPC ............. A61N 1/36025; A61N 1/0531; A61N 1/0534; A61N 1/36021; A61N 1/36096; A61N 1/36135; A61N 1/36031
(Continued)

(56) References Cited

U.S. PATENT DOCUMENTS 8,190,264 B2 5/2012 Lozano et al.
2006/0212090 A1 9/2006 Lozano et al.
(Continued)

FOREIGN PATENT DOCUMENTS

WO 2016/023126 A1 2/2016

OTHER PUBLICATIONS

Berman et al. (2008) "Probabilistic streamline q-ball tractography using the residual bootstrap" Neuroimage 39: 215-222.
(Continued)

*Primary Examiner* — Amanda K Hulbert
*Assistant Examiner* — Philip C Edwards
(74) *Attorney, Agent, or Firm* — Edward J. Baba; Michael J. Blessent; Bozicevic, Field & Francis LLP

(57) ABSTRACT

The present disclosure provides a method and system for treating affective disorders such as depression and/or anxiety and/or related disorders through neuromodulatory intervention that includes brain targets within the orbitofrontal cortex (OFC). This method includes the application of electrical stimulation through an electrical signal generator device where the distal end of the device comprises at least one stimulating electrode in contact with the OFC. The treatment system includes patient selection, implantation of at least one stimulating electrode in contact with the OFC, acute or chronic electrical stimulation of the OFC, and evaluation of the effects of stimulation on clinical symptoms and status.

30 Claims, 36 Drawing Sheets

(58) Field of Classification Search
USPC .......................................................... 607/45
See application file for complete search history.

(56) References Cited

U.S. PATENT DOCUMENTS

| | | | |
|---|---|---|---|
| 2007/0027500 A1 | 2/2007 | Maschino et al. | |
| 2010/0057159 A1* | 3/2010 | Lozano | A61N 1/36096 607/45 |
| 2011/0184486 A1* | 7/2011 | De Ridder | A61N 1/0529 607/45 |
| 2013/0178913 A1 | 7/2013 | Lozano | |
| 2014/0148872 A1* | 5/2014 | Goldwasser | A61N 1/36082 607/45 |
| 2014/0357932 A1* | 12/2014 | Lozano | A61N 1/36085 600/9 |
| 2016/0008620 A1 | 1/2016 | Stubbeman | |
| 2016/0220821 A1* | 8/2016 | O'Connell | A61N 1/36064 |

OTHER PUBLICATIONS

Choi et al. (2015) "Mapping the 'Depression Switch' During Intraoperative Testing of Subcallosal Cingulate Deep Brain Stimulation" JAMA Neurol 72(11): 1252-1260.
Drysdale et al. (2017) "Resting-state connectivity biomarkers define neurophysiological subtypes of depression" Nat Med 23: 28-38.
Dunlop et al. (2017) "Functional Connectivity of the Subcallosal Cingulate Cortex And Differential Outcomes to Treatment With Cognitive-Behavioral Therapy or Antidepressant Medication for Major Depressive Disorder" Am J Psychiatry 174(6): 533-545.
Dunlop et al. (2017) "Effects of Patient Preferences on Outcomes in the Predictors of Remission in Depression to Individual and Combined Treatments (PReDICT) Study" Am J Psychiatry 174(6): 546-556.
Fettes et al. (2017) "Cortico-Striatal-Thalamic Loop Circuits of the Orbitofrontal Cortex: Promising Therapeutic Targets in Psychiatric Illness" Front Syst Neurosci 11(25): 1-23.
Formaggio et al. (2013) "Frequency and time-frequency analysis of intraoperative ECoG during awake brain stimulation" Front Neuroeng 6(1): 1-8.
Guillory et al. (2014) "Exploring emotions using invasive methods: review of 60 years of human intracranial electrophysiology" Soc Cogn Affect Neurosci 9: 1880-1889.
Heffer et al. (2008) "A Novel Stimulus Artifact Removal Technique for High-Rate Electrical Stimulation" J Neurosci Methods 170(2): 277-284.
Hoffmann et al. (2011) "Detection and removal of stimulation artifacts in electroencephalogram recordings" 2011 Annual International Conference of the IEEE Engineering in Medicine and Biology Society, pp. 7159-7162. IEEE.
Johansen-Berg et al. (2008) "Anatomical Connectivity of the Subgenual Cingulate Region Targeted with Deep Brain Stimulation for Treatment-Resistant Depression" Cereb Cortex 18(6): 1374-1383.
Kohl et al. (2014) "Deep brain stimulation for treatment-refractory obsessive compulsive disorder: a systematic review" BMC Psychiatry 14: 214 (10 pages).
Kringelbach et al. (2004) "The functional neuroanatomy of the human orbitofrontal cortex: evidence from neuroimaging and neuropsychology" Progress in Neurobiology 72(5): 341-372.
Mayberg et al. (2005) "Deep Brain Stimulation for Treatment-Resistant Depression" Neuron 45(5): 651-660.
Riva-Posse et al. (2014) "Defining Critical White Matter Pathways Mediating Successful Subcallosal Cingulate Deep Brain Stimulation for Treatment-Resistant Depression" Biol Psychiatry 76(12): 963-969.
Riva-Posse et al. (2017) "A connectomic approach for subcallosal cingulate deep brain stimulation surgery: prospective targeting in treatment-resistant depression" Mol Psychiatry 23: 843-849.
Rudebeck et al. (2011) "Balkanizing the primate orbitofrontal cortex: Distinct subregions for comparing and contrasting values" Ann NY Acad Sci 1239: 1-13.
Rudebeck et al. (2014) "The Orbitofrontal Oracle: Cortical Mechanisms for the Prediction and Evaluation of Specific Behavioral Outcomes" Neuron 84(6): 1143-1156.
Scangos et al. (2017) "Acute Frequency-Dependent Hypomania Induced by Ventral Subthalamic Nucleus Deep Brain Stimulation in Parkinson's Disease: A Case Report" Biol Psychiatry 82(5): e39-e41.
Sun et al. (2014) "A novel method for removal of deep brain stimulation artifact from electroencephalography" J Neurosci Methods 237: 33-40.
Valentin et al. (2005) "Single pulse electrical stimulation for identification of structural abnormalities and prediction of seizure outcome after epilepsy surgery: a prospective study" Lancet Neurol 4(11): 718-726.
Valentin et al. (2005) "Single-pulse electrical stimulation identifies epileptogenic frontal cortex in the human brain" Neurology 65(3): 426-435.
Veniero et al. (2010) "Potentiation of Short-Latency Cortical Responses by High-Frequency Repetitive Transcranial Magnetic Stimulation" J Neurophysiol 104: 1578-1588.

* cited by examiner

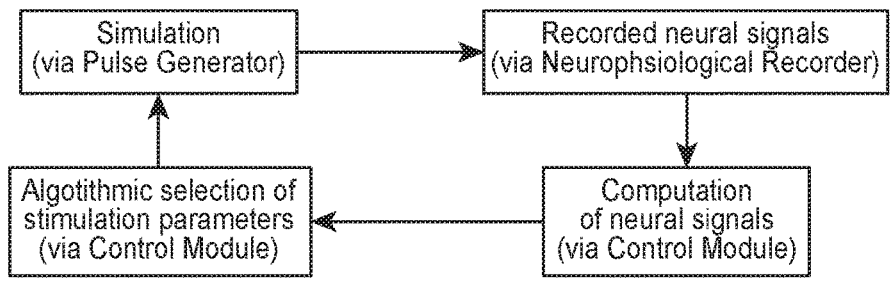
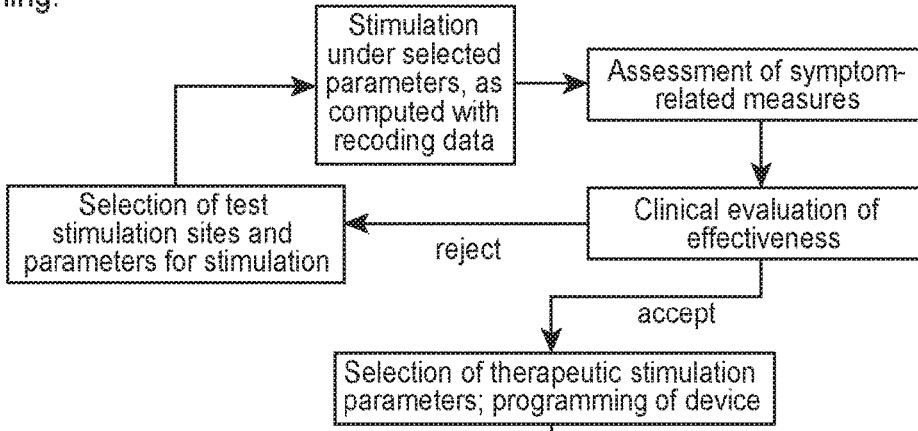
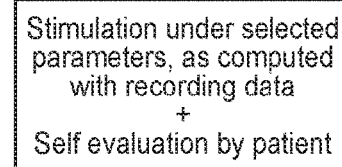
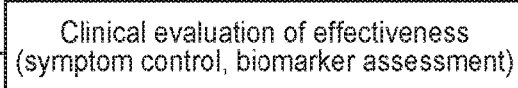
FIG. 10 (Cont.)

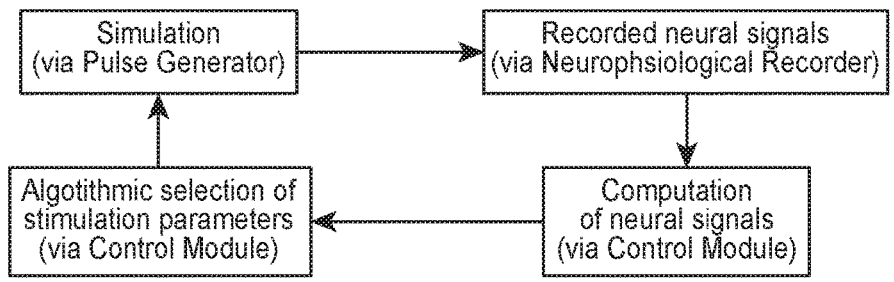
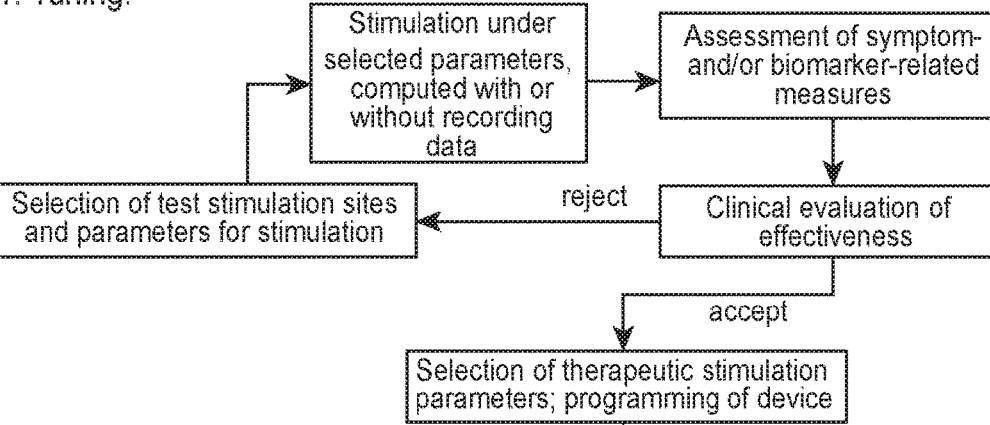
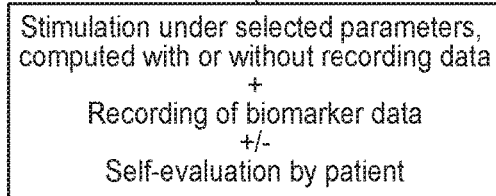
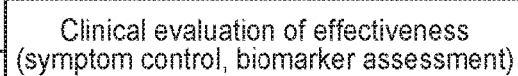
FIG. 12 (Cont.)

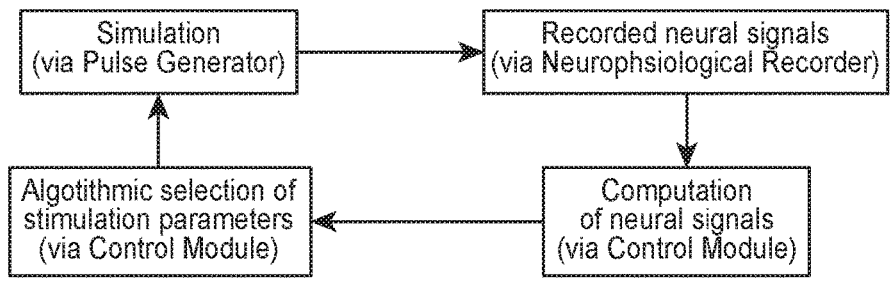
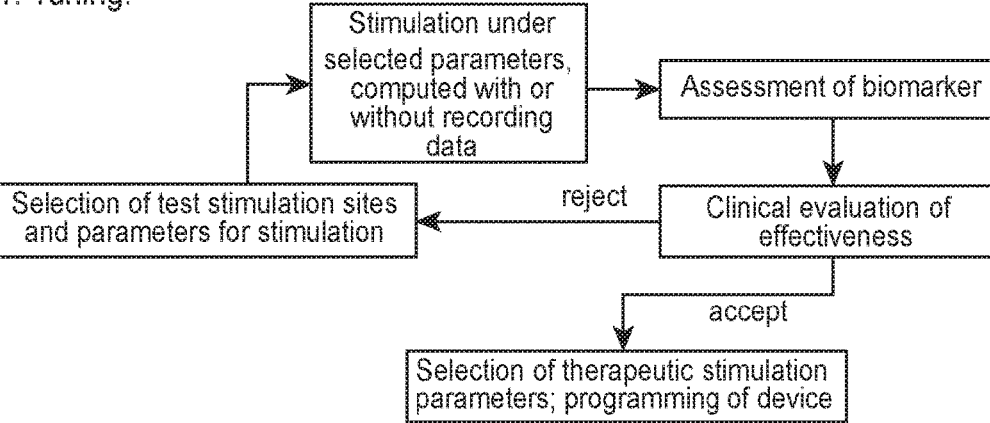
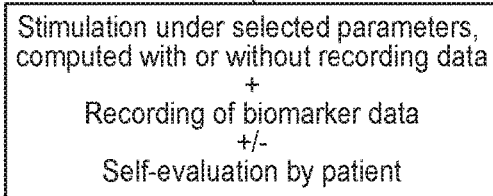
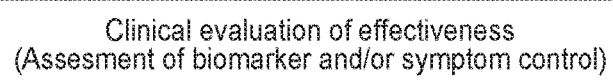
FIG. 13 (Cont.)

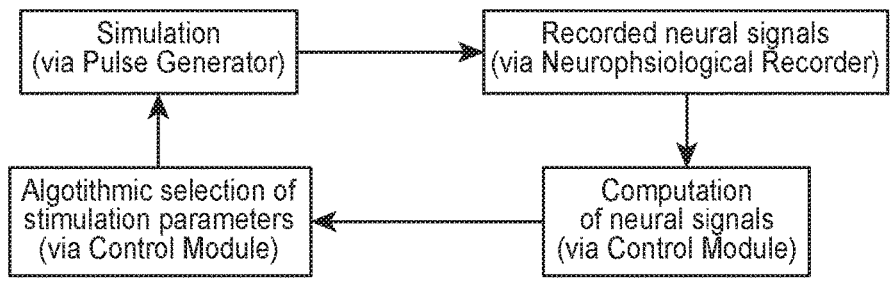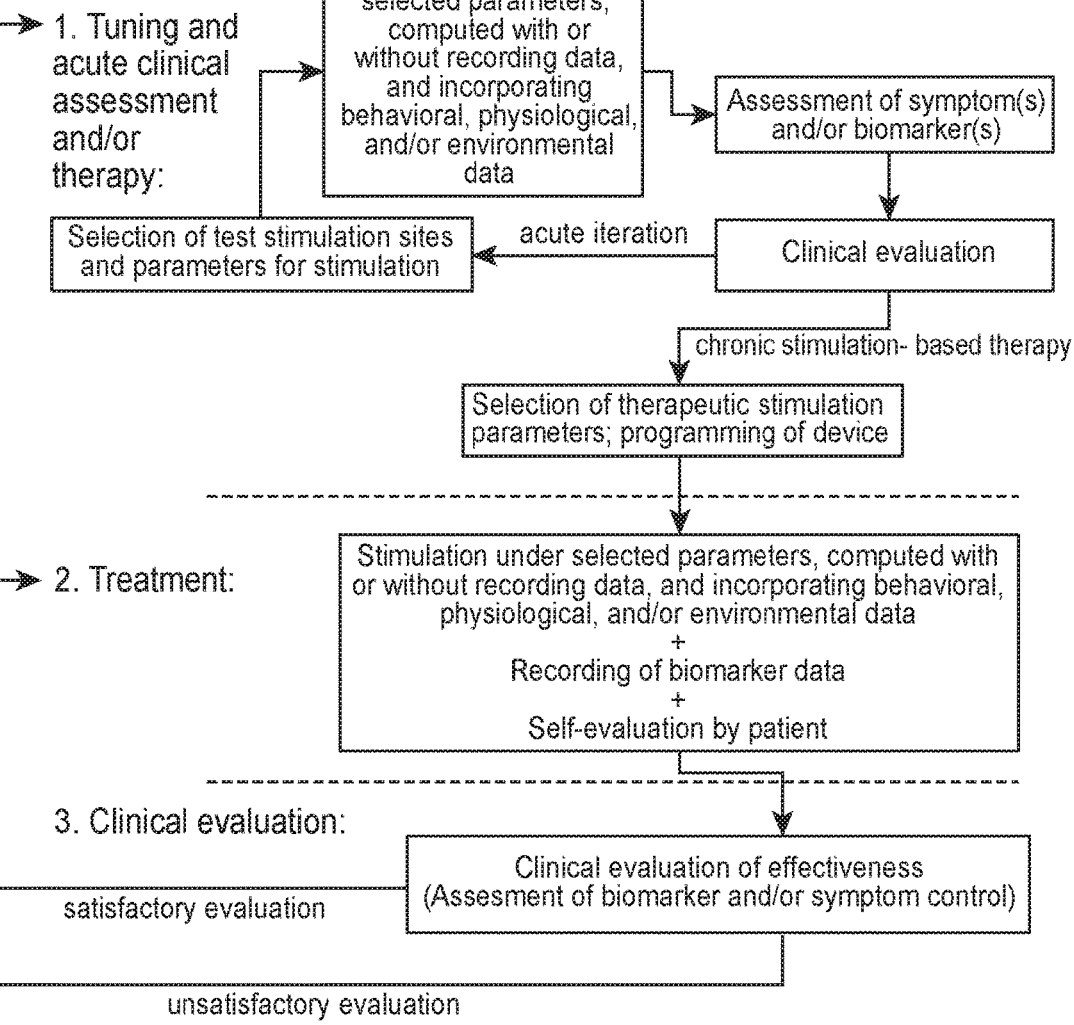
FIG. 14 (Cont.)

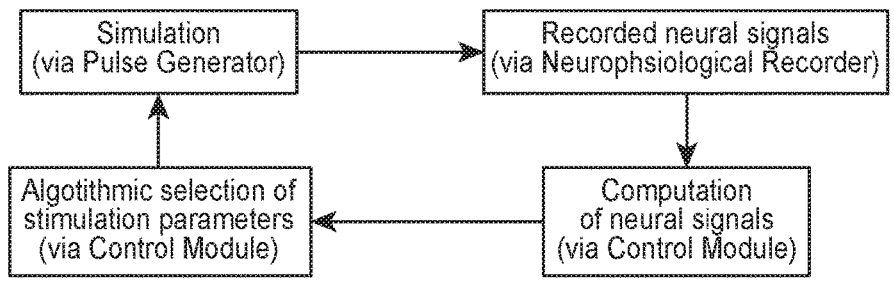
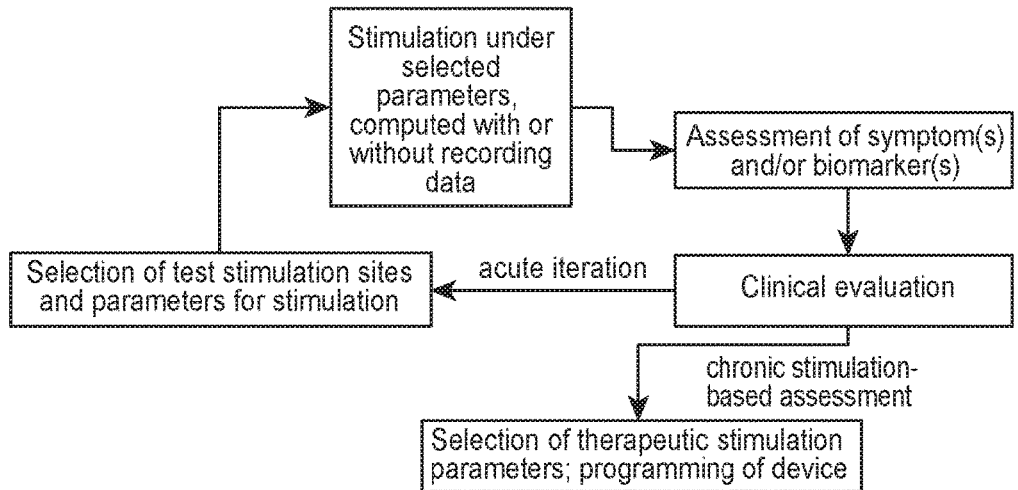
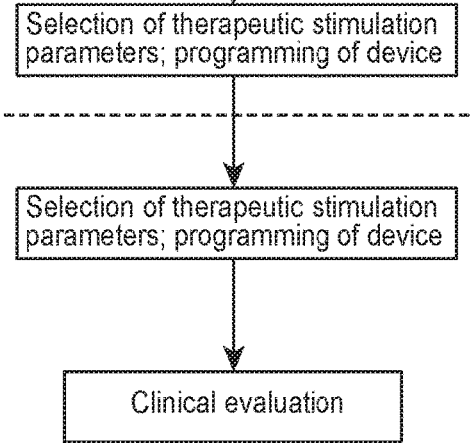
FIG. 15 (Cont.)

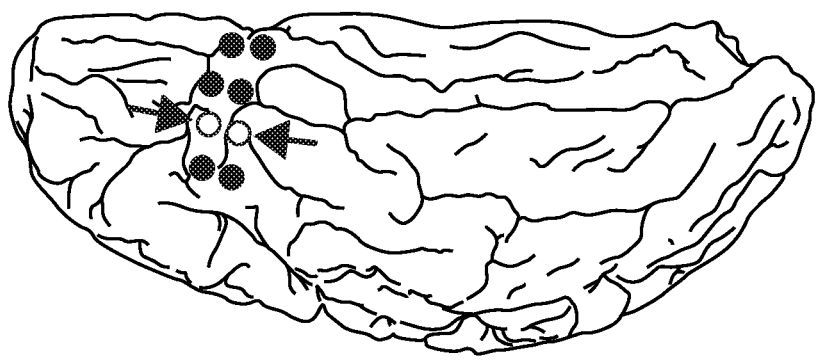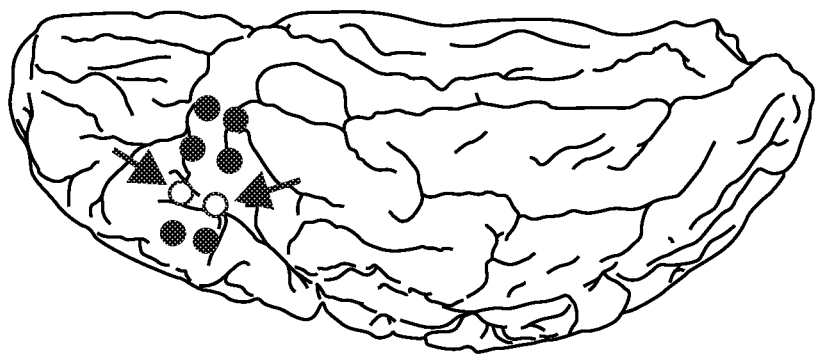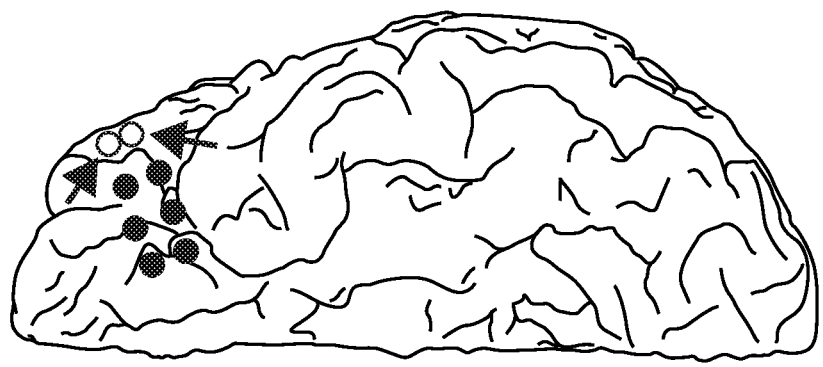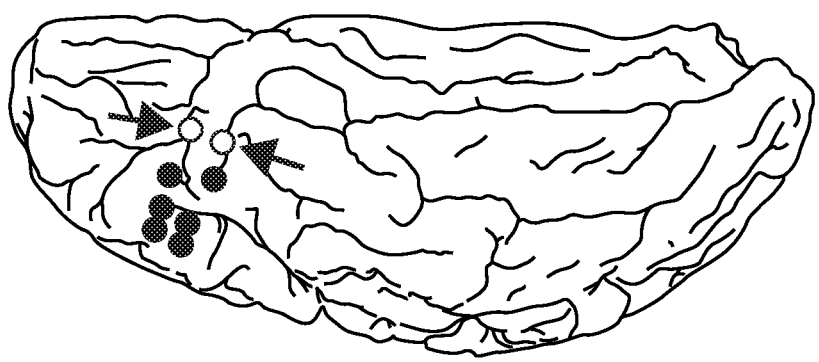
FIG. 19

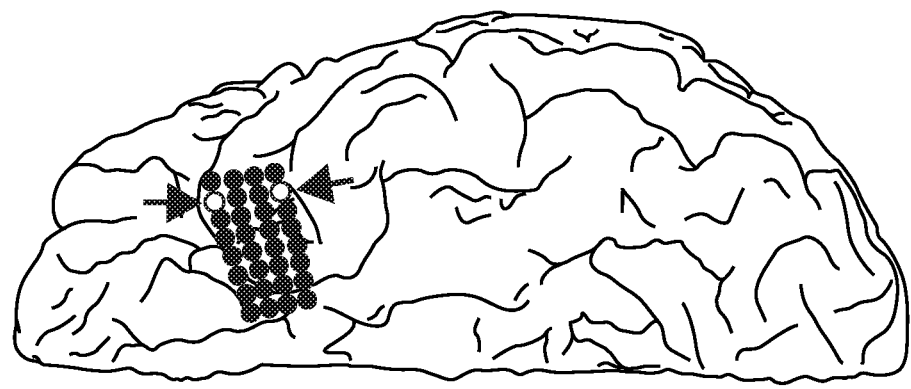
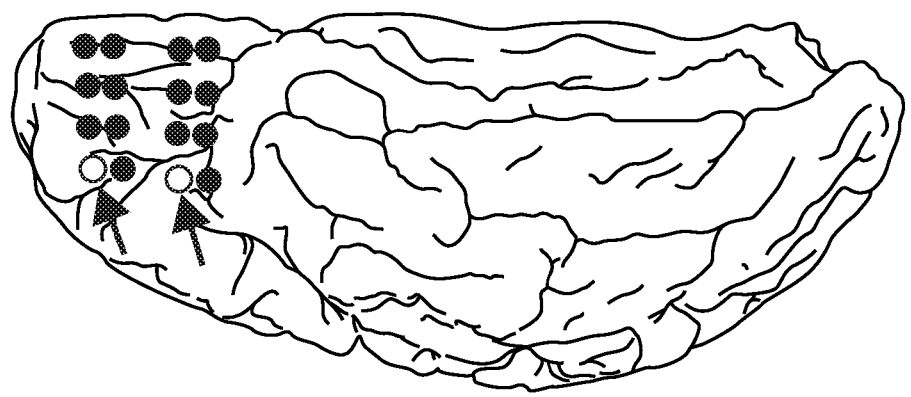
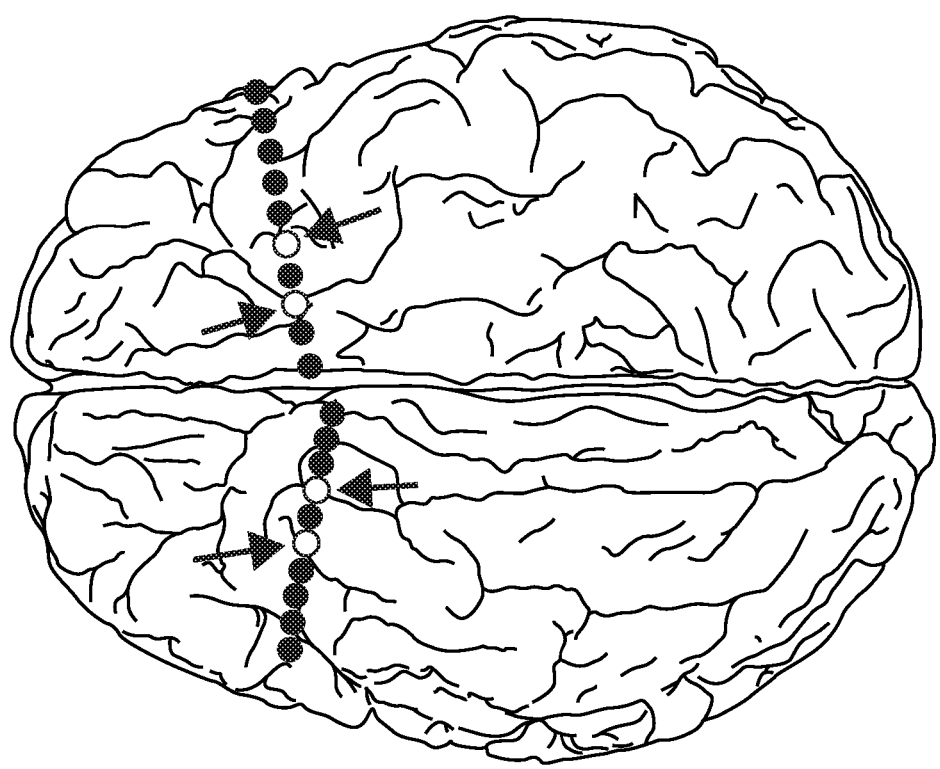
FIG. 19 (Cont.)

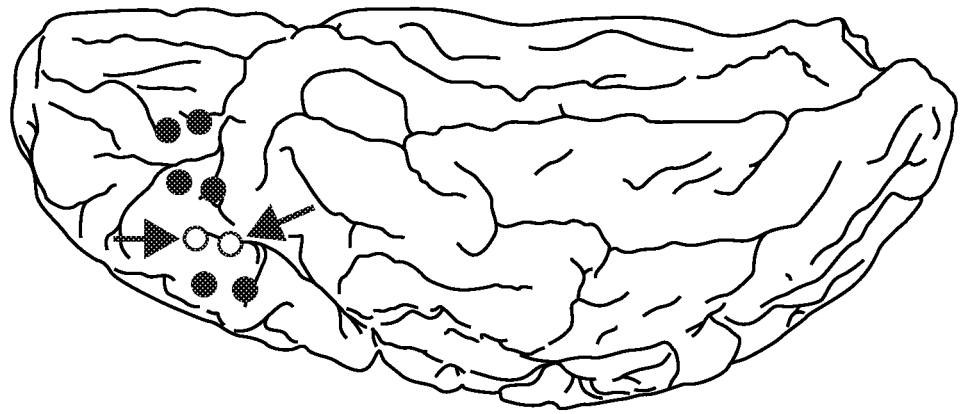
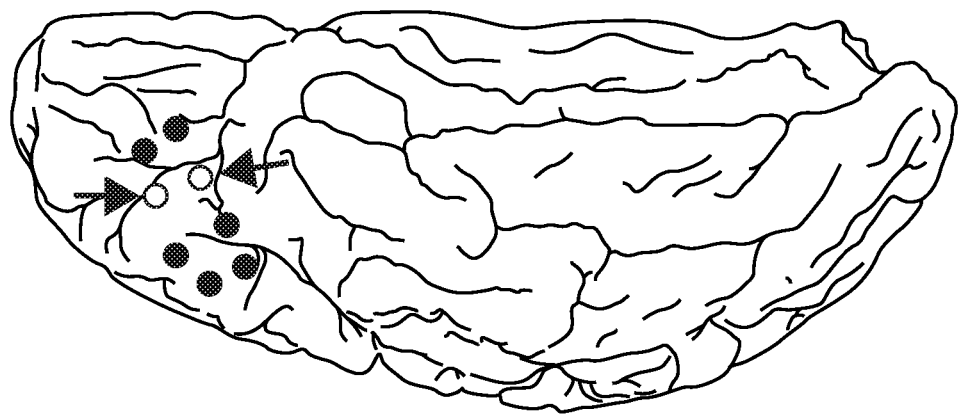
FIG. 20

| Region | No. Trials | Stimulation Current | Stimulation Frequency | Stimulation pulse width | Stimulation Duration |
|---|---|---|---|---|---|
| OFC | 54 | 2-10 mA | 10-100 Hz | 100-500 μsec | 1-10 sec |
| Dorsal ACC | 61 | 2-10 mA | 10-100 Hz | 100 μsec | 1-10 sec |
| Ventral ACC | 81 | 2-10 mA | 10-100 Hz | 100-500 μsec | 1-10 sec |
| Insula | 84* | 2-10 mA | 10-100 Hz | 100-500 μsec | 1-10 sec |
| Amygdala | 14 | 3 mA | 10-100 Hz | 100 μsec | 1-2 sec |
| Hippocampus | 41 | 2-10 mA | 10-100 Hz | 100-900 μsec | 1-3 sec |
| Total Trials | 335 | | | | |

*Mild anxiety was reported in one trial

FIG. 21

| Patient | Sites | | | Laterality |
|---|---|---|---|---|
| EC81 | Sham | OFC 50 Hz* | OFC 100 Hz | RIGHT |
| | | | Sham | |
| EC82 | Sham | Medial OFC | Lateral OFC | LEFT |
| | | | Sham | |
| EC84 | Sham | Lateral OFC | Medial OFC | RIGHT |
| | | | Sham | |
| EC87 | Sham | Lateral OFC | vACC | dACC | RIGHT |
| | | | Sham | |
| EC91 | Sham | Posterior Cingulate | Lateral OFC | RIGHT |
| | | | Sham | |
| EC92 | Sham | Lateral OFC | | LEFT |
| | | | Sham | |
| EC96 | Sham | Lateral OFC | | RIGHT |
| | | | Sham | |
| EC99 | Sham | Right Lateral OFC | Left Lateral OFC | BILATERAL |
| | | | Sham | |
| EC105 | Sham | Lateral OFC | Medial OFC | Cingulate | Amygdala | RIGHT |
| | | | Sham | |
| EC108 | Sham | | Lateral OFC | LEFT |

*Stimulation for all subsequent patients performed 100Hz

FIG. 22

| Patient | Mood report |
|---|---|
| EC81 | Decreased anxiety and "calmer" mood; abrupt improvement in manually scored mood |
| EC82 | Patient reported feeling more alive, more energy |
| EC84 | Patient improved from feeling "on the sad side" to "calm, cool and collected" |
| EC87 | Patient reported feeling "calm" and experiencing stronger positive feelings |
| EC91 | Patient's IMS scores remained high throughout the experiment (sham and OFC stimulation) |
| EC92 | Patient reported feeling calm and happy throughout the experiment (sham and OFC stimulation) |
| EC96 | Started out feeling "calm and peaceful", experienced no change |
| EC99 | Patient reported feeling less worried, reported the change during OFC stimulation and said it remained through left OFC stimulation and to the end of the experiment |
| EC105 | Patient reported feeling "less worried", "happier", and "joy" during OFC stimulation. Effect was tested at 1,3, and 6 mA and mood was seen to improve with increasing current |
| EC108 | Patient reported feeling "less emotional" and "pretty calm" during the OFC stimulation compared to baseline "easily annoyed" and "a little bit nervous" |

FIG. 23

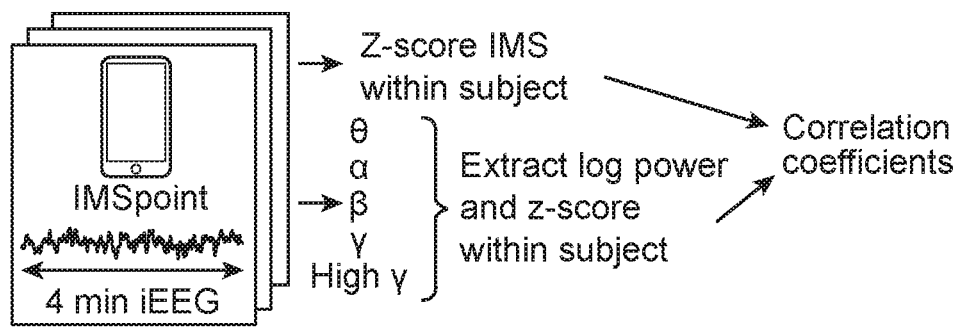
FIG. 26A
Group-Level:
Min-Mild Subjects
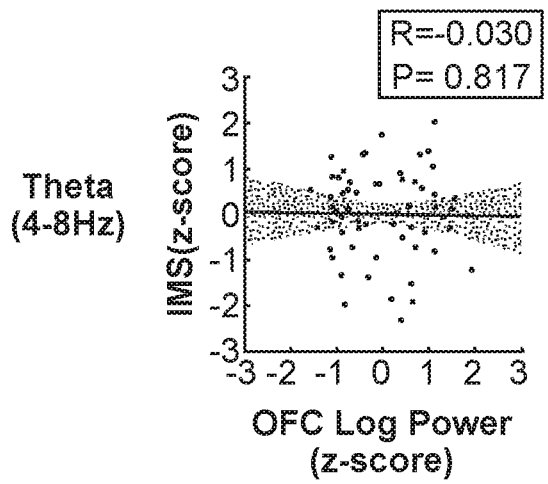
Group-Level:
Mod-Severe Subjects
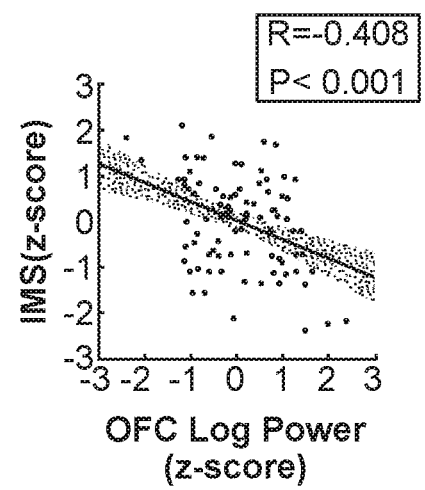
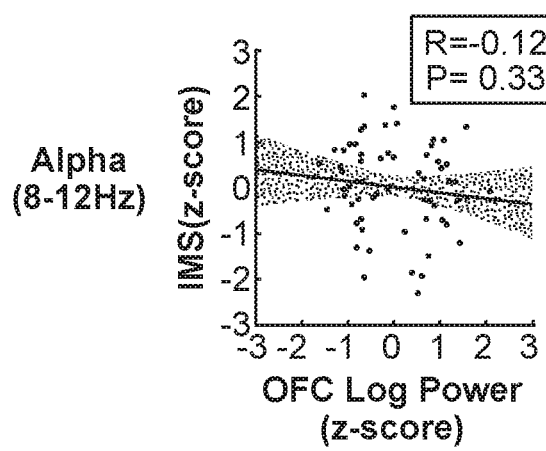
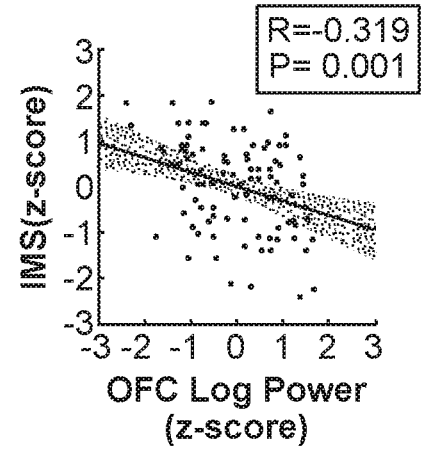
FIG. 26B          FIG. 26C

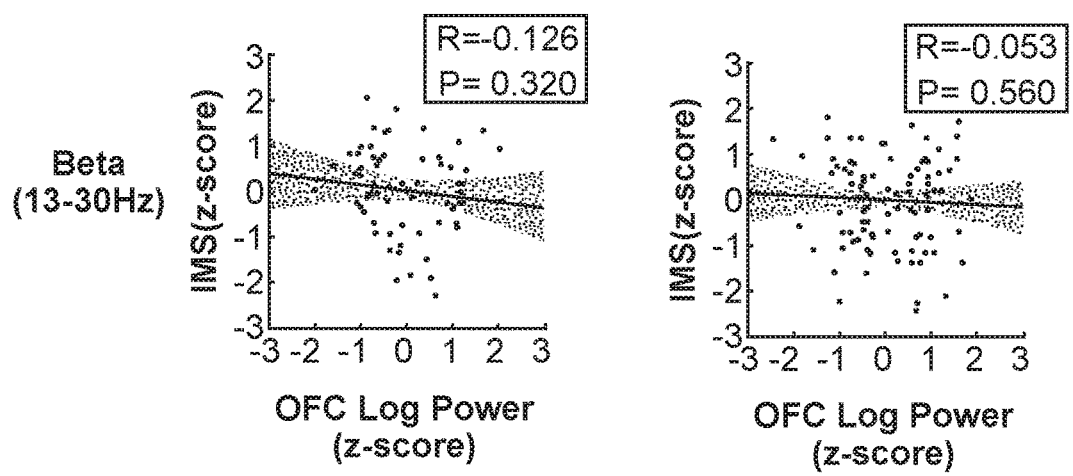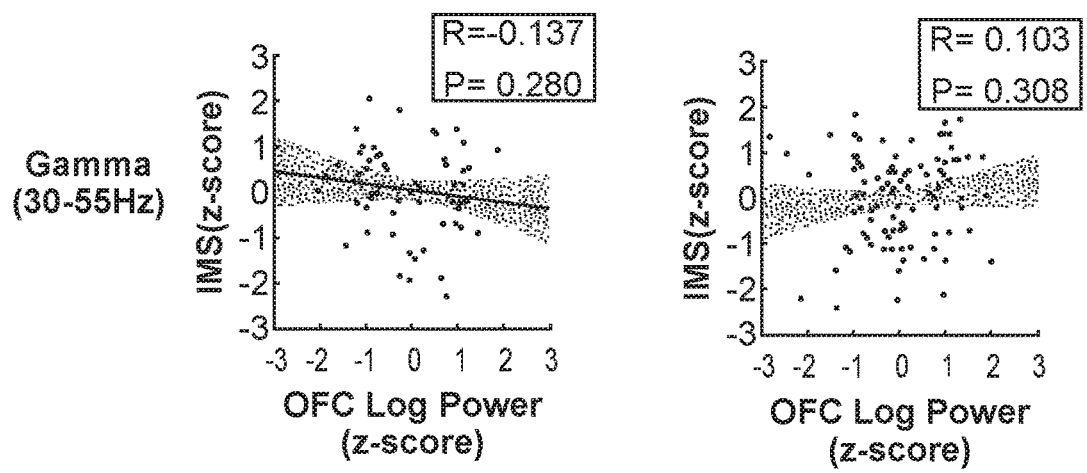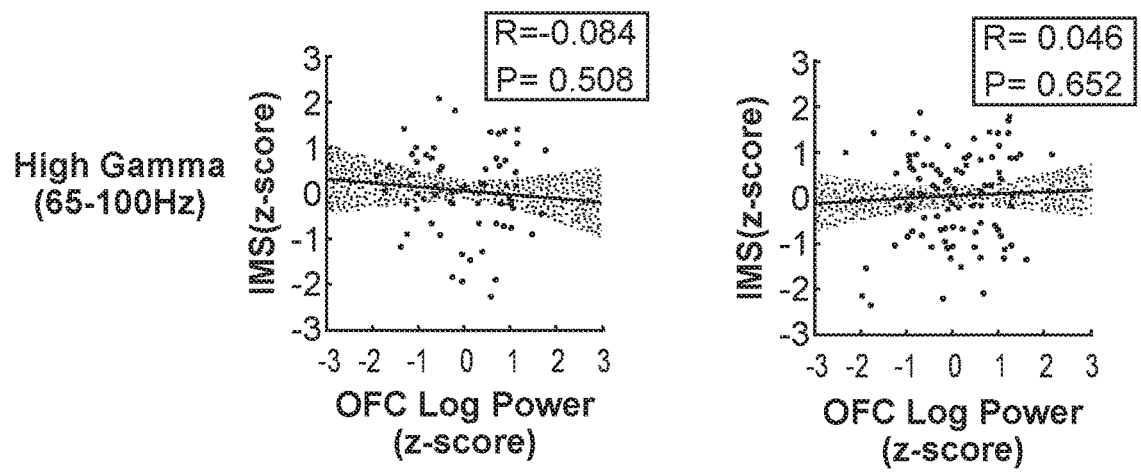
FIG. 26B (Cont.)　　FIG. 26C (Cont.)

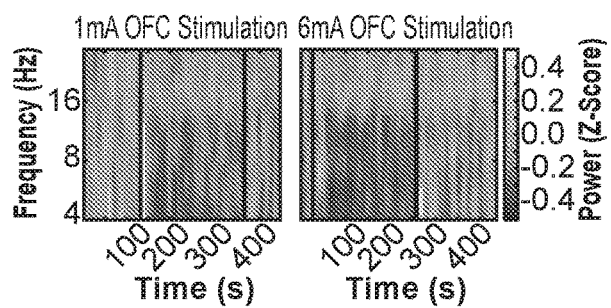
FIG. 27A
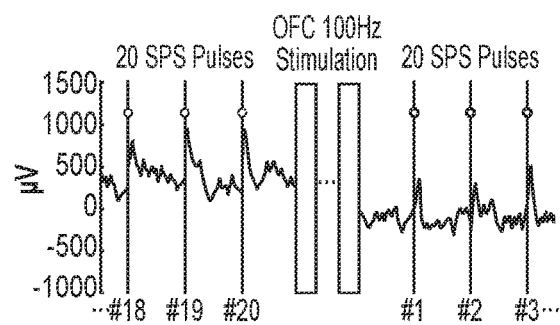
FIG. 27C
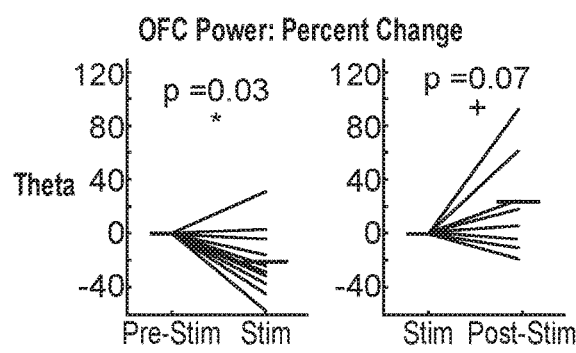
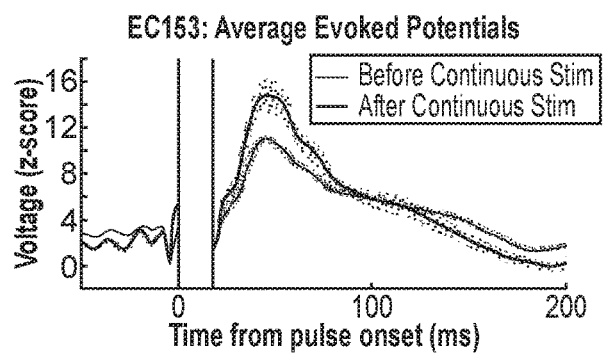
FIG. 27D
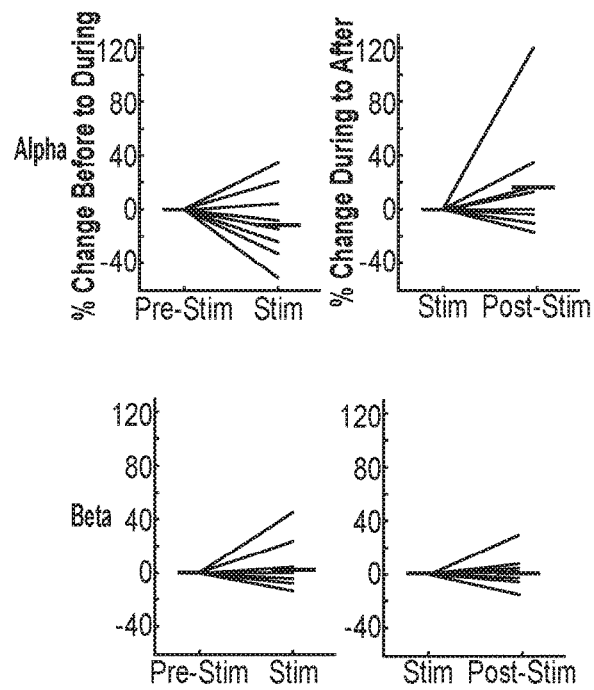
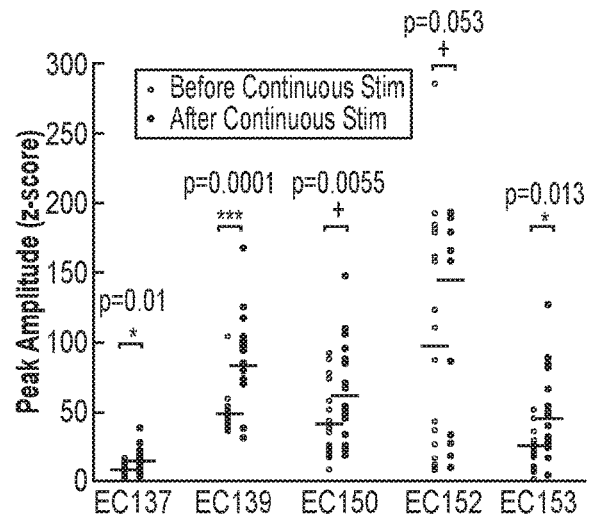
FIG. 27E
FIG. 27B

METHOD OF NEURAL INTERVENTION FOR THE TREATMENT OF AFFECTIVE NEUROPSYCHIATRIC DISORDERS

STATEMENT REGARDING FEDERALLY SPONSORED RESEARCH

This invention was made with government support under grant no. W911NF-14-2-0043 awarded by the Defense Advanced Research Projects Agency. The government has certain rights in the invention.

INTRODUCTION

The development of novel effective treatments for neuropsychiatric disorders is a leading goal of $21^{st}$-century medicine. Millions of individuals worldwide suffer from Major Depressive Disorder (MDD), Generalized Anxiety Disorder (GAD), Post-Traumatic Stress Disorder (PTSD), Addiction, Anorexia, Obsessive-Compulsive Disorder (OCD), Bipolar Disorder (BD), Chronic Pain, and related conditions. Vast numbers of patients remain ineffectively treated. Accordingly, neuropsychiatric disorders constitute the largest worldwide disease burden of all clinical categories, accounting for 22.7% of all years lived with disability.

Established treatment modalities—including pharmacological treatment, cognitive behavioral therapy (CBT), surgical lesioning and electroconvulsive therapy (ECT)—provide lasting benefits to a proportion of individuals but prove inadequate for many. For example, it is estimated that in the case of MDD, ~40-50% of adult patients undergoing treatment with selective serotonin reuptake inhibitors fail to respond. While CBT has shown some effectiveness, for example in preventing MDD relapse following pharmacologic treatment, relapse rates remain significant (~35-50% in long-term studies). Surgical lesioning approaches for neuropsychiatric disorders are highly invasive and do not yield optimal outcomes (e.g., full response rates of <60% in the case of anterior capsulotomy for OCD). No fully reliable treatment method exists for any of the major affective disorders.

Gross-level electrophysiological intervention in the form of ECT has been long used for some neuropsychiatric disorders, but many severely affected patients experience no lasting relief with ECT and endure significant unwanted cognitive side-effects. Transcranial stimulation methods, while non-invasive, have not provided conclusive evidence regarding their effectiveness—findings are perhaps strongest for MDD, but in that case response rates in the short term are still typically <60%. More advanced methods involving targeted direct stimulation of specific subregions of the brain, such as subgenual cingulate, have provided promising early results in recent years but have failed in clinical trials owing to variability in patient response.

SUMMARY

Methods and systems for treatment of a neuropsychiatric disorder in a subject are provided. The methods and systems are used for treatment of affective disorders related to anxiety and/or depression and/or related disorders, such as, Major Depressive Disorder (MDD), Generalized Anxiety Disorder (GAD), Post-Traumatic Stress Disorder (PTSD), Addiction, Anorexia, Obsessive-Compulsive Disorder (OCD), and Bipolar Disorder (BD), and Chronic Pain.

The methods involve stimulation of the Brodmann Area 11 and/or Brodmann Area 47 of the orbitofrontal cortex (OFC) region of brain of the subject via an electrode in a manner effective to treat the neuropsychiatric disorder and/or alleviate a symptom of the neuropsychiatric disorder in the subject.

In certain aspects, a method for treating a neuropsychiatric disorder in a subject includes positioning an electrode at Brodmann Area 11 and/or Brodmann Area 47 of orbitofrontal cortex region of brain of the subject; and applying electrical stimulation to the Brodmann Area 11 and/or Brodmann Area 47 via the electrode in a manner effective to treat the neuropsychiatric disorder in the subject. Embodiments of the method include applying electrical stimulation to Brodmann Area 11, Brodmann Area 47, or Brodmann Area 11 and Brodmann Area 47. The electrode may be positioned on a surface of Brodmann Area 11 and/or Brodmann Area 47 or within Brodmann Area 11 and/or Brodmann Area 47. The electrode may be a non-brain penetrating surface electrode, a non-brain penetrating surface electrode array, a brain-penetrating electrode, or a brain-penetrating electrode array.

In certain cases, the neuropsychiatric disorder may be depression and applying the electrical stimulation treats depression. In certain cases, the neuropsychiatric disorder may be anxiety and applying the electrical stimulation treats anxiety. The neuropsychiatric disorder may be one or more of Major Depressive Disorder (MDD), Generalized Anxiety Disorder (GAD), Post-Traumatic Stress Disorder (PTSD), Addiction, Anorexia, Obsessive-Compulsive Disorder (OCD), Bipolar Disorder (BD) or Chronic Pain.

Aspects of the methods include applying the electrical stimulation unilaterally or bilaterally. In some embodiments, the electrical stimulation is applied at least two times, wherein the site to which the electrical stimulation is applied is alternated or otherwise spatially or temporally patterned.

The method may further include assessing effectiveness of the treatment in the subject.

Also provided is a method for ameliorating a symptom of a neuropsychiatric disorder in a subject. The method may include positioning an electrode at BA11 and/or BA47 of OFC region of brain of the subject; and applying electrical stimulation to the via the electrode in a manner effective to ameliorate the symptom of the neuropsychiatric disorder in the subject. Electrical stimulation may applied as summarized above.

The symptom may be depression and wherein applying the electrical stimulation ameliorates depression. In some cases, depression may be measured by Beck Depression Inventories (BDI) score and applying the electrical stimulation may be effective in reducing the BDI score.

In some cases, the symptom may be anxiety and wherein applying the electrical stimulation ameliorates anxiety. In some cases, anxiety may be measured by Beck Anxiety Inventories (BAI) score and applying the electrical stimulation may be effective in reducing the BAI score.

In some cases, the symptom may be chronic-pain-related distress and wherein applying the electrical stimulation ameliorates chronic-pain-related distress. In some cases, chronic-pain-related distress may be measured by a Visual Analog Scale and applying the electrical stimulation may be effective in reducing the Visual Analog Scale score.

In some aspects, the treating of a neuropsychiatric disorder in a subject may result in OFC activity similar to that found in subjects without the neuropsychiatric disorder. In certain cases, a subject without a neuropsychiatric disorder may not have increased low frequency power detectable from the OFC while a subject with a neuropsychiatric disorder may have increased low frequency power in the OFC. In certain aspects, the methods and systems described herein may suppress the low frequency power in the OFC, thereby treating or ameliorating the neuropsychiatric disorder. In certain cases, a neuropsychiatric disorder treatable by suppressing low frequency power in the OFC by electrically stimulating the OFC (e.g., lateral OFC (e.g., BA11 and/or 47) or medial OFC) may be depression and/or anxiety.

A closed-loop method for treating a neuropsychiatric disorder in a subject is also provided. The method may include: i. positioning a stimulation electrode at Brodmann Area 11 and/or Brodmann Area 47 of orbitofrontal cortex (OFC) region of brain of the subject; ii. positioning a measurement electrode at a secondary area of the brain of the subject, which secondary area may be within the OFC region, including the Broadmann 11 and/or 47, or another area, such as, amygdala, hippocampus, cingulate, frontal pole, or lateral frontal lobe; iii. applying electrical stimulation to the Brodmann Area 11 and/or Brodmann Area 47 via the stimulation electrode in a manner effective to treat the neuropsychiatric disorder; iv. receiving an electrical signal from the secondary area of the brain of the subject; v. applying electrical signal metrics to a control algorithm that is tuned to a clinically relevant target (e.g., a range of signal indicative of effective treatment); vi. modulating one or more programmed stimulation parameters according to the algorithm's control law; and vii. applying the modulated electrical stimulation to the Brodmann Area 11 and/or Brodmann Area 47 via the stimulation electrode in a manner effective to treat the neuropsychiatric disorder. In certain cases, the secondary area of the brain may be amygdala and/or hippocampus.

The stimulation electrode may be a brain-penetrating electrode or a non-brain penetrating electrode. The measurement electrode may be a brain-penetrating electrode or a non-brain penetrating electrode. Electrical stimulation may applied as summarized above.

A closed-loop method for ameliorating a symptom of a neuropsychiatric disorder in a subject is also disclosed. The method may include i. positioning a stimulation electrode at Brodmann Area 11 and/or Brodmann Area 47 of orbitofrontal cortex region of brain of the subject; ii. positioning a measurement electrode at a secondary area of the brain of the subject; iii. applying electrical stimulation to the Brodmann Area 11 and/or Brodmann Area 47 via the stimulation electrode in a manner effective to ameliorate the symptom of the neuropsychiatric disorder; iv. receiving an electrical signal from the secondary area of the brain of the subject via the measurement electrode, which secondary area may be within the OFC region, including the Broadmann 11 and/or 47, or another area such as, amygdala, hippocampus, cingulate, frontal pole, or lateral frontal lobe; v. applying electrical signal metrics to a control algorithm that is tuned to a clinically relevant target (e.g., a range of signal indicative of effective treatment); vi. modulating one or more programmed stimulation parameters according to the algorithm's control law; and vii. applying the modulated electrical stimulation to the Brodmann Area 11 and/or Brodmann Area 47 via the stimulation electrode in a manner effective to ameliorate the symptom of the neuropsychiatric disorder. The secondary area of the brain may be amygdala and/or hippocampus.

A system for treating a neuropsychiatric disorder in a subject is also disclosed. The system includes a stimulation electrode adapted for positioning at Brodmann Area 11 and/or Brodmann Area 47 in orbitofrontal cortex region of brain of the subject; and a processor programmed to instruct the stimulation electrode to apply an electrical stimulation to the Brodmann Area 11 and/or Brodmann Area 47 in a manner effective to treat the neuropsychiatric disorder in the subject. The system may further include a user interface comprising an input electronically coupled to the processor for instructing the stimulation electrode to apply an electrical stimulation to the Brodmann Area 11 and/or Brodmann Area 47 to treat the neuropsychiatric disorder in the subject. The user interface may be password protected and may be operable by a health care practitioner. A system for ameliorating a symptom of a neuropsychiatric disorder in a subject may be used for applying the electrical stimulation in a manner effective to ameliorate the symptom of the neuropsychiatric disorder in the subject.

A closed-loop system for treating a neuropsychiatric disorder in a subject may include a stimulation electrode adapted for positioning at Brodmann Area 11 and/or Brodmann Area 47 in orbitofrontal cortex region of brain of the subject; a measurement electrode adapted for positioning at a secondary area of the brain and for recording an electrical signal from the secondary area after an electrical stimulation is applied to the Brodmann Area 11 and/or Brodmann Area 47; a processor programmed to instruct the stimulation electrode to apply an electrical stimulation to the Brodmann Area 11 and/or Brodmann Area 47 in a manner effective to treat the neuropsychiatric disorder in the subject; receive the electrical signal from the secondary area of the brain of the subject via the measurement electrode, which secondary area may be within the OFC region, including the Broadmann 11 and/or 47, or another area such as, amygdala, hippocampus, cingulate, frontal pole, or lateral frontal lobe; apply electrical signal metrics to a control algorithm that is tuned to a clinically relevant target (e.g., a range of signal indicative of effective treatment); modulate one or more programmed stimulation parameters according to the algorithm's control law; and apply the modulated electrical stimulation to the Brodmann Area 11 and/or Brodmann Area 47 via the stimulation electrode in a manner effective to treat the neuropsychiatric disorder.

A closed loop system may be configured for ameliorating a symptom of a neuropsychiatric disorder in a subject. The system may include a stimulation electrode adapted for positioning at Brodmann Area 11 and/or Brodmann Area 47 in orbitofrontal cortex region of brain of the subject; a measurement electrode adapted for positioning at a secondary area of the brain and for recording an electrical signal from the secondary area after an electrical stimulation is applied to the Brodmann Area 11 and/or Brodmann Area 47; a processor programmed to: instruct the stimulation electrode to apply an electrical stimulation to the Brodmann Area 11 and/or Brodmann Area 47 in a manner effective to ameliorate the symptom of the neuropsychiatric disorder in the subject; receive the electrical signal from the secondary area of the brain of the subject via the measurement electrode, which secondary area may be within the OFC region, including the Broadmann 11 and/or 47, or another area such as, amygdala, hippocampus, cingulate, frontal pole, or lateral frontal lobe; apply electrical signal metrics to a control algorithm that is tuned to a clinically relevant target (e.g., a range of signal indicative of effective treatment); modulate one or more programmed stimulation parameters according to the algorithm's control law; and apply the modulated electrical stimulation to the Brodmann Area 11 and/or Brodmann Area 47 via the stimulation electrode in a manner effective to ameliorate the symptom of the neuropsychiatric disorder.

In certain aspects, an electrical signal measured from brain to determine a symptom of a neuropsychiatric disorder in a subject may be intracranial electroencephalography (iEEG) or a similar technique. In some cases, electrical signal may be measured continuously, intermittently, or both. For continuous measurement, electroencephalography may be performed for an uninterrupted period of 10 sec-24 hrs or more, e.g., 30 sec-18 hrs, 1 min-12 hrs, 10 min-8 hrs, 30 sec-10 min, 1 min-10 min, 3 min-10 min, or 3 min-6 min. In some cases, a symptom of a neuropsychiatric disorder may be presence of increased power of low-frequency or theta (4-8 Hz) frequency electrical activity in the brain. In some cases, a treatment of the neuropsychiatric disorder may suppress increased power of low-frequency or theta (4-8 Hz) frequency electrical activity in the brain. The decrease in theta frequency power measured from the brain may be a decrease of 5%-20%, or more, such as, at least 5%, at least 10%, at least 15%, at least 20%, at least 40%, or more as compared to that prior to the treatment. The electrical activity may be recorded from any region of the brain, such as, OFC and/or regions of brain in neural connection with the OFC. In some cases, the electrical activity may be recorded from multiple locations in the brain and activity within different frequency bands averaged, for example, frequencies in the 4-8 Hz range recorded from multiple locations in the brain may be averaged. In some cases, the multiple locations may include, multiple locations in the OFC. The electrical activity may be measured prior to, during, and/or after stimulation of the brain as disclosed herein. In some cases, an increase in cortical excitability may be indicative of efficacious treatment. In some cases, other neural features, from a single brain region or a combination of brain regions, may be associated with a symptom of a neuropsychiatric disorder, or may be indicative of efficacious treatment.

In some cases, the brain activity, such as, theta frequency measured from the brain after a subject having a neuropsychiatric disorder is treated according to the methods and systems of the present disclosure, may be below a threshold brain activity, such as, theta activity. In certain cases, the threshold brain activity may be the brain activity known to be associated with the neuropsychiatric disorder. In some cases, theta frequency measured from the brain after a subject having a neuropsychiatric disorder is treated according to the methods and systems of the present disclosure, may be below a threshold theta activity. In certain cases, the threshold theta activity may be the theta activity known to be associated with the neuropsychiatric disorder.

In some cases, measurement of electrical signal from the brain may be combined with an alternate method for assessing the neuropsychiatric disorder. For example, the neuropsychiatric disorder may be assessed by mood assessment tools. Mood assessment tools may include verbal mood report or immediate mood scaler.

BRIEF DESCRIPTION OF THE DRAWINGS

FIG. 22). Error bars=SD

FIG. 19 illustrates sites of bipolar OFC stimulation among responders participating in a clinical study. Grey electrodes (marked by arrows) indicate the stimulation pair for each subject. Other OFC electrode pairs were not used for stimulation. Notably, a range of electrode locations within OFC, generally corresponding to lateral OFC, are effective in eliciting a positive mood effect. Positive effects were seen with both right and left OFC stimulation. While most patients are implanted unilaterally, note that bilateral (non-concurrent) OFC stimulation was undertaken with EC99 (see FIGS. 22 and 23).

FIG. 20 illustrates sites of bipolar OFC stimulation among non-responders participating in a clinical study. Grey electrodes (marked by arrows) indicate the stimulation pair for each subject. Other OFC electrode pairs were not used for stimulation. In marked contrast to responders, who all reported anxiety and/or depression symptoms prior to stimulation, all non-responders reported a normal and/or relaxed mood prior to (and after) stimulation (see FIGS. 22 and 23). Negative effects were seen with both right and left OFC stimulation.

FIG. 21 depicts a summary of stimulation sites and parameters for a set of five patients under study. Five epilepsy patients with subchronically implanted electrodes underwent short-duration stimulation of mesolimbic sites over 335 trials, over a range of current, frequency and pulse-width paramaters, as indicated. Mild anxiety was reported in 1/335 trials. Mood improvement was reported in none of the trials. OFC, orbitofrontal cortex; ACC, anterior cingulate cortex.

FIG. 22 depicts a summary of stimulation sites and outcomes for a set of nine patients under study. Duration of stimulation blocks was 10 minutes in most cases. Bold in the first column indicates "responder" status, defined as improvement of self-reported mood during OFC stimulation (bold type) compared to initial block of sham stimulation and any other stimulation condition. See FIG. 23 for self-report summaries. OFC, orbitofrontal cortex; vACC, ventral anterior cinguate cortex; dACC, dorsal anterior cingulate cortex.

FIG. 23 depicts a summary of subjective self-reports of mood state by patients represented in FIG. 22. Mood reports summarize patients' subjective self-report of mood concurrent with a 10-minute block of OFC stimulation at 100 Hz. Bold in the first column indicates "responder" status, defined as improvement of self-reported mood during OFC stimulation compared to initial block of sham stimulation and any other stimulation condition (see FIG. 21). Mood improvement in 7 of 10 epilepsy patients upon lateral OFC stimulation was seen. Of the remaining 3 patients, positive mood was reported throughout the experiment. All patients are blind to the onset and duration of sham and stimulation blocks. OFC, orbitofrontal cortex; IMS, Immediate Mood Scalar (quantitative self-report instrument).

FIGS. 26A-26C show OFC low frequency power negatively correlates with natural mood fluctuation in subjects with moderate-severe baseline mood trait.

FIGS. 27A-27E show local neurophysiological effects of OFC stimulation.

DETAILED DESCRIPTION

Figure 1A:
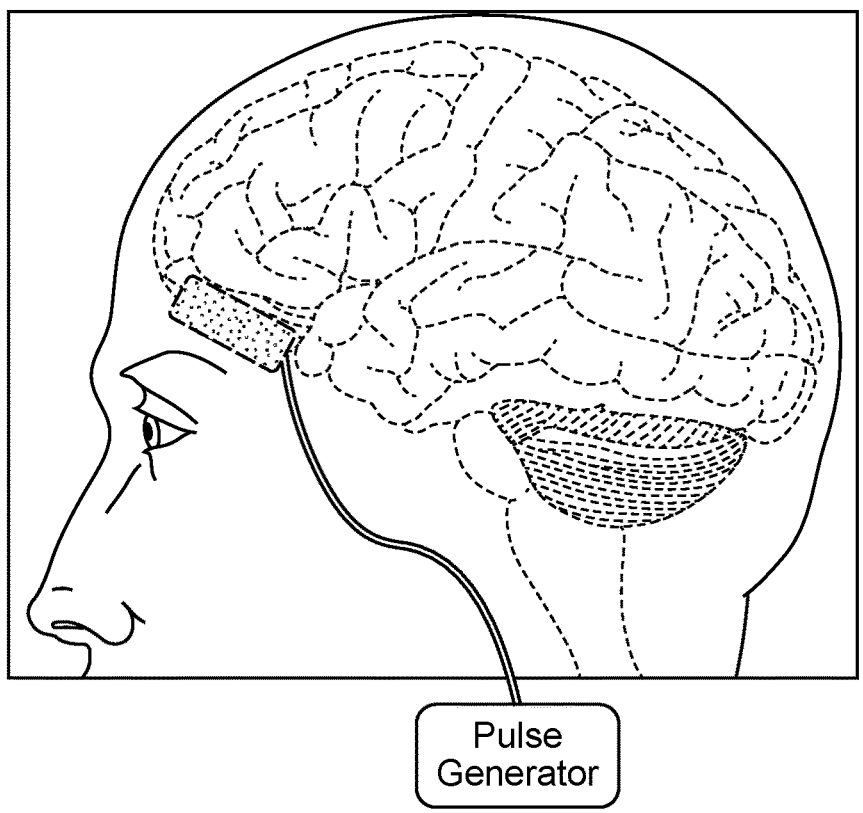
FIGS. 1A and 1B illustrate schematics for the stimulation of the OFC region using a surface electrode array (FIG. 1A) or a depth electrode array (FIG. 1B). Also depicted is a pulse generator and an implantable lead for activating the electrodes.

A method and system for treating neuropsychiatric disorders including affective disorders such as depression and/or anxiety and/or related disorders such as anorexia, OCD, PSD, Chronic Pain, and the like, through neuromodulatory intervention that includes brain targets within the orbitofrontal cortex (OFC) are provided. This method includes the application of electrical stimulation through at least one stimulating electrode in contact with the OFC. The treatment may further include patient selection, implantation of at least one stimulating electrode in contact with the OFC, acute or chronic electrical stimulation of the OFC, and evaluation of the effects of stimulation on clinical symptoms and status.

Neuropsychiatric disorders treated with the method may include MDD, GAD, PTSD, Addiction, OCD, Anorexia Nervosa, Bipolar Disorder, Chronic Pain, and related conditions. A patient may suffer from one or more of these neuropsychiatric disorders. The methods disclosed herein may treat more than one neuropsychiatric disorder in the same patient.

Before exemplary embodiments of the present invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an electrode" includes a plurality of such electrodes and reference to "a secondary area" or "the secondary area" includes reference to one or more secondary areas, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflicts with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Definitions

The term "neuropsychiatric disorders" is used herein to refer to a group of conditions that affect mood and/or behavior of a person suffering from the disorder. Neuropsychiatric disorders include Major Depressive Disorder (MDD), Generalized Anxiety Disorder (GAD), Post-Traumatic Stress Disorder (PTSD), Addiction, Anorexia, Obsessive-Compulsive Disorder (OCD), Bipolar Disorder (BD) and chronic pain.

The term "affective disorders" is used herein to refer to a group of neuropsychiatric disorders that typically affect mood of the person suffering from such a disorder. Neuropsychiatric disorders that affect the mood are also referred to as mood disorders and are commonly associated with depression and/or anxiety. The main types of affective disorders are depression, bipolar disorder, and anxiety disorder. Symptoms vary by individual, but they typically affect mood. They can range from mild to severe.

As used herein the term "depression" refers to a mental state of morbid sadness, dejection, or melancholy.

As used herein the term "anxiety" refers to an uncomfortable and unjustified sense of apprehension that may be diffuse and unfocused and is often accompanied by physiological symptoms.

As used herein the term "bipolar disorder" refers to a type of affective disorder in which the person suffering from this disorder goes through periods of depression and periods of mania (feeling extremely positive and active).

As used herein the term "anxiety disorder" refers to a neuropsychiatric disorder characterized by feelings of nervousness, anxiety, and even fear. Anxiety disorders include social anxiety (anxiety caused by social situations), post-traumatic stress disorder (anxiety, fear, and flashbacks caused by a traumatic event), generalized anxiety disorder (anxiousness and fear in general, with no particular cause), panic disorder (anxiety that causes panic attacks), and obsessive-compulsive disorder (obsessive thoughts that cause anxiety and compulsive actions).

By "treatment" or "treating" is meant that at least an amelioration of one or more symptoms associated with the condition afflicting the subject is achieved such that the patient has a desired or beneficial clinical result, where amelioration refers to at least a reduction in the magnitude of a parameter, e.g., a symptom, associated with the condition being treated. As such, treatment includes a broad spectrum of situations ranging from lessening intensity, duration or extent of impairment caused by a condition and/or correlated with a condition, up to and including completely eliminating the condition, along with any associated symptoms. Treatment therefore includes situations where the condition, or at least a symptom associated therewith, is completely inhibited, e.g., prevented from happening, or stopped, e.g., terminated, such that the subject no longer suffers from the condition, or at least the symptoms that characterize the condition. Treatment also includes situations where the progression of the condition, or at least the progression of a symptom associated therewith, is slowed, delayed, or halted. In such cases, a subject might still have residual symptoms associated the pathological condition, but any increase in the severity or magnitude of the symptoms is slowed, delayed, or prevented.

As used herein, the term "orbitofrontal cortex" or "OFC" refers to the defined area of brain as known by one of skill in the art, as well as the surrounding or adjacent white matter tracts leading to and from OFC. OFC is a prefrontal cortex region in the frontal lobes in the brain. In humans it consists of Brodmann area 10, 11 and 47.

"Brodmann area 10" or "BA10" refers to the defined area of Brodmann area 10 as known by one of skill in the art, as well as the surrounding or adjacent white matter tracts leading to and from Brodmann area 10 and/or white matter tracts that are contiguous with Brodmann area 10. The surrounding or adjacent white matter can include up to approximately a 1 cm radius of Brodmann area 10.

"Brodmann area 11" or "BA11" refers to the defined area of Brodmann area 11 as known by one of skill in the art, as well as the surrounding or adjacent white matter tracts leading to and from Brodmann area 11 and/or white matter tracts that are contiguous with Brodmann area 11. The surrounding or adjacent white matter can include up to approximately a 1 cm radius of Brodmann area 11.

"Brodmann area 47" or "BA47" refers to the defined area of Brodmann area 47 as known by one of skill in the art, as well as the surrounding or adjacent white matter tracts leading to and from Brodmann area 47 and/or white matter tracts that are contiguous with Brodmann area 47. The surrounding or adjacent white matter can include up to approximately a 1 cm radius of Brodmann area 47. Brodmann area 47 is also referred to as BA47/12.

The term "subject" as used herein refers to a patient in need of the treatments disclosed herein. The patient may be a mammal, such as, a rodent, a feline, a canine, a primate, or a human, e.g., a child, an adolescent, an adult, such as, an elderly human. The patient may have been diagnosed as having neuropsychiatric disorder, may be suspected of suffering from a neuropsychiatric disorder, or may be at risk of developing a neuropsychiatric disorder.

The term "user" as used herein refers to a person that interacts with a device and/system disclosed herein for performing one or more steps of the presently disclosed methods. The user may be the patient receiving treatment. The user may be a health care practitioner, such as, the patient's physician.

The term "symptom" as used in the context of a neuropsychiatric disorder, such as a symptom of a neuropsychiatric disorder refers to symptoms such as, anxiety, depression, fear, mania, and/or uncontrollable behavior.

Methods

The present disclosure provides methods for treating a neuropsychiatric disorder in a subject. Also provided herein are methods for ameliorating a symptom of a neuropsychiatric disorder in a subject. Various steps and aspects of the methods will now be described in greater detail below.

Methods of the present disclosure include applying electrical stimulation to Brodmann Area 11 (BA11) and/or Brodmann Area 47 (BA47) of orbitofrontal cortex region of brain of the subject. The method may include a step of positioning an electrode at BA11 and/or BA47 of OFC region of brain of the subject. One or more electrodes may be positioned at BA11, BA47, or both BA11 and BA47. The electrode may be non-brain penetrating surface electrode(s) or brain-penetrating depth electrode(s). The electrical stimulation may be applied in a manner effective for treating the neuropsychiatric disorder and/or ameliorating a symptom of the neuropsychiatric disorder. Such symptoms may include one or more of anxiety, depression, compulsive behavior, and the like.

The electrical stimulation may be applied using a single electrode, electrode pairs, or an electrode array. Electrical stimulation may be applied unilaterally to the BA11 and/or BA47 in the left or the right hemisphere of the brain. In certain embodiments, electrical stimulation may be applied bilaterally. Bilateral electrical stimulation may be simultaneous or sequential. In embodiments where the electrical stimulation is applied at least two times, the site to which the electrical stimulation is applied may be alternated or otherwise spatially or temporally patterned.

Positioning an electrode for applying electrical stimulation at the specified region(s) of the brain may be carried out using standard surgical procedure for placement of intracranial electrodes. As used herein, the phrases "an electrode" or "the electrode" refer to a single electrode or multiple electrodes such as an electrode array. As used herein, the term "contact" as used in the context of an electrode in contact with a region of the brain refers to a physical association between the electrode and the region. In other words, an electrode that is in contact with a region of the brain is physically touching the region of the brain. An electrode in contact with a region of the brain can conduct electricity into the brain. Electrodes used in the methods disclosed herein may be monopolar (cathode or anode) or bipolar (e.g., having an anode and a cathode). The electrode(s) used for applying electric stimulation to the specified region(s) of the brain are also referred to as stimulation electrode(s).

In certain cases, placing the electrode at BA11 and/or BA47 may involve positioning the electrode on the surface of the specified region(s) of the brain. The electrode may be placed on surface of brain at BA11, or BA47, or both. The electrode may contact at least a portion of the surface of the brain at BA11, or BA47, or both. In some embodiments, the electrode may contact substantially the entire surface area at BA11. In some embodiments, the electrode may contact substantially the entire surface area at BA47. In some embodiments, the electrode may additionally contact area(s) adjacent to BA11 and/or BA47. In some embodiments, an electrode array arranged on a planar support substrate may be used for electrically stimulating one or both regions of brains as specified herein. The surface area of the electrode array may be determined by the desired area of contact between the electrode array and the brain. An electrode for implanting on a brain surface, such as, a surface electrode or a surface electrode array may be obtained from a commercial supplier. A commercially obtained electrode/electrode array may be modified to achieve a desired contact area. In some cases, the non-brain penetrating electrode (also referred to as surface electrode) that may be used in the methods disclosed herein may be an electrocorticography (ECoG) electrode or an electroencephalography (EEG) electrode.

In certain cases, placing the electrode at a target area or site (i.e., BA11 and/or BA47) may involve positioning a brain penetrating electrode (also referred to as depth electrode) in the specified region(s) of the brain. The electrode may be placed in BA11, or BA47, or both. In some embodiments, the electrode may additionally contact area(s) adjacent to BA11 and/or BA47. In some embodiments, an electrode array may be used for electrically stimulating one or both regions of brains as specified herein. The depth to which the electrode is inserted into the brain may be determined by the desired level of contact between the electrode array and the brain. A brain-penetrating electrode array may be obtained from a commercial supplier. A commercially obtained electrode array may be modified to achieve a desired depth of insertion into the brain tissue.

In certain embodiments of the present methods, electrical stimulation is applied only to BA11, BA47, or BA11 and BA47. In certain embodiments, electrical stimulation is not applied to BA10. In other embodiments, electrical stimulation is applied at least to BA11 and one or more additional regions in the brain. In other embodiments, electrical stimulation is applied at least to BA47 and one or more additional regions in the brain. In other embodiments, electrical stimulation is applied to BA11, BA47, and one or more additional regions in the brain. In some embodiments, electrical stimulation is applied at least to BA11 and/or BA47 but not to another region in the brain.

The precise number of electrodes contained in an electrode array may vary. In certain aspects, an electrode array may include two or more electrodes, such as 3 or more, including 4 or more, e.g., about 3 to 6 electrodes, about 6 to 12 electrodes, about 12 to 18 electrodes, about 18 to 24 electrodes, about 24 to 30 electrodes, about 30 to 48 electrodes, about 48 to 72 electrodes, about 72 to 96 electrodes, or about 96 or more electrodes. The electrodes may be arranged into a regular repeating pattern (e.g., a grid, such as a grid with about 1 cm spacing between electrodes), or no pattern. An electrode that conforms to the target site for optimal delivery of electrical stimulation may be used. One such example, is a single multi contact electrode with eight contacts separated by 2½ mm. Each contract would have a span of approximately 2 mm. Another example is an electrode with two 1 cm contacts with a 2 mm intervening gap. Yet further, another example of an electrode that can be used in the present methods is a 2 or 3 branched electrode to cover the target site. Each one of these three pronged electrodes has four 1-2 mm contacts with a center to center separation of 2 of 2.5 mm and a span of 1.5 mm.

Figure 1B:
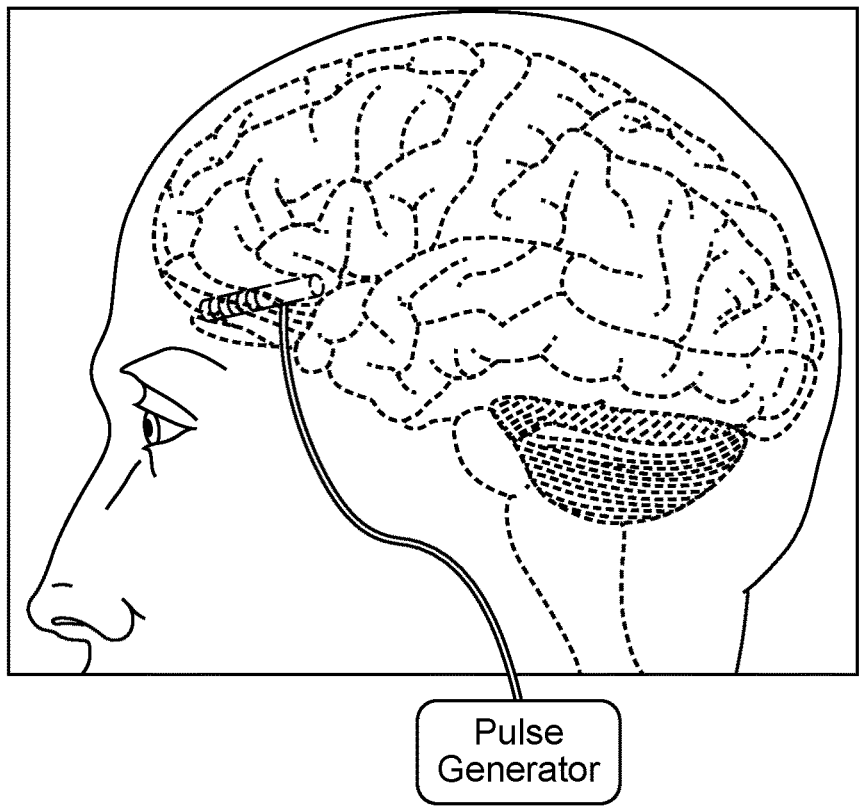
Figure 2A:
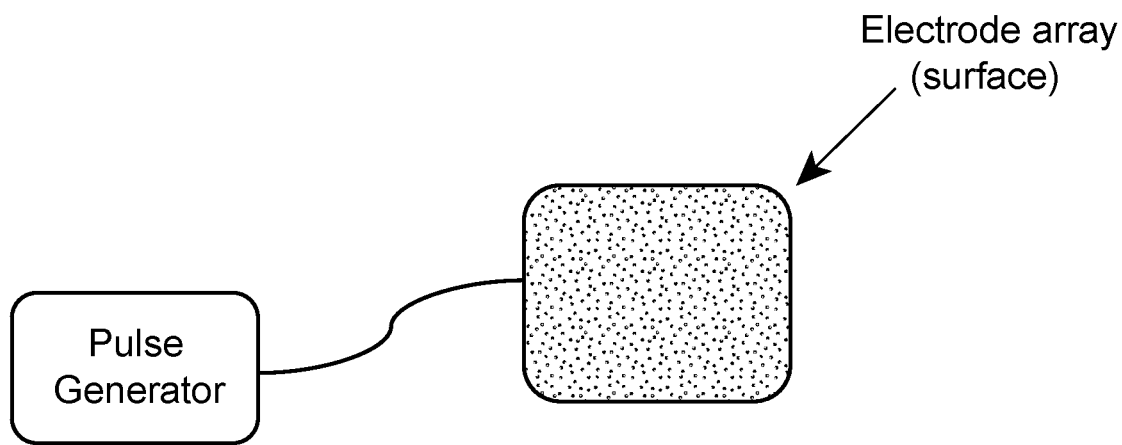
FIGS. 2A and 2B illustrate main components of a device capable of delivering stimulation to a region of the brain.
Figure 2B:
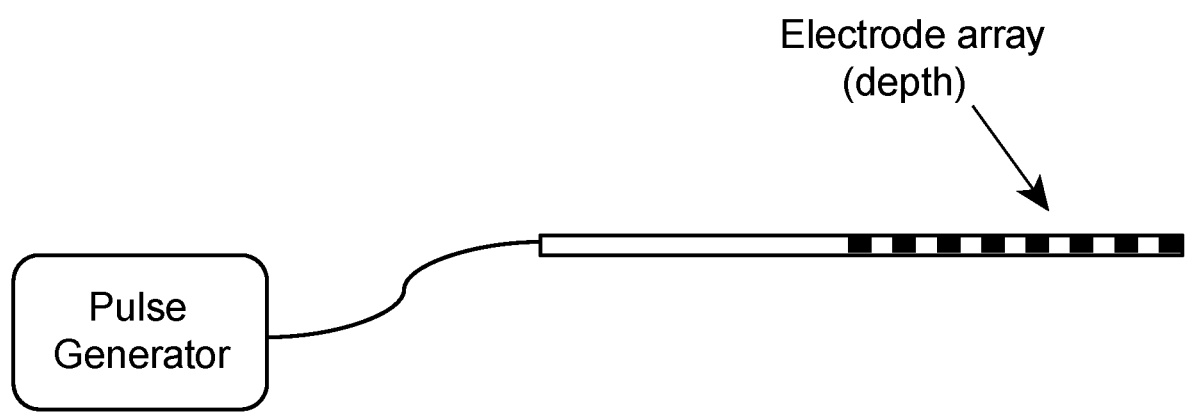
Figure 3B:
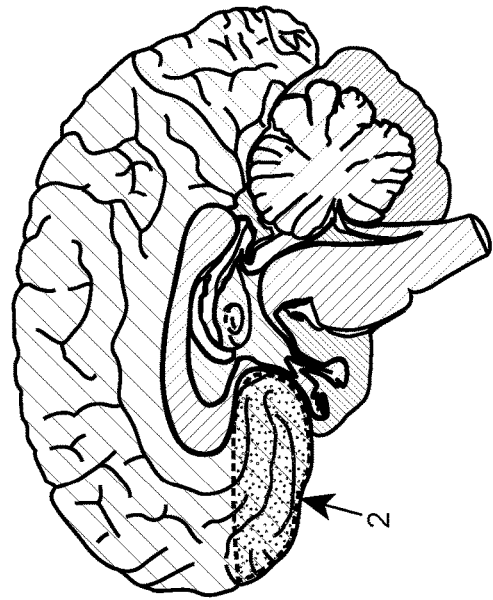
FIG. 3B depicts a left sagittal view of the cortical and subcortical regions.
Figure 3C:
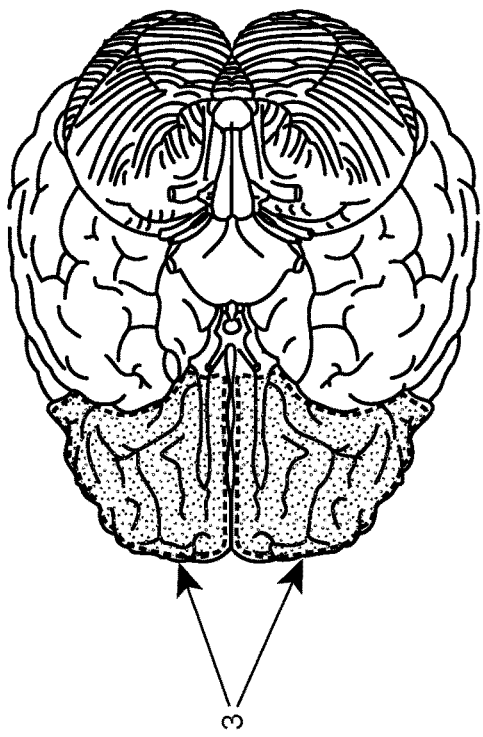
FIG. 3C depicts a ventral view of the brain's surface. The shaded areas 1, 2, and 3 indicate the OFC region.
Figure 3A:
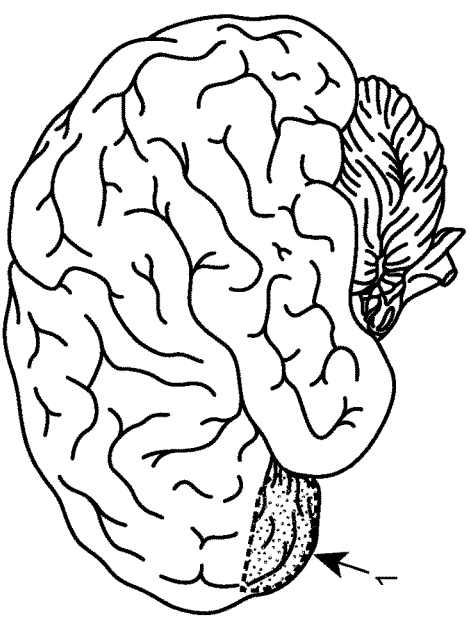
FIG. 3A depicts a left lateral view of the brain's surface.
Figure 4A:
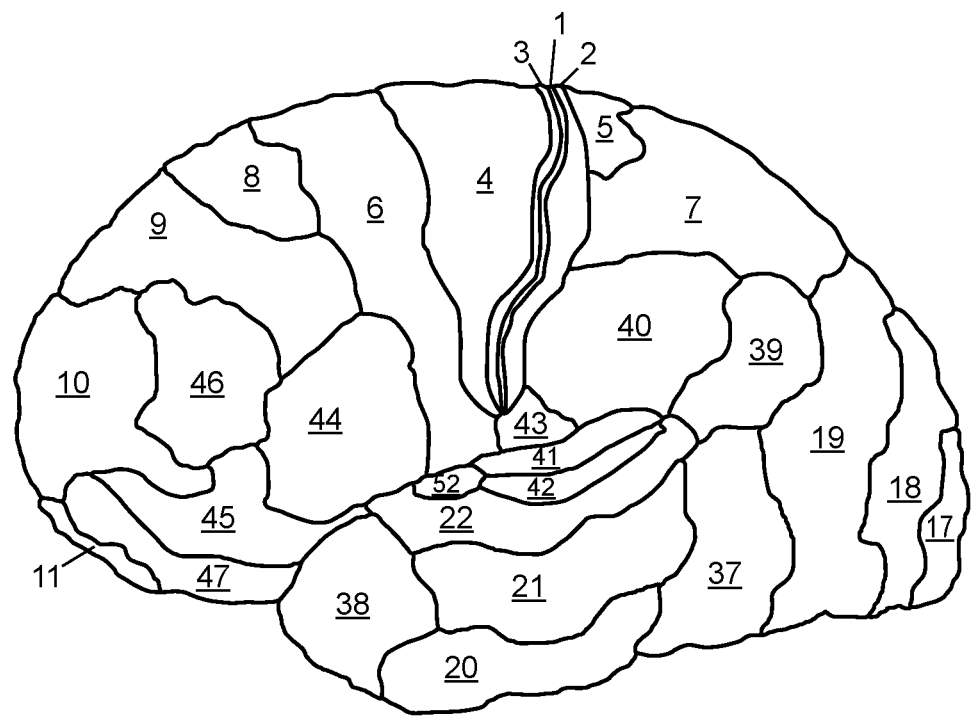
FIGS. 4A and 4B illustrate brain regions as traditionally demarcated per Brodmann according to cytoarchitectonic criteria. Brodmann Area 11 and Brodmann Area 47 in the OFC-centered region are shown.
Figure 4B:
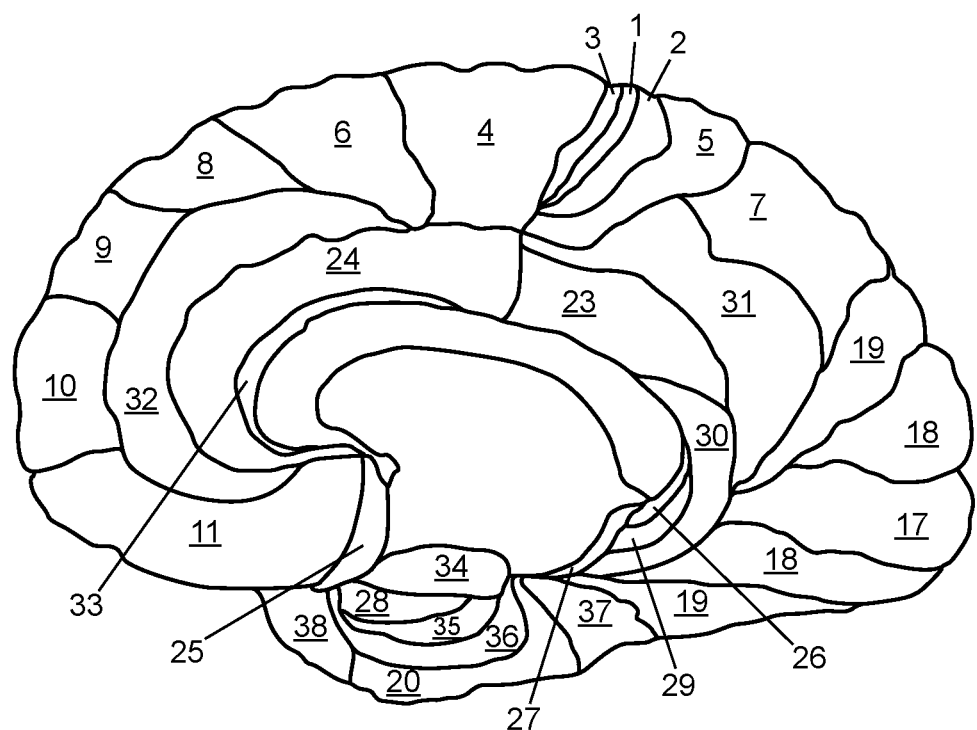

Exemplary electrodes and pulse generator for activating the electrodes to apply electrical stimulation to a target area of the brain via a conductive lead are depicted in FIGS. 1A, 1B, 2A, and 2B. In some embodiments, the target area of the brain may be BA11 and BA47. In FIGS. 3A-3C a target area is indicated by "1", "2", and "3". FIGS. 4A and 4B illustrate brain regions as traditionally demarcated per Brodmann according to cytoarchitectonic criteria. Brodmann Area 11 and Brodmann Area 47 in the OFC-centered region are shown. Numerous regions of the brain have been implicated in controlling mental state of a person. However, stimulation of different regions of the brain have been found to be mostly ineffective in treating neuropsychiatric disorders and for ameliorating symptoms of neuropsychiatric disorders such as depression or anxiety. For example, U.S. Pat. No. 8,190,264 discloses implanting a device for electrical stimulation of subgenual cingulate area, subcallosal cingulate area, ventral/medial prefrontal cortex area, ventral/medial white matter, Brodmann area 24, Brodmann area 25, and/or Brodmann area 10. However, electrical stimulation of these areas of the brain has not been shown in multi-center, double-blind trials to be effective in treating symptoms, such as, anxiety and/or depression. See Takashi Morishita, Sarah M. Farad, Masa-aki Higuchi, Kelsey A. Nestor, and Kelly D. Foote. Deep Brain Stimulation for Treatment-resistant Depression: Systematic Review of Clinical Outcomes. Neurotherapeutics. 2014 July; 11(3): 475-484. doi: 10.1007/s13311-014-0282-1.

The size of each electrode may also vary depending upon such factors as the number of electrodes in the array, the location of the electrodes, the material, the age of the patient, and other factors. In certain aspects, an electrode array has a size (e.g., a diameter) of about 5 mm or less, such as about 4 mm or less, including 4 mm-0.25 mm, 3 mm-0.25 mm, 2 mm-0.25 mm, 1 mm-0.25 mm, or about 3 mm, about 2 mm, about 1 mm, about 0.5 mm, or about 0.25 mm.

As set forth here, the method involves applying electrical stimulation to BA11 and/or BA47 in a manner effective to treat the neuropsychiatric disorder and/or a symptom of the neuropsychiatric disorder in the subject. The parameters for applying the electrical stimulation may be determined empirically during treatment or may be pre-defined, such as, from a clinical study. The parameters of the electrical stimulation may include one or more of frequency, pulse width/duration, duty cycle, intensity/amplitude, pulse pattern, program duration, program frequency, and the like.

Frequency refers to the pulses produced per second during stimulation and is stated in units of Hertz (Hz, e.g., 60 Hz=60 pulses per second). The frequencies of electrical stimulation used in the present methods may vary widely depending on the numerous factors and may be determined empirically during treatment of the subject or may be pre-defined. In certain embodiments, the method may involve applying an electrical stimulation at a frequency of 10 Hz-500 Hz, such as, 10 Hz-300 Hz, 10 Hz-200 Hz, 10 Hz-150 Hz, 10 Hz-125 Hz, 10 Hz-100 Hz, 15 Hz-200 Hz, 15 Hz-300 Hz, 20 Hz-200 Hz, 25 Hz-400 Hz, 25 Hz-300 Hz, 25 Hz-200 Hz, 25 Hz-150 Hz, 25 Hz-100 Hz, 50 Hz-500 Hz, 50 Hz-400 Hz, 50 Hz-300 Hz, 50 Hz-200 Hz, 50 Hz-150 Hz, 50 Hz-100 Hz, 75 Hz-300 Hz, 75 Hz-200 Hz, 75 Hz-150 Hz, 75 Hz-125 Hz, 75 Hz-120 Hz, 75 Hz-115 Hz, 75 Hz-110 Hz, or 75 Hz-100 Hz. The amplitude of current may be 0.1 mA-30 mA, such as, 0.1 mA-25 mA, such as, 0.1 mA-20 mA, 0.1 mA-15 mA, 0.1 mA-10 mA, 1 mA-20 mA, 1 mA-10 mA, 2 mA-30 mA, 2 mA-15 mA, or 2 mA-10 mA.

The electrical stimulation may be applied in pulses such as a uniphasic or a biphasic pulse. The time span of a single pulse is referred to as the pulse width or pulse duration. The pulse width used in the present methods may vary widely depending on the numerous factors (e.g., severity of the disease, status of the patient, and the like) and may be determined empirically or may be pre-defined. In certain embodiments, the method may involve applying an electrical stimulation at a pulse width of about 10 μsec-990 μsec, for example, 30 μsec-990 μsec, 50 μsec-990 μsec, 75 μsec-990 μsec, 100 μsec-990 μsec, 200 μsec-990 μsec, 300 μsec-990 μsec, 500 μsec-990 μsec, 500 μsec-900 μsec, 30 μsec-900 μsec, 50 μsec-900 μsec, 75 μsec-900 μsec, 100 μsec-900 μsec, 200 μsec-900 μsec, 300 μsec-900 μsec, 500 μsec-900 μsec, 30 μsec-500 μsec, 50 μsec-450 μsec, 75 μsec-300 μsec, 100 μsec-200 μsec, or 100 μsec-550 μsec.

The electrical stimulation may be applied for a stimulation period of 0.1 sec-1 month, with periods of rest (i.e., no electrical stimulation) possible in between. In certain cases, the period of electrical stimulation may be 0.1 sec-1 week, 1 sec-1 day, 10 sec-12 hrs, 1 min-6 hours, 10 min-1 hour, and so forth. In certain cases, the period of electrical stimulation may be 1 sec-1 min, 1 sec-30 sec, 1 sec-15 sec, 1 sec-10 sec, 1 sec-5 sec, 1 sec-3 sec, 1 sec-2 sec, or 5 sec-10 sec. The period of rest in between each stimulation period may be 60 sec or less, 30 sec or less, 20 sec or less, or 10 sec. The amplitude of current may be 0.1 mA-30 mA, such as, 0.1 mA-25 mA, such as, 0.1 mA-20 mA, 0.1 mA-15 mA, 0.1 mA-10 mA, 1 mA-20 mA, 1 mA-10 mA, 2 mA-30 mA, 2 mA-15 mA, or 2 mA-10 mA.

The electrical stimulation having the parameters as set forth above may be applied over a program duration of around 1 day or less, such as, 18 hours, 6 hours, 3 hours, 1 hour, 45 minutes, 30 minutes, 20 minutes, 10 minutes, or 5 minutes, or less, e.g., 1 minute-5 minutes, 2 minutes-10 minutes, 2 minutes-20 minutes, 2 minutes-30 minutes, 5 minutes-10 minutes, 5 minutes-30 minutes, or 5 minutes-15 minutes which period would include the application of pulses and the intervening rest period. The program may be repeated at a desired program frequency till treatment of the subject is achieved. As such, a treatment regimen may include a program for electrical stimulation at a desired program frequency and program duration. In some embodiments, the treatment regimen may be controlled by a user via a pulse generator connected to the one or more stimulation electrodes in an open-loop treatment regimen. In other embodiments, the treatment regimen may be controlled by a control unit in communication with a pulse generator connected to the one or more stimulation electrodes in a closed-loop treatment regimen. Closed-loop treatment methods and systems are further described elsewhere in this disclosure.

As noted above, the treatment may ameliorate one or more symptoms of the neuropsychiatric disorder suffered by the subject. Such symptoms include anxiety, depression, frequency of episodes of compulsive behavior, frequency of self-starvation episodes, mania, panic attacks, social anxiety, or distress related to chronic pain. Assessment of effectiveness of the treatment may be performed by neurological examinations and/or neuropsychological tests (e.g., Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, Montgomery-Åsberg Depression Rating Scale (MADRS), Yale-Brown Obsessive Compulsive score (Y-BOCS)), motor examination, visual analog scales of pain symptoms, and/or cranial nerve examination.

In certain cases, the symptom that may be ameliorated by the disclosed method may be anxiety. Anxiety of a subject may be assessed using any standardized assessment method. In certain cases, anxiety may be measured by self-reporting, such as, by a Beck Anxiety Inventory (BAI) score or Hamilton Anxiety Rating Scale (HAM-A). Additional measures of anxiety include State-straight anxiety inventory (STAI) which consists of State Anxiety Scale (S-Anxiety) and Trait Anxiety Scale (T-Anxiety) and hospital anxiety and depression scale-Anxiety (HADS-A). Amelioration of anxiety may include a reduction in anxiety level compared to the anxiety level prior to the treatment. A 5% or higher reduction in anxiety level (measured by BAI or HAM-A, for example), may indicate that the treatment was effective.

In certain cases, the symptom that may be ameliorated by the disclosed method may be depression. Depression of a subject may be assessed using any standardized assessment method. In certain cases, depression may be measured by self-reporting, such as, by a Beck Depression Inventory (BDI) score, Center for Epidemiological Studies Depression Scale (CES-D), Geriatric Depression Scale (GDS), or Zung Self-Rating Depression Scale (Zung SDS). In certain cases, an interviewer-administered depression assessment may be used alone or in conjunction with a self-reporting tool. Interviewer-administered depression assessments include Cornell Scale for Depression in Dementia (CSDD) and RAND Corporation Self-Administered Depression Screener Amelioration of depression may include a reduction in depression level compared to the depression level prior to the treatment. A 5% or higher reduction in depression level (measured by BDI score, for example), may indicate that the treatment was effective.

In certain cases, effectiveness of treatment may be assessed by detecting activity (e.g., electrical signals) from a secondary region of the brain, which may be within Brodmann 11 and/or 47, or another area. For example, the secondary region(s) may be one or more of the OFC, amygdala, hippocampus, septum, cingulate gyms, cingulate cortex, hypothalamus, epithalamus, anterior thalamus, mammillary bodies, and fornix. In certain embodiments, the secondary region may be amygdala and/or hippocampus. Detection of brain activity at a secondary region of the brain may be performed by functional brain imaging. Functional brain imaging may be carried out by electrical methods such as electroencephalography (EEG), magnetoencephalography (MEG), single photon emission computed tomography (SPECT), as well as metabolic and blood flow studies such as functional magnetic resonance imaging (fMRI), and positron emission tomography (PET). In some embodiments, electrical methods for assessing effectiveness of treatment may involve placement of an electrode for measuring electrical signals at a secondary region of the brain. One or more of the aforementioned secondary regions may be implanted with an electrode and electrical signals measured for assessment of effectiveness of the treatment. The electrodes used for measuring brain activity are referred herein as measurement electrodes. Any suitable electrodes may be used for measurements and may include one or more surface electrodes (non-brain penetrating electrode(s)) or one or more depth electrodes (brain penetrating electrode(s)) as described herein.

Assessment of effectiveness of treatment and assessment of amelioration of a symptom of the neuropsychiatric disorder may be performed at any suitable time point after commencement of the treatment procedure, for example, after a treatment regimen is complete. Embodiments of the subject methods include assessing effectiveness of treatment or amelioration of a symptom of the neuropsychiatric disorder within seconds, minutes, hours, or days after the initial treatment regimen has been completed. In some instances, assessment may be performed at multiple time points. In some cases, more than one type of assessment may be performed at the different time points. In some embodiments, a subject's brain activity (e.g., at one or more secondary regions) may be measured prior to the application of electrical stimulation to BA11 and/or BA47 and assessing may include comparing the subject's brain activity at one or more secondary regions after the treatment to that before the treatment and a change in the post-treatment brain activity may indicate successful treatment.

As such, the methods and systems provided herein may be used to ameliorate one or more symptoms of a neuropsychiatric disorder in a patient. A person skilled in the art will appreciate that amelioration of a symptom may provide relief to a patient suffering from two separate neuropsychiatric conditions which share the symptom.

Upon completion of a treatment regimen, the patient may be assessed for effectiveness of the treatment and the treatment regimen may be repeated, if needed. In certain cases, the treatment regimen may be altered before repeating. For example, one or more of the frequency, pulse width, current amplitude, period of electrical stimulation, program duration, and/or program frequency may be altered before starting a second treatment regimen.

In certain cases, the treatment regimen may be tailored to the desired outcome. For example, for a patient suffering from an acute form of a neuropsychiatric disorder(s), the treatment regimen may be chosen to provide an acute alleviation of one or more symptoms of the disorder(s). In contrast, the treatment regimen for a patient suffering chronically from a neuropsychiatric disorder(s) may be tailored for a chronic relief of one or more symptoms of the disorder(s). A treatment regimen for chronic relief of one or more symptoms of the disorder(s) may also delay reappearance of symptoms of the chronic relief of one or more symptoms of the disorder(s) and may even prevent the symptoms from appearing. In certain cases, a treatment regimen that is a combination of treatment regimens for acute and chronic alleviation of one or more symptoms of the disorder(s) may be employed.

Application of the method may include a prior step of selecting a patient for treatment based on need as determined by clinical assessment, which may include cognitive assessment, anatomical assessment, behavioral assessment and/or neurophysiological assessment. In certain cases, a subject may be selected for treatment if the subject is at risk of suffering from a neuropsychiatric disorder. A patient who has a family history of neuropsychiatric disorders or has previously suffered from neuropsychiatric disorders may be at risk. Such a patient may also be implanted with intracranial stimulation electrodes at BA11 and/or BA47.

In certain aspects, the methods and systems of the present disclosure may include measurement of brain activity, for example, electrical activity in the OFC, where level of low-frequency power may be measured. In certain cases, electrical activity from a plurality of locations in the OFC may be measured and averaged. For example, electrical activity in the low frequency range (such as 4-8 Hz) may be measured from the OFC, insula, amygdala, hippocampus, dorsal cingulate, and/or subgenual cingulate. In some cases, electrical activity in one or more locations in the brain may be measured during a period extending from prior to stimulation to the period during which stimulation to the brain is applied, or to a period after stimulation to the brain has been applied, and monitored for a decrease in the power of low-frequency (such as 4-8 Hz) activity and/or increase in cortical excitability. In some cases, when decreased power of low-frequency (such as 4-8 Hz) activity and/or increased cortical excitability is within a normal range (e.g., a range associated with a substantial lack of the disorder), the methods and systems do not apply a further stimulation to the brain. Alternatively, when decreased power of low-frequency (such as 4-8 Hz) activity and/or increased cortical excitability is not within a normal range (e.g., a range associated with a substantial lack of the disorder), the methods and systems may apply a further stimulation to the brain. In certain cases, the application of electrical stimulation to the brain may suppress low-frequency power across insula, dorsal cingulate, and subgenual cingulate. In some cases, the application of electrical stimulation to the brain may suppress theta frequency band power in OFC, insula, and cingulate cortices. In certain cases, the application of electrical stimulation to the brain may decrease beta range frequencies in amygdala and in dorsal cingulate. The decrease may be as compared to the power prior to the application of stimulation. In certain cases, the application of electrical stimulation to the brain may alter other neural features from one more regions of the brain. The alterations may be compared to the state of these features prior to the application of stimulation.

Figure 8:
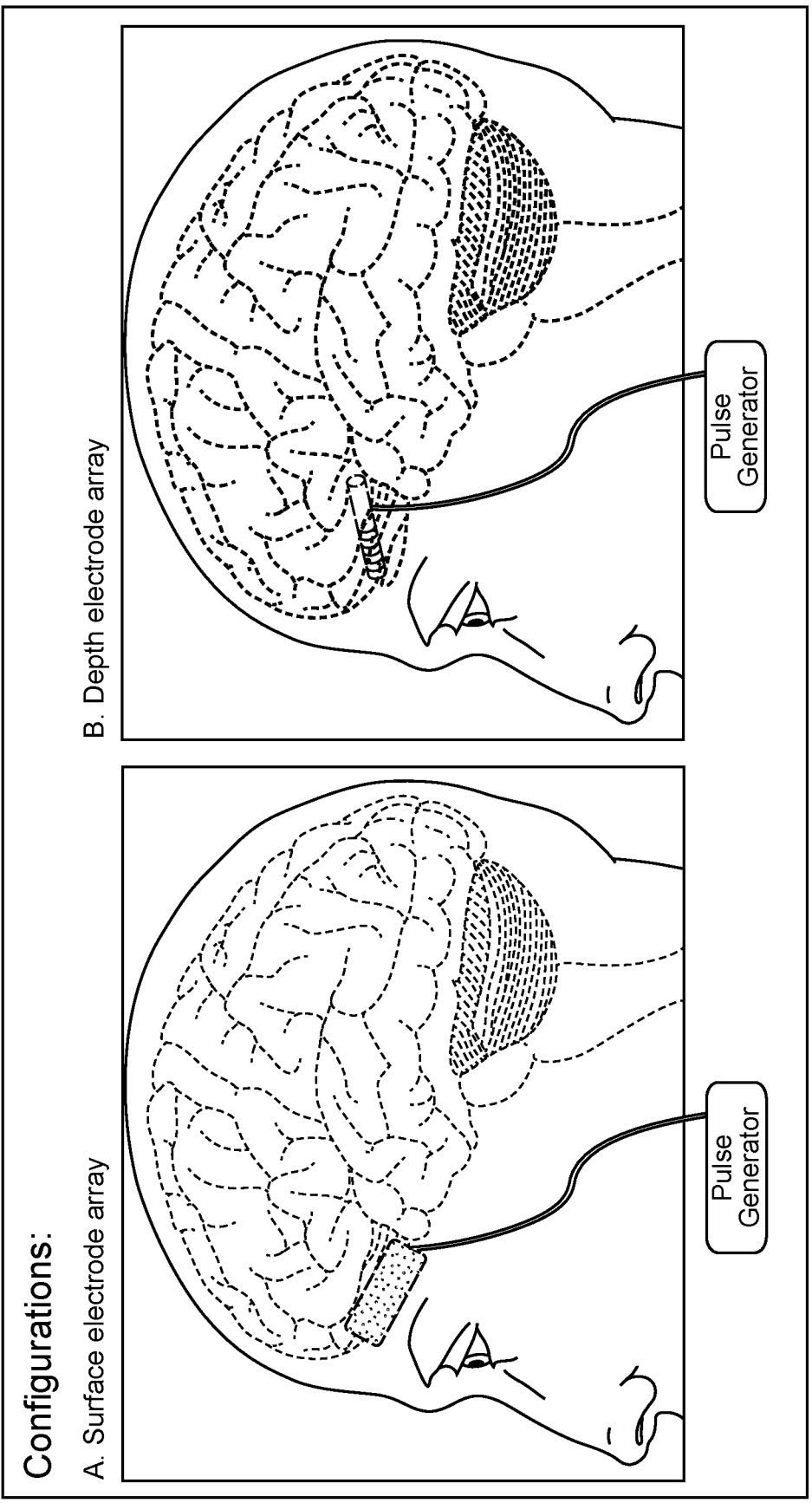
FIG. 8 depicts device configurations and a clinical process for open-loop OFC stimulation to achieve symptom control.
Figure 8:
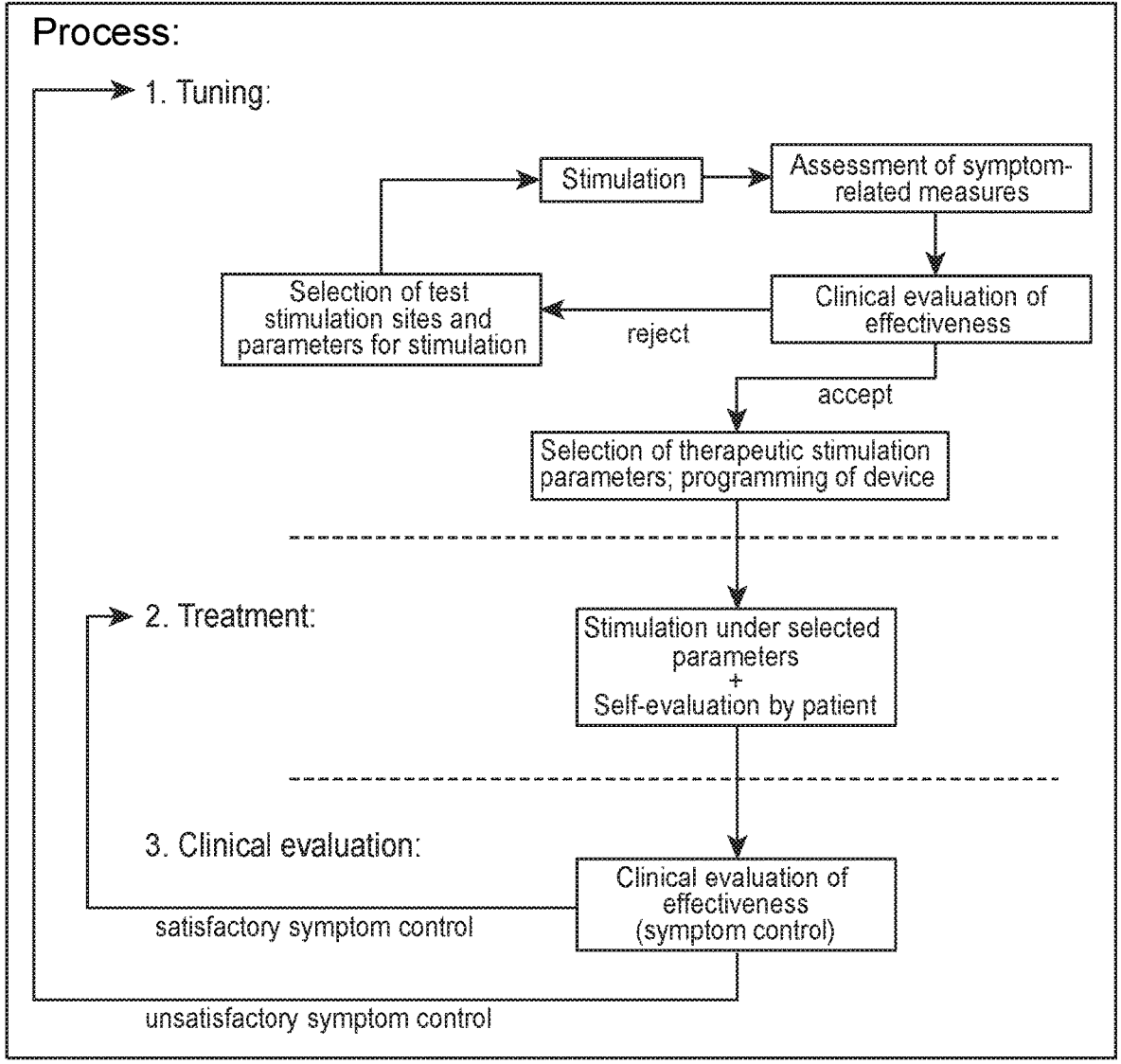

The foregoing methods may be performed as an open-loop method. Exemplary open-loop methods and associated systems for treatment of a neuropsychiatric disorder are further discussed in the Examples section and are depicted in FIG. 8.

In other embodiments, the foregoing methods may be configured as a closed-loop. A closed-loop method allows determination of parameters of electrical stimulation based upon real-time feedback signal from the brain of the subject. Closed-loop methods and systems allow for automation of treatment of the subject including real-time need-based modulation of the treatment regimen. Closed-loop methods and systems are further described below.

Closed-Loop Method

In certain aspects, a closed-loop method for treating a neuropsychiatric disorder in a subject is provided. According to certain embodiments, the method may include applying electrical stimulation to the Brodmann Area 11 and/or Brodmann Area 47 via the stimulation electrode in a manner effective to treat the neuropsychiatric disorder; receiving an electrical signal from the secondary area of the brain of the subject via the measurement electrode; applying the electrical signal metrics to a control algorithm that is tuned to a clinically relevant target (e.g., a range of signal indicative of effective treatment); modulating one or more programmed stimulation parameters according to the algorithm's control law; and applying the modulated electrical stimulation to the Brodmann Area 11 and/or Brodmann Area 47 via the stimulation electrode in a manner effective to treat the neuropsychiatric disorder.

Also described herein is a closed-loop method for ameliorating a symptom of a neuropsychiatric disorder in a subject. In certain aspects, the method may include applying electrical stimulation to the Brodmann Area 11 and/or Brodmann Area 47 via the stimulation electrode in a manner effective to ameliorate the symptom of the neuropsychiatric disorder; receiving an electrical signal from the secondary area of the brain of the subject via the measurement electrode; applying the electrical signal metrics to a control algorithm that is tuned to a clinically relevant target (e.g., a range of signal indicative of effective treatment); modulating one or more programmed stimulation parameters according to the algorithm's control law; and applying the modulated electrical stimulation to the Brodmann Area 11 and/or Brodmann Area 47 via the stimulation electrode in a manner effective to ameliorate the symptom the neuropsychiatric disorder.

As described in the foregoing sections, effectiveness of treatment or amelioration of a symptom of the neuropsychiatric disorder may be assessed by detecting electrical activity from a secondary region(s) of the brain. In an open-loop system, stimulation is delivered in a pre-programmed way or manually by a user, but is not automatically controlled by real-time neural feedback from the patient's brain. The electrical activity may be analyzed by a computing means which may output recommendations based on comparing the electrical activity to a predetermined range. A user may then carry out the recommendations, such as, changing a parameter of the electrical stimulation program prior to starting another treatment regimen. In a closed-loop system, by contrast, a computing means can automatically update stimulation parameters based upon analysis of the recorded electrical signal. In some embodiments, either an open-loop or a closed-loop system may be integrated with a mechanism for user intervention, for example by allowing user-override of open-loop or closed-loop stimulation programs to enact or prevent stimulation that would ordinarily occur, or to manually change parameters of such stimulation.

Location and types of electrodes used for measuring signals from a secondary area of the brain may be as described in the foregoing sections. In some embodiments, the computing means for directing closed-loop stimulation may be a combination of hardware/software which may be connected wirelessly or by wire to the measurement electrodes. The computing means may communicate with a control unit (also referred to as a control module) that controls a pulse generator connected to the stimulation electrodes. In certain embodiments, the computing means may be connected to a recorder (e.g., a neurophysiological recorder) that records brain activity measured by the measurement electrodes. The computing means may include a control algorithm that determines modification of stimulation parameters based on real-time outputs of the neurophysiological recorder. The algorithm may operate by simple on/off control of stimulation at set parameters, modifying only the on/off parameter with each evaluation cycle, or may determine sophisticated modification of a range of stimulation parameters with each cycle. In some cases, the algorithm may be based on information related to the neuropsychiatric disorder, such as, a range of electrical activity that is indicative of the presence of the neuropsychiatric disorder. The algorithm may also include additional information such as brain activity profile of a normal subject (not suffering from a neuropsychiatric disorder). Regardless of the particular control algorithm structure, the computing means may be tuned to a clinically relevant target (e.g., a range of signal indicative of effective treatment) that directs modulation of one or more programmed stimulation parameters according to the algorithm's control law, applying the modulated electrical stimulation to the Brodmann Area 11 and/or Brodmann Area 47 via the stimulation electrode.

In some cases, the computing means, via a control algorithm, may determine whether the received electrical signals are within or outside a predetermined range of neural signals indicative of the presence of the neuropsychiatric disorder. When the received electrical signals are outside this predetermined range, then the computing means determines that the neuropsychiatric disorder has been treated and/or a symptom of the neuropsychiatric disorder (e.g., depression, anxiety, compulsive/repetitive, self-starvation behavior, and/or chronic-pain-related distress) has been ameliorated. The computing means may then communicate with the control unit to direct stimulation shut-off by the pulse generator. When the received electrical signals are within the predetermined range of neural signals indicative of the presence of the neuropsychiatric disorder, then the computing means determines that the neuropsychiatric disorder has not been treated and/or a symptom of the neuropsychiatric disorder (e.g., depression, anxiety, compulsive/repetitive, self-starvation behavior, and/or chronic-pain-related distress) has not been ameliorated. The control algorithm within the computing means may then determine whether the initial step of applying electrical stimulation to BA11 and/or BA47 should be repeated and/or whether a parameter of the electrical stimulation modified prior to the step of applying electrical stimulation to BA11 and/or BA47. The computing means, via the control unit, may then communicate with the control unit to provide the appropriate instructions to the pulse generator.

In some embodiments, the computing means may determine whether the received electrical signals are within or outside a second predetermined range, where the second predetermined range is indicative of treatment of the neuropsychiatric disorder and/or amelioration of a symptom of the neuropsychiatric disorder. When the received electrical signals are within the second predetermined range, then the computing means determines that the neuropsychiatric disorder has been treated and/or a symptom of the neuropsychiatric disorder (e.g., depression, anxiety, compulsive/repetitive, self-starvation behavior, and/or chronic-pain-related distress) has been ameliorated. The computing means may then communicate with the control unit to direct stimulation switch-off by the pulse generator. When the received electrical signals are outside the second predetermined range, then the computing means determines that the neuropsychiatric disorder has not been treated and/or a symptom of the neuropsychiatric disorder (e.g., depression, anxiety, compulsive/repetitive, self-starvation behavior, and/or chronic-pain-related distress) has not been ameliorated. The control algorithm within the computing means may then determine whether the initial step of applying electrical stimulation to BA11 and/or BA47 should be repeated and/or whether a parameter of the electrical stimulation modified prior to the step of applying electrical stimulation to BA11 and/or BA47. The processor may then communicate with the control unit to provide the appropriate instructions to the pulse generator.

Figure 10:
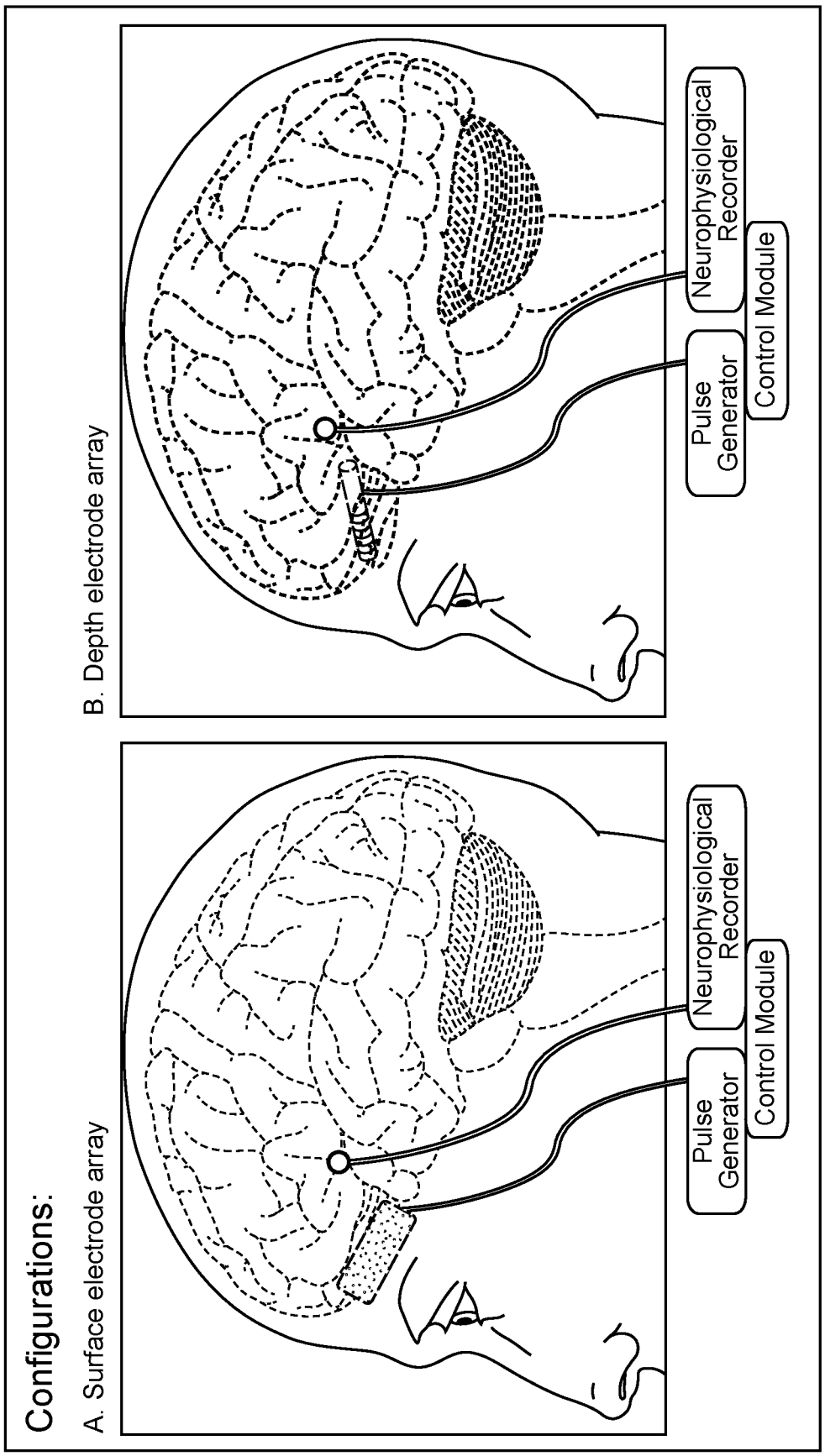
FIG. 10 depicts device configurations and a process for closed-loop OFC stimulation to achieve symptom control.

Thus in certain aspects, the subject methods operate as a closed-loop control system which may automatically adjust one or more parameters in response to electrical activity from a region of the brain of a subject. Exemplary closed-loop methods and associated systems are described in the Examples section of the application and are illustrated in FIG. 10.

In some aspects, the closed loop system may be used to sense a subject's need for treatment using the methods disclosed herein. For example, the closed loop system may be programmed to monitor brain activity from one or more secondary regions of the brain and compare the brain activity to a range indicative of the neuropsychiatric disease or a symptom of the neuropsychiatric disease. Upon detection of electrical activity indicative of the neuropsychiatric disease or a symptom of the neuropsychiatric disease, the closed loop system may automatically commence a treatment protocol of applying electrical stimulation of BA11 and/or BA47.

In additional aspects, the closed loop system may be used as a system for monitoring brain activity and correlating the brain activity to the subject's mental state. For example, since the closed loop system is configured for recording electrical signals from a subject's brain, the subject's mood and/or behavior may be monitored in real-time and correlated to the measured electrical signals to provide a biomarker that is related to the subject's mental state. For example, electrical activity measured when a subject is anxious can be used to develop a biomarker, e.g., as range of electrical activity indicative of anxiety and so on.

As such, closed loop systems are useful for prognosis as well as diagnosis of neuropsychiatric disorders.

It is understood that electrical signals that are indicative of a mental state of a subject may be recorded from a subject's brain and may be used in aspects outside of a closed loop system. For example, electrical signals indicative of a mental state of a subject may be recorded from the OFC, amygdala, hippocampus, cingulate, frontal pole, and/or lateral frontal lobe using electrodes or another device operably coupled to the patient's brain which electrodes or device may or may not be part of a closed loop system. The patient may be treated as disclosed herein (e.g., by applying electrical stimulation to Broadmann 11 and/or 47), and electrical signals recorded from the same region in real time as the treatment is administered or after the treatment is administered. The electric signals recorded after the administration of electrical stimulation is commenced may then be compared to the electric signals recorded prior to the treatment to determine features in the recorded electric signals that change post-treatment. These features provide a feedback signal to indicate whether the treatment is having an effect on the patient's mental state. These features can also serve as feedback signals to a closed loop system. These features may include the overall power, or power in specific frequency ranges (e.g. Alpha, delta, beta, gamma, and/or high gamma). In some cases, these features may be patient specific or specific to a particular mental state or both. For example, some of the features may be features found in a plurality of patients having a particular mental state (e.g., anxiety); some of the features may be features in a particular patient which may not be found in a significant number of other patients having the same mental state. In some embodiments, a combination of patient-specific features and mental state specific features may be monitored to assess efficacy of treatment.

In a particular aspect, the closed loop system and methods provided herein may involve a recording of electrical signals from one or more regions (e.g., OFC, amygdala, hippocampus, cingulate, frontal pole, and/or lateral frontal lobe) of a patient's brain, where the patient has a neuropsychiatric disorder. The patient may then be treated by application of electrical stimulation to the Brodmann Area 11 and/or Brodmann Area 47 and electrical signals recorded from same regions of the brain and compared to the pre-treatment recording. Features in the recorded signals that changed after the treatment would correspond to biomarkers that indicate whether the treatment is having an effect. The change in recorded signals can also optionally be correlated to mental state reported by the patient after the treatment. The change can be used for modulating the treatment in a closed loop system. For example, when the change in recorded signal correlate to an improvement in the patient's mood, those features would indicate to a computing means of a closed loop system that further treatment need not be performed.

In certain aspects, methods of the present disclosure that may be embodied in an open- or a closed-loop system may include measuring brain activity from a subject having or suspected or having a neuropsychiatric disorder, such as, anxiety and/or depression, where when the subject has a level of low frequency activity (e.g., 4-8 Hz) that is higher than a normal range (e.g., range reflective of a normal brain, such as, brain of a person not suffering from the disorder), the subject is treated by applying electrical stimulation to the Brodmann Area 11 and/or Brodmann Area 47 via an electrode positioned at or adjacent BA11 and/or BA47 in a manner effective to reduce the level of low frequency activity (e.g., 4-8 Hz) in the brain of the subject. The brain activity may be measured from one or more of OFC, insula, dorsal cingulate, subgenual cingulate, and cingulate cortices. In some aspects, such as in a closed loop system, the system may monitor brain activity such as level of low frequency activity and if the level of low frequency activity is higher than a reference range (e.g., range reflective of a normal brain, such as, brain of a person not suffering from the disorder), the closed loop system may apply electrical stimulation to the Brodmann Area 11 and/or Brodmann Area 47 via an electrode positioned at or adjacent BA11 and/or BA47 in a manner effective to reduce the level of low frequency activity (e.g., 4-8 Hz) in the brain of the subject.

In certain aspects, methods of the present disclosure that may be embodied in an open- or a closed-loop system may include measuring brain activity from a subject having or suspected or having a neuropsychiatric disorder, such as, anxiety and/or depression, where when the subject has a level of beta range frequencies (e.g., 13-30 Hz) that is higher than a normal range (e.g., range reflective of a normal brain, such as, brain of a person not suffering from the disorder), the subject is treated by applying electrical stimulation to the Brodmann Area 11 and/or Brodmann Area 47 via an electrode positioned at or adjacent BA11 and/or BA47 in a manner effective to reduce the level of beta range frequencies in the brain of the subject. The brain activity may be measured from one or more of amygdala and dorsal cingulate. In some aspects, such as in a closed loop system, the system may monitor brain activity such as level of beta frequency activity and if the level of beta frequency activity is higher than a reference range (e.g., range reflective of a normal brain, such as, brain of a person not suffering from the disorder), the closed loop system may apply electrical stimulation to the Brodmann Area 11 and/or Brodmann Area 47 via an electrode positioned at or adjacent BA11 and/or BA47 in a manner effective to reduce the level of beta frequency activity (e.g., 13-30 Hz) in the brain of the subject.

Administration of a Pharmacological Agent

Embodiments of the methods and systems provided in this disclosure may also include administration of an effective amount of at least one pharmacological agent. By "effective amount" is meant a dosage sufficient to prevent or treat a neuropsychiatric disorder in a subject as desired. The effective amount will vary somewhat from subject to subject, and may depend upon factors such as the age and physical condition of the subject, severity of the neuropsychiatric disorder being treated, the duration of the treatment, the nature of any concurrent treatment, the form of the agent, the pharmaceutically acceptable carrier used if any, the route and method of delivery, and analogous factors within the knowledge and expertise of those skilled in the art. Appropriate dosages may be determined in accordance with routine pharmacological procedures known to those skilled in the art, as described in greater detail below.

If a pharmacological approach is employed in the treatment of a neuropsychiatric disorder, the specific nature and dosing schedule of the agent will vary depending on the particular nature of the disorder to be treated. Representative pharmacological agents that may find use in certain embodiments of the subject invention include, but are not limited to, Selective serotonin reuptake inhibitors (SSRIs) such as fluoxetine (Prozac), paroxetine (Paxil, Pexeva), sertraline (Zoloft), citalopram (Celexa) and escitalopram (Lexapro), Serotonin-norepinephrine reuptake inhibitors (SNRIs) (e.g., duloxetine (Cymbalta), venlafaxine (Effexor XR), desvenlafaxine (Pristiq, Khedezla) and levomilnacipran (Fetzima), and the like.

In certain aspects, the administration of a pharmacological agent involves using a pharmacological delivery device such as, but not limited to, pumps (implantable or external devices), epidural injectors, syringes or other injection apparatus, catheter and/or reservoir operatively associated with a catheter, etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert the at least one pharmacological agent into the delivery device for administration of the pharmacological agent to a subject and include, but are not limited to, vials, ampules, tubes, capsules, bottles, syringes and bags. Administration of a pharmacological agent may be performed by a user or by a closed loop system.

Systems

The present disclosure also provided systems which find use, e.g., in practicing the subject methods. Systems of the present disclosure may include a stimulation electrode adapted for positioning at Brodmann Area 11 and/or Brodmann Area 47 in orbitofrontal cortex region of brain of a subject in need of the methods provided herein. The system may further include a processor programmed to instruct the stimulation electrode to apply an electrical stimulation to the Brodmann Area 11 and/or Brodmann Area 47 in a manner effective to treat the neuropsychiatric disorder and/or ameliorate a symptom of the neuropsychiatric disorder in the subject.

The stimulation electrode may be an electrode or multiple electrodes, e.g., an electrode array, a surface electrode or a depth electrode. These electrodes are described in the sections above. Exemplary systems that include a stimulation electrode adapted for positioning at Brodmann Area 11 and/or Brodmann Area 47 in orbitofrontal cortex region of brain of a subject, a conductive lead connecting the electrodes to a pulse controller are depicted in FIGS. 1A and 1B.

The system may be an open-loop system for applying an electrical stimulation to the Brodmann Area 11 and/or Brodmann Area 47 to treat the neuropsychiatric disorder in the subject. The control unit of the system, based on pre-programmed parameters, or through manual control of the unit by a user, may direct electrical stimulation through a pulse generator and stimulation electrode. The control unit may interact with the pulse generator through a wired connection or through a wireless transmitter (e.g. RF transmitter located in the pulse generator). The pulse generator may be connected to the stimulation electrode(s) through a lead which may be implanted in the subject. The pulse generator may be an on-body unit or it may be a configured for attachment to the stimulation electrodes by a user.

In some cases, the system may be a closed-loop system configured for performing the methods provided herein. In some embodiments, the closed-loop system may include a stimulation electrode adapted for positioning at Brodmann Area 11 and/or Brodmann Area 47 in orbitofrontal cortex region of brain of the subject; a measurement electrode adapted for positioning at a secondary area of the brain and for recording an electrical signal from the secondary area during or after an electrical stimulation is applied to the Brodmann Area 11 and/or Brodmann Area 47; a computing means and control unit programmed to instruct the stimulation electrode to apply an electrical stimulation to the Brodmann Area 11 and/or Brodmann Area 47 in a manner effective to treat the neuropsychiatric disorder in the subject and/or ameliorate a symptom of the neuropsychiatric disorder (e.g., depression, anxiety, compulsive behavior, and the like); receive the electrical signal from the secondary area of the brain of the subject via the measurement electrode; apply the electrical signal metrics to a control algorithm that is tuned to a clinically relevant target (e.g., a range of signal indicative of effective treatment); modulate one or more programmed stimulation parameters according to the algorithm's control law; and apply the modulated electrical stimulation to the Brodmann Area 11 and/or Brodmann Area 47 via the control unit, pulse generator and stimulation electrode in a manner effective to treat the neuropsychiatric disorder. The closed loop system may include an on-body pulse generator that is connected to the implanted stimulation electrodes and hence can apply electric stimulation to the brain automatically upon receiving a communication from the control unit.

The processor of the closed-loop system may run programming to perform the steps required for assessing effectiveness of treatment and/or effectiveness of amelioration of a symptom of the neuropsychiatric disorder and modulate a parameter of the treatment as needed without user intervention. Thus the closed-loop system may not include a user interface for a user to instruct the stimulation electrode to apply an electrical stimulation to the Brodmann Area 11 and/or Brodmann Area 47 to treat the neuropsychiatric disorder in the subject. However, in some embodiments, a user interface may be included in the closed-loop system which may be used to confirm the recommendation of the closed loop system or to override it or to change the recommendation.

In certain aspects, a control algorithm for the methods and systems of the present disclosure may include steps of comparing electrical signal from a region of the brain of a subject to a normal or reference electrical signal, wherein when the electrical signal is significantly different from the normal or reference electrical signal, the control algorithm includes steps of directing a device to apply electrical stimulation to the brain of the subject, followed by measurement of electrical signal from the region of the brain and comparing it to a normal or reference electrical signal, where when the measured signal is significantly different from normal or reference electrical signal, the algorithm includes step of applying another electrical stimulation to the brain.

Components of systems for carrying out the presently disclosed methods are further described in the examples below.

Utility

The methods and systems of the present disclosure find use in a variety of different applications, including the treatment of neuropsychiatric conditions that affect mood and/or behavior of a person suffering from the conditions. Neuropsychiatric disorders that may be treated using the methods and systems presented herein include Major Depressive Disorder (MDD), Generalized Anxiety Disorder (GAD), Post-Traumatic Stress Disorder (PTSD), Addiction, Anorexia, Obsessive-Compulsive Disorder (OCD), Bipolar Disorder (BD) and chronic pain.

In certain aspects, the methods and systems of the present disclosure find use treating a subject suffering from a moderate to severe form of a neuropsychiatric conditions that affect mood and/or behavior of a person suffering from the conditions, for example the subject may be suffering from moderate or severe depression (e.g., Major Depressive Disorder (MDD) or treatment-resistant depression (TRD)), anxiety, addiction, anorexia, OCD, Bipolar Disorder (BD), chronic pain, or PTSD. In certain aspects, a subject may be suffering from a mild form of a neuropsychiatric disorder and may be treated according to the methods or using the systems of the present disclosure to treat the mild disorder and prevent progression into a more severe form.

In certain aspects, the methods and systems of the present disclosure may be used to treat chronic pain, such as one or more symptoms of chronic pain, e.g., constant attention to the experience of pain, emotional toll of the experience of constant pain, depression and/or anxiety. Efficacy of the treatment of patients suffering from chronic pain may be measured in an art accepted manner such as, by a Visual Analog Scale.

Open-loop intracranial stimulation of other brain targets, such as subcallosal cingulate gyms for MDD, and ventral capsule/ventral striatum or nucleus accumbens for OCD, have failed to show reliable effectiveness in normalizing low or anxious mood in controlled clinical trials. Based on the controlled study described here, OFC stimulation consistently improves mood and/or reduces anxiety in patients with symptoms of anxiety and/or depression. Moreover, based on the study findings, a range of anatomical locations within the OFC elicit positive mood effects, and both right and left OFC stimulation are effective. In contrast, the effectiveness or reliability of at least some other intracranial stimulation approaches for neuropsychiatric disorders appear to be sensitive to anatomical location of electrode placement.

OFC stimulation methods, including implantation of electrodes, are considerably less invasive than targeted ablation approaches. Furthermore, study results show that in examples of acute OFC stimulation, effect on mood state are similarly acute, indicating that the method represents a reversible intervention. This attribute offers the added advantages of (a) precise tuning of therapeutic stimulation to suit the needs of the patient and (b) the incorporation of OFC stimulation into well-controlled clinical trials featuring on/off periods and/or treatment crossover design.

OFC stimulation can be finely targeted and tuned in a personalized manner to achieve more reliable and/or more effective acute symptom relief compared to transcranial stimulation techniques. Likewise, these same attributes of targeting and tuning are more likely to impart neuroplastic change and lasting relief of disease symptoms than transcranial methods, given the ability to deliver considerably more precise stimulation paradigms through intracranial electrodes. The relatively greater precision and tunability of OFC stimulation methods has the potential to minimize side effects in individual patients. In addition, unlike transcranial methods, OFC stimulation does not require daily or near-daily in-clinic treatment regimens.

OFC stimulation methods consistently show effectiveness in alleviating symptoms of anxiety and depression in affected patients. In addition, OFC stimulation has the potential to be targeted and tuned in a personalized manner that may achieve more reliable and/or more effective symptom relief compared to less targeted peripheral interventions such as vagus nerve stimulation.

Cognitive behavioral therapies and pharmacologic interventions, for example with serotonin-reuptake inhibitors, are among the most established and widely implemented therapeutic approaches for neuropsychiatric disorders, though none has been demonstrated to effect reliable remission in all patients for any given indication. Notably, OFC stimulation presumably achieves its symptom-relieving effects through distinct mechanisms from those enacted by CBT or pharmacologic interventions. Hence, OFC stimulation represents a potentially complementary therapeutic modality that could be combined with CBT and/or pharmacologic treatment to optimize patient benefit.

Similarly, OFC stimulation methods may be optimized through the incorporation of complementary assessment techniques, including physiological and behavioral measures, performance on functionally relevant cognitive tasks, and patient-directed neurofeedback. Moreover, when integrated in real time, these assessment approaches can refine targeting and/or tuning of OFC stimulation and its therapeutic effectiveness.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for. Those of skill in the art will readily recognize a variety of noncritical parameters that could be changed or modified to yield essentially similar results.

Materials and Methods:

Experimental Design. The experimental protocol was approved by the Committee for Human Research at the University of California, San Francisco. Written informed consent was obtained from all subjects. Subjects (N=21, 11 males, ages 20-60) had been diagnosed with drug-resistant epilepsy and were undergoing intracranial electroencephalography (iEEG) for seizure localization. Subjects were included in the study if they had electrodes implanted in brain regions of interest and were willing and able to cooperate with study tasks. Subjects were excluded if they lacked capacity or declined to provide informed consent, did not have electrodes implanted in regions of interest, had significant cerebral lesions, and/or had cognitive deficits that precluded reliable completion of study tasks. Electrode implantation was guided solely by clinical indications and therefore varied somewhat across subjects, but electrodes typically sampled multiple sites implicated in mood regulation, including OFC, amygdala, hippocampus, insula, and cingulate cortex. Due to limited time windows for testing, subject tolerance, and other constraints related to the inpatient environment, it was not possible to perform all experiments in all subjects.

Subdural grid, strip, and depth electrodes (AdTech, Racine, WI, or Integra, Plainsboro, NJ) were implanted using standard neurosurgical techniques. Subjects underwent pre-operative 3 Tesla brain magnetic resonance imaging (MRI) protocols, including T1 and High Angular Resolution Diffusion Imaging (HARDI; B=2000, 55 directions) sequences, and post-operative computed tomography (CT) scan to localize electrodes. Electrode locations were visualized by co-registering pre-operative T1 images with the post-operative CT using Statistical Parametric Mapping software SPM12 (J. Ashburner, et al. *Neuroimage* 6, 209-217 (1997)). Pial surface 3D reconstructions were created using FreeSurfer (B. Fischl, FreeSurfer. *Neuroimage* 62, 774-781 (2012)).

Prior to electrode implantation, subjects underwent neuropsychological testing that typically included the Beck Depression Inventory II (BDI) (A. T. Beck, et al., *J Pers Assess* 67, 588-597 (1996)) and Beck Anxiety Inventory (BAI) (A. T. Beck, et al., *J Consult Clin Psychol* 56, 893-897 (1988).). BDI and BAI scores, which ranged from minimal to severe (FIG. 25A), established baseline mood trait and were binned into two categories (minimal-mild and moderate-severe), based on clinically established cutoff values, to facilitate analysis (A. T. Beck, et al., Manual for the Beck Depression Inventory-II. Psychological Corporation, San Antonio, TX (1996); A. T. Beck, R. A. Steer, Beck Anxiety Inventory Manual. Psychological Corporation, San Antonio, TX (1993)). In two subjects for whom BDI and BAI scores were not available, Patient Health Questionnaire-9 (PHQ-9) (K. Kroenke, et al., *J Gen Intern Med* 16, 606-613 (2001)) and Generalized Anxiety Disorder-7 (GAD-7) (R. L. Spitzer, et al., *Arch Intern* Med 166, 1092-1097 (2006)) scales were used to determine mood trait categorization.

Following electrode implantation, subjects used a validated tablet-based mood tracking application, the Immediate Mood Scaler (IMS) (M. Nahum, et al., *JMIR Mhealth Uhealth* 5, e44 (2017)), which enables momentary assessment of a multidimensional set of symptoms related to depression and anxiety and thus operationally defines mood state. IMS measurements of mood state were collected serially multiple times a day over several days prior to brain stimulation.

Figure 24A:
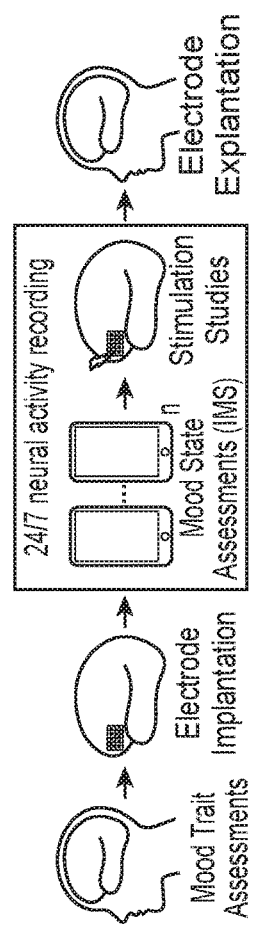
FIGS. 24A-24C depict experimental design and locations of stimulated sites.
Figure 24C:
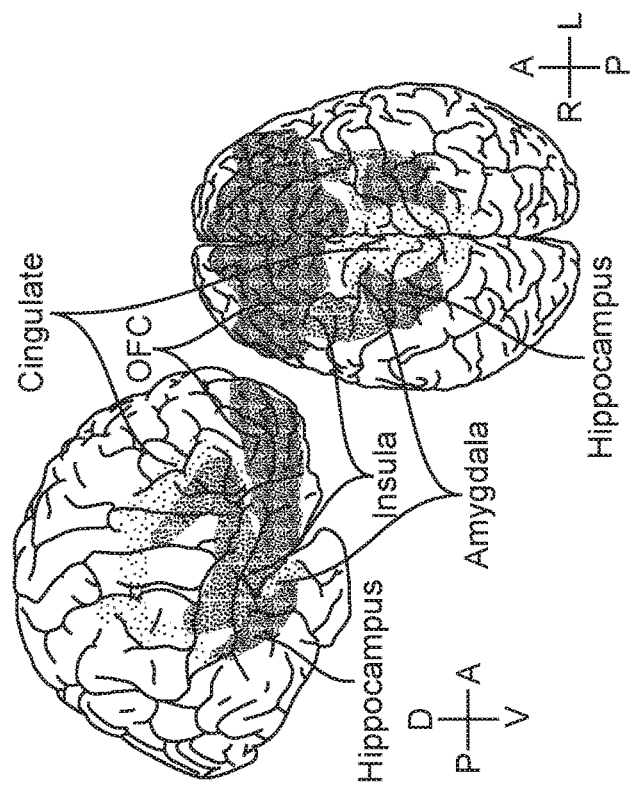
Figure 24B:
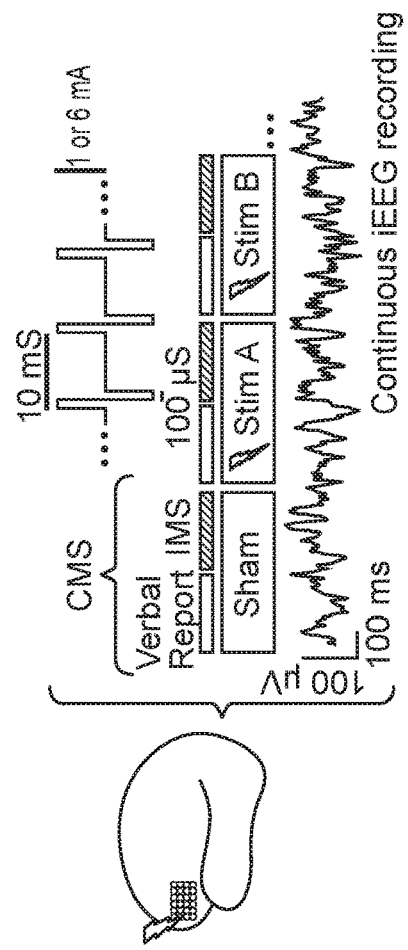

For stimulation studies, sham (0 mA) stimulation blocks allowed subjects to serve as their own controls. Due to the idiosyncratic nature of mood self-reports, quantification of stimulation effects on mood state has not been standardized (K. S. Choi, et al., *JAMA Neurol* 72, 1252-1260 (2015)). However, the IMS was specifically developed to capture a range of mood states in the context of clinical interventions (M. Nahum, et al., supra). To make mood state assessment during stimulation as quantitative and sensitive as possible, we employed a combination of verbal report and IMS (FIG. 24B).

Mood Assessment. Verbal report consisted of subjects' responses to open-ended questions regarding their current mood. Subjects were prompted to freely articulate their current mood state over the course of approximately 30 sec at the beginning of each stimulation block. Audiovisual recordings of experimental sessions were transcribed by researchers blind to stimulation condition. Transcribed reports were analyzed for positive and negative words using the validated Language Inquiry Word Count (LIWC) software (*The development and psychometric properties of LIWC2015* (2015)). A word valence ratio score was calculated and normalized on a scale from 0 (completely negative word use) to 100 (completely positive word use) based on the number of positive emotion words ($N_+$) and the number of negative emotion words ($N_-$):

$$\frac{N_+ - N_-}{N_+ + N_-} \times 100$$

Word valence scores were excluded if there was a change of 50 points or more and transcripts did not reveal sentiment to justify this large change.

Immediately after verbal mood report, subjects answered IMS questions on a tablet. Questions involved seven buttons spanning a pair of negative and positive mood-state descriptor words. Subjects tapped the button that best reflected current mood state, with the middle button corresponding to a neutral mood state for the pair of words. IMS scores for each stimulation block were normalized on a 0 to 100 scale. IMS and word valence scores from verbal reports were averaged to obtain a Composite Mood Score (CMS), which served as the primary readout of stimulation-induced mood state changes (higher CMS indicates more positive mood). If either word valence score or IMS was not available, one score was used in place of CMS.

Behavioral Analysis. To determine whether mood state changed during stimulation, we assessed change in CMS (stim-sham) using one-sample t-tests, two-sample t-tests, and factorial ANOVA. Each stimulation condition (1 mA, 6 mA) was tested separately using a one-sample t-test to assess if the changes in CMS were significantly different from zero. Two-sample t-tests were used to compare effects of 1 mA and 6 mA stimulation. To determine if effects of stimulation on CMS differed based on mood trait scores, we performed a factorial ANOVA with independent variables Trait (minimal-mild or moderate-severe) and *Stimulation-Amplitude* (1 or 6 mA) and the interaction between *Trait and Stimulation Amplitude*.

Speech Rate Analysis. Video and audio from the stimulation experiments were analyzed for potential effects on speech rate during sham and active stimulation blocks. Subjects' verbal reports were transcribed by blinded researchers and each sentence spoken was timed. Lulls in speech greater than 2 sec were not included in the overall time of the sentence. The total number of words for all sentences was divided by the total time of speaking during verbal report to give a speech rate in words per second.

Electrode Stimulation. Brain stimulation was performed in the window of time after collection of clinical seizure data was completed and before electrode explantation. Typically, anticonvulsant medications that had been tapered to provoke seizures, per standard clinical protocols, were restarted prior to stimulation experiments. Stimulation was performed using the manually-operated Nicolet™ Cortical Stimulator (Natus Medical, Inc., Pleasanton, CA), which delivers biphasic, constant-current trains of stimulation pulses, and monitored using the Natus EEG viewing software. For continuous stimulation of OFC and other regions, parameters were: 1-6 mA, 100 Hz, 100 µs pulse width, 100-200 sec duration. For single-pulse stimulation (SPS), parameters were: 10 mA, 1 Hz, 500 µs pulse width, 20 sec duration. A board-certified epileptologist (V.R.R.) monitored iEEG recordings in real-time for stimulation-induced after discharges and electrographic seizures, which did not occur with OFC stimulation.

Diffusion Tractography. Datasets were corrected for motion and eddy current distortion using the Functional Magnetic Resonance Imaging of the Brain (FMRIB) Software Library (FSL) (M. Jenkinson, et al., *Neuroimage* 62, 782-790 (2012)) and the gradient table rotated (A. Leemans, D. K. Jones, *Magn Reson Med* 61, 1336-1349 (2009)). A tensor model was fit to the corrected high angular resolution diffusion imaging (HARDI) data using the open-source package Diffusion Imaging in Python (Dipy) (E. Garyfallidis, et al., *Front Neuroinform* 8, 8 (2014)) and the resulting parameters were used to calculate tensor metrics. An Anisotropic Power Map (APM) (K. Mi, *Exp Ther Med* 12, 2371-2376 (2016)) was calculated using the Q-ball model (120) implemented in Dipy. This diffusion-derived image can be used to perform a better registration to the T1 space than fractional anisotropy (B. S. Fernandes, et al., *BMC Med* 15, 80 (2017)). The BO image was used to create a brain mask by skull-stripping the image with FSL's Brain Extraction Tool (BET) (S. M. Smith, *Hum Brain Mapp* 17, 143-155 (2002)), and this brain mask was applied to all images.

For each subject, a diffeomorphic registration was performed to align the APM and the T1 image and to transfer the electrodes from the T1 image to diffusion space using the Advanced Normalization Tools (ANTs) (B. B. Avants, et al., *Neuroimage* 54, 2033-2044 (2011)) implemented in Dipy. The registrations and the point transformation to diffusion space was manually quality-controlled by comparison to cortical anatomy. Trackvis (at trackvis.org) was used to visualize results. Using custom Python software, the white matter voxel nearest to the midpoint between the positive and negative bipolar electrodes was identified. Using Trackvis, a human operator expanded a sphere centered on this midpoint white matter voxel until the first streamline was targeted. This point in space was selected as the center of the stimulation ROI, a uniform 10-mm radius sphere used to generate streamline connectivity profiles in each subject. This procedure ensured that the most likely white matter connections serving the cortical regions was represented in each subject. Streamlines shorter than 40-mm were excluded.

Residual bootstrap probabilistic q-ball tractography (J. I. Berman, et al., *Neuroimage* 39, 215-222 (2008) was performed from the stimulation ROI. Principal fiber orientation was estimated at each step by computing a bootstrapped orientation distribution function (ODF) and identifying the peaks, as described previously (S. E. Hyman, Revolution stalled. *Sci Transl Med* 4, 155 cm111 (2012)). The principal fiber orientations from the ODFs provided the distribution of fiber tracking directions. Tracking was seeded uniformly at a density of $7^3$ seeds per voxel and terminated by the following criteria: FA threshold of 0.15 and maximum angle of 60° (M. Bucci, et al. *Neuroimage Clin* 3, 361-368 (2013)).

To generate the group results on a Montreal Neurological Institute (MNI) template, a diffeomorphic registration was performed between the APM and MNI template using ANTs. The streamline dataset representing the connectivity of each subject was binarized such that each voxel containing at least one streamline was included in the binary mask. The diffeomorphic diffusion-to-MNI transformation was applied to the binarized masks so that they could be summed in the common MNI space to produce heat maps that represent the spatial overlap between white matter connectivity in multiple subjects. This analysis was performed to show the connectivity of the group with the left hemispheric electrodes (blue-green) and right hemispheric electrodes (pink-yellow) summed independently.

Data Acquisition and Signal Processing. iEEG recordings were acquired at sampling rates ranging from 1 kHz to 16 kHz using the Natus EEG clinical recording system. Offline analysis was conducted using custom scripts in MATLAB (Mathworks, Inc., Natick, MA). Standard iEEG pre-processing was combined with artifact rejection methods to enable analysis of spectral activity during electrical stimulation. Artifact rejection allowed for analysis of lower frequencies (<40 Hz), but higher frequencies could not be analyzed because artifact rejection procedures change spectral characteristics of the signal in frequencies around the stimulation frequency. Artifact rejection could only be conducted on data acquired at 8192 Hz or greater because of the high stimulation frequency (different sampling rates not systematically assessed). The times including stimulation artifact were identified and deleted, and cubic spline interpolation was applied from 0.7-0.8 ms before the artifact peak to 1.5-3 ms after the artifact peak; times were chosen empirically based on inspection of signals. Additional pre-processing steps included application of a [2 to 250 Hz] bandpass filter, rejection of channels with high noise or multiple bouts of large amplitude artifacts, common average referencing to the mean of all channels remaining after channel rejection, application of notch filters at line noise frequency and harmonics (60 Hz, 120 Hz, 180 Hz, 240 Hz) and stimulation frequency and harmonic (100 Hz, 200 Hz), manual rejection of time periods with non-physiological synchronized activity across channels, and downsampling to 512 Hz. Only electrode contacts located in the target region of interest (verified by visual review of MRI and CT) were analyzed.

To determine whether (1) OFC power correlated with mood, and (2) stimulation altered spectral iEEG activity, power was extracted from each electrode by filtering the pre-processed data in frequency bins with logarithmically increasing center frequencies and applying the Hilbert transform. In cases where multiple electrodes were positioned in the region of interest, power was averaged across these electrodes. Where specified, power was averaged within standard frequency bands (theta=4-8 Hz, alpha=8-12 Hz, beta=13-30 Hz, gamma=30-55 Hz, high gamma=65-100 Hz; because of artifact rejection procedures, gamma and high gamma activity were only assessed for iEEG power correlations with mood).

We tested if OFC power co-varied with mood using Bonferroni-corrected Pearson's correlation coefficient between OFC power and IMS scores. Specifically, iEEG data were extracted 2 min before and after each IMS point. Data were pre-processed and log power was calculated for standard frequency bands. IMS scores and neural activity metrics were first z-scored within each subject to account for each individual's range of responses, and then combined across subjects. Multiple comparisons were controlled for using Bonferroni correction (5 frequency bands tested, thus correlations significant if $p<0.01$). Subjects with fewer than 2 IMS points were excluded, and IMS points tested during stimulation experiments were excluded.

We assessed the effects of OFC stimulation on power in standard frequency bands by calculating percent change in power from before stimulation (pre-stim) to during stimulation (stim), and from during stimulation to after stimulation (post-stim). Power was averaged across relevant time periods (pre-stim, stim, and post-stim time periods were 43.8±30.7, 193.5±97.8, and 83.1±48.5 (mean±SD) [seconds], respectively) and averaged within frequency bands. For visualization in spectrograms only, power was z-scored relative to pre-stim period. A one-sample t-test was used to test if change score was significantly different from zero. Significance was established for p-values<0.05.

In some subjects, SPS was administered before and after continuous OFC stimulation. Pre-processing steps included removing data surrounding stimulation artifact peaks [−5 to 10] ms, application of a [1 to 100 Hz] bandpass filter, and notch filter at line noise frequency (60 Hz). For each stimulation pulse, evoked activity was z-scored relative to a trial-specific pre-pulse baseline [−300 to −100] ms, the signal was rectified, and the maximum peak was extracted from [13 to 200] ms following the stimulation artifact peak. Significance was assessed with a paired t-test.

Statistical Analyses—Described in the corresponding methodological sections above.

Example 1: Schematic for Electrical Stimulation of OFC Region of Brain

Figure 5A:
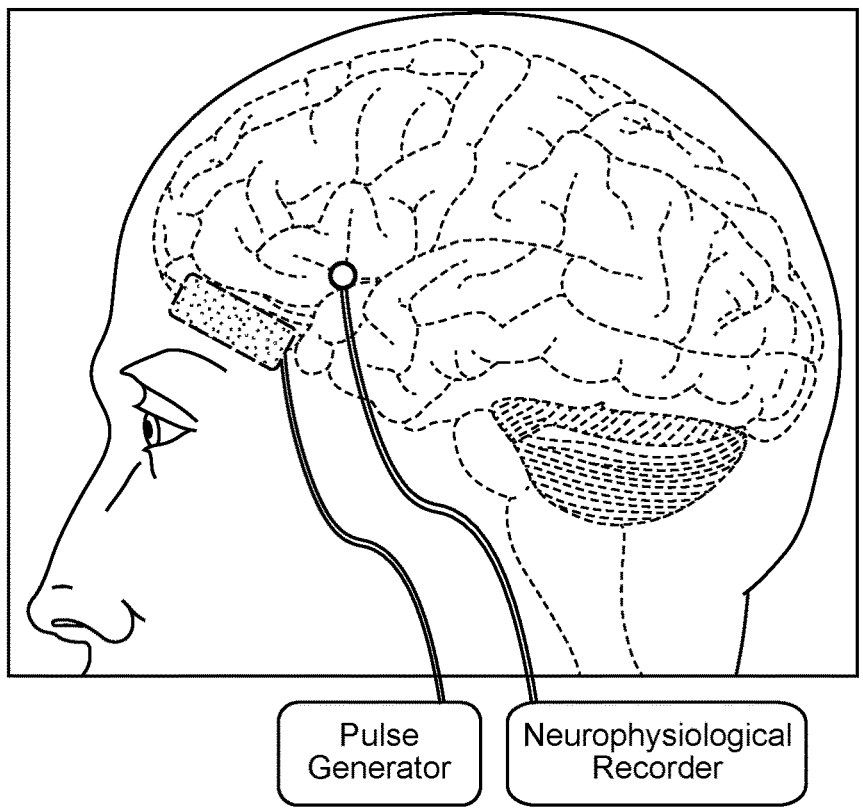
FIGS. 5A and 5B illustrate schematics for the stimulation of the OFC region using a surface electrode array (FIG. 5A) or a depth electrode array (FIG. 5B). Also depicted is a pulse generator and an implantable lead for activating the electrodes and a neurophysiological recorder for recording brain activity from an area adjacent to the location of the stimulation electrodes.
Figure 5B:
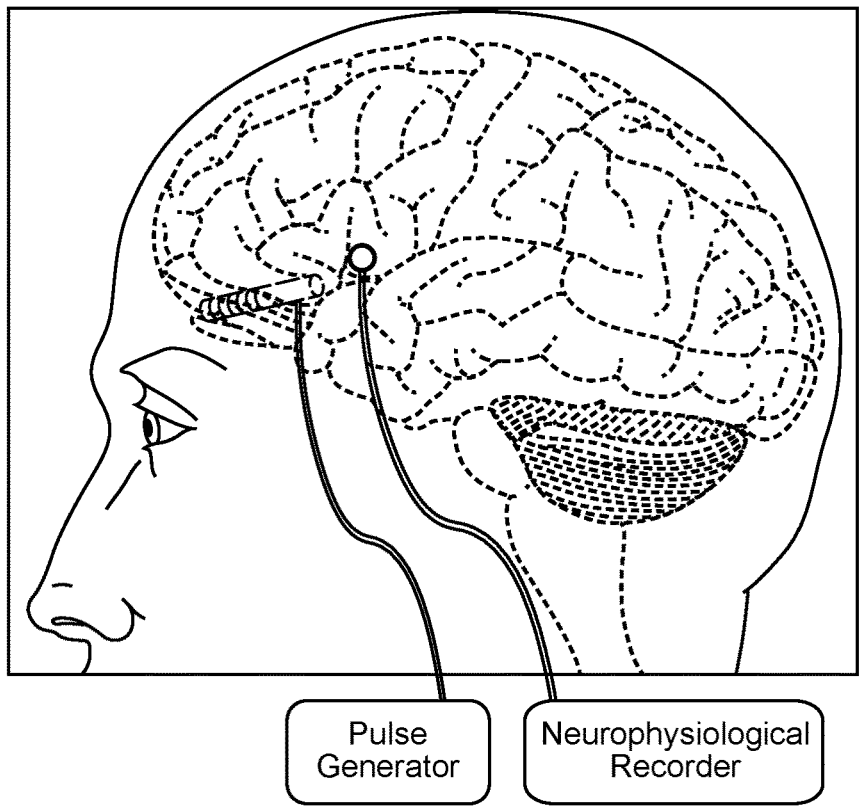
Figure 6A:
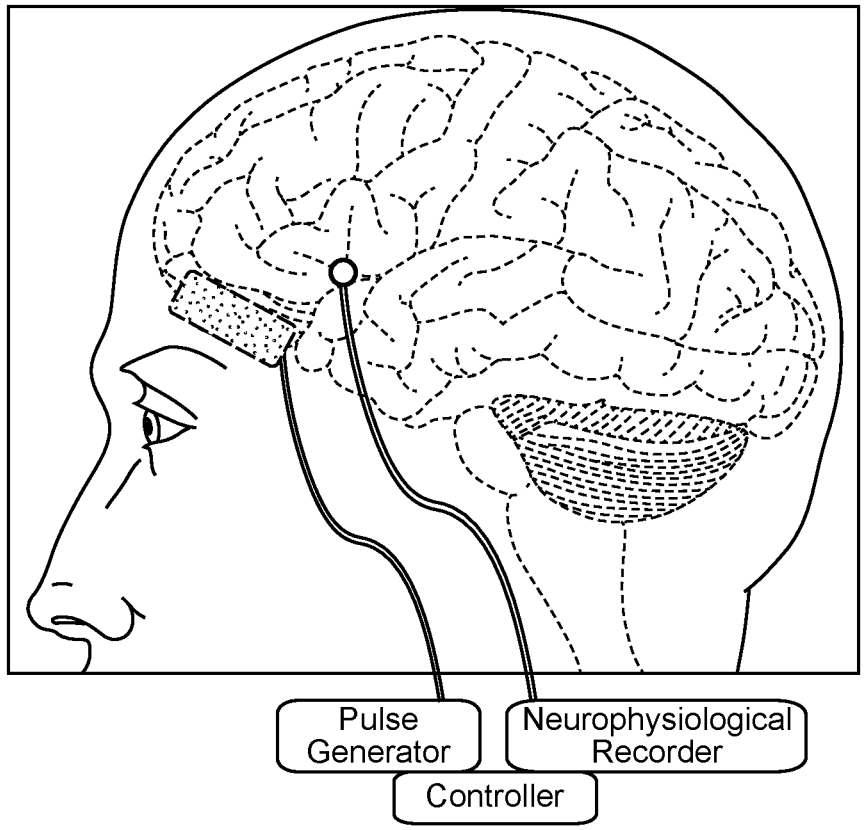
FIGS. 6A and 6B illustrate a closed-loop system for stimulation of the OFC region with a configuration including a pulse generator, implantable leads, electrode(s), neurophysiological recorder and controller.
Figure 6B:
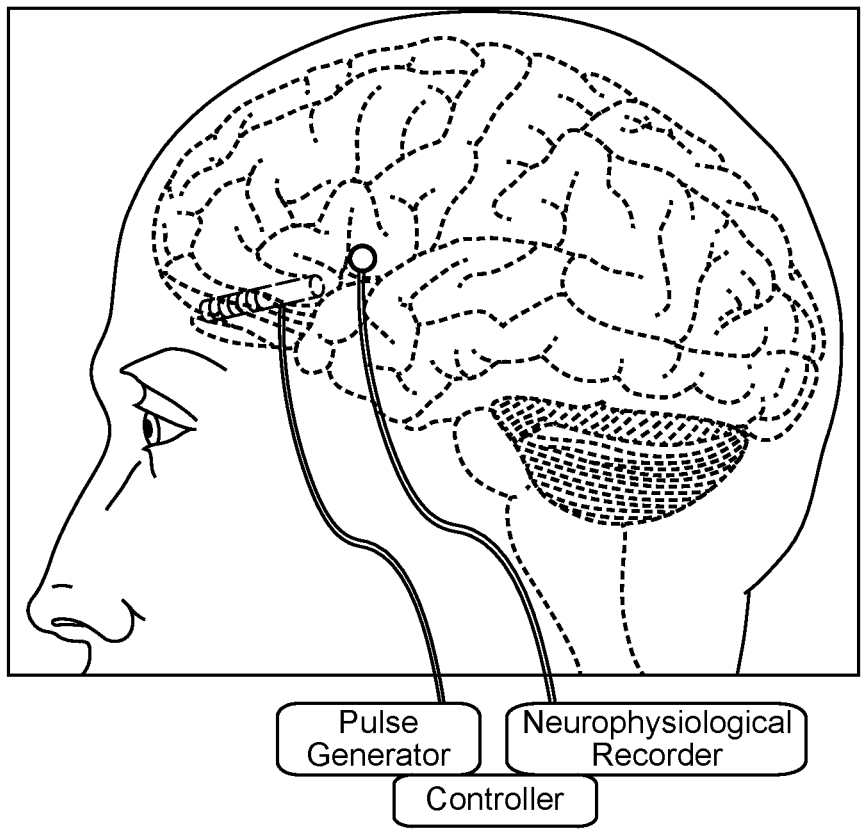

FIG. 1 shows lateral views of the brain surface with a surface electrode array (FIG. 1A) or a depth electrode array (FIG. 1B) placed within the OFC region. The electrodes may apply electrical stimulation to a site or sites within the OFC region and its immediate surroundings. The parameter of the stimulation is set to effect changes in physiological activity in neural networks related to the etiology or symptomatology of neuropsychiatric disorders. Under this method, the electrical stimulation is provided by a pulse generator connected via implantable leads to an electrode or electrodes in contact with the brain. Schematic depictions of such pulse generator/lead/electrode arrangements are shown in FIGS. 2A and 2B. Schematic depictions of the OFC region are shown in FIGS. 3A, 3B, and 3C and in FIGS. 4A and 4B. Schematic depictions of generator/lead/electrode/controller arrangements capable of delivering programmed stimulation to the OFC region in the absence of real-time neurophysiological feedback (open-loop stimulation) or in the presence of real-time neurophysiological feedback (closed-loop stimulation) are shown in FIG. 5 and FIG. 6, respectively.

Example 2: A Step-Wise System for Therapeutic Application of OFC Stimulation

Figure 7:
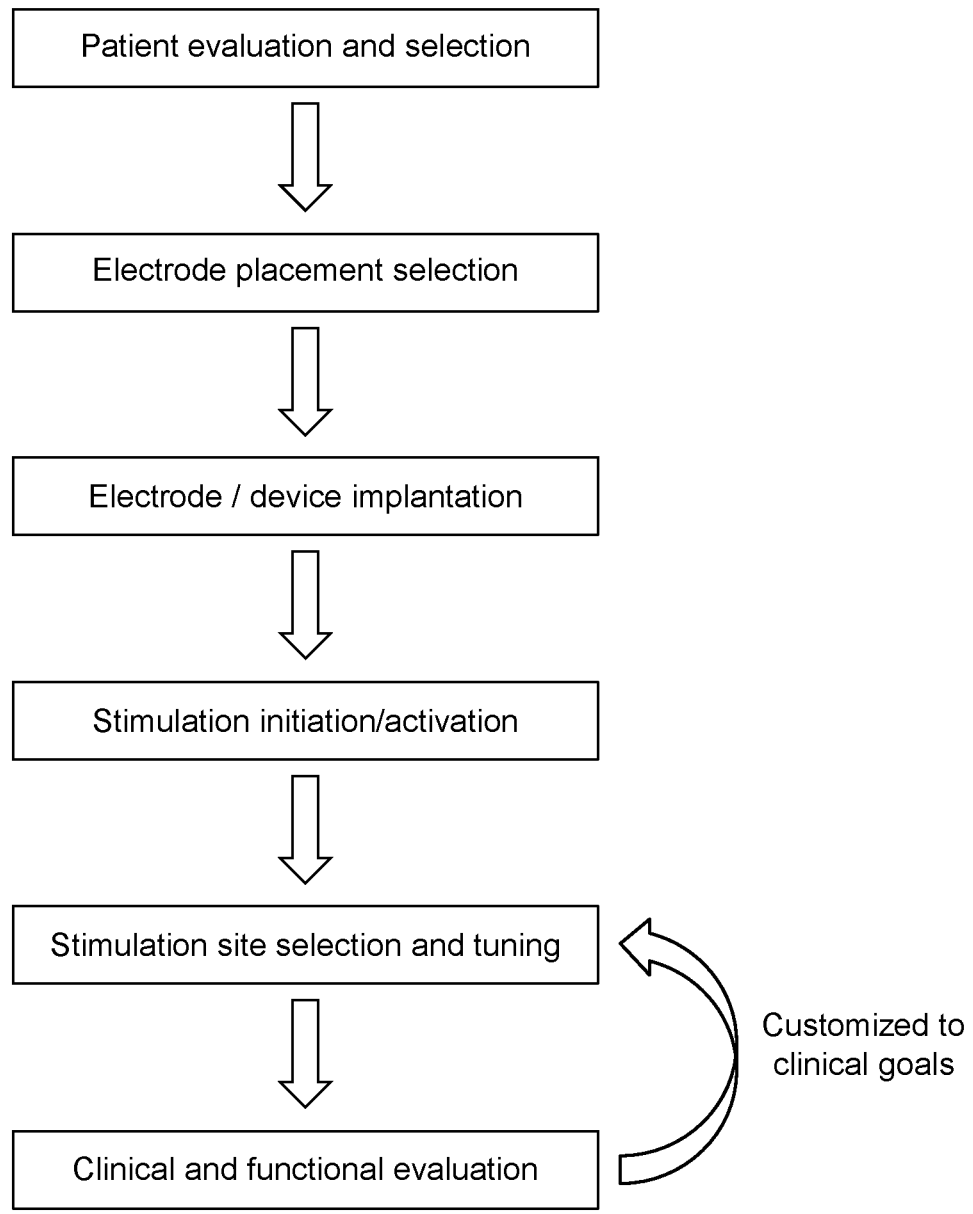
FIG. 7 illustrates a flow chart for an exemplary method for treatment of affective neuropsychiatric disorders.

Examples of therapeutic application of OFC stimulation are described below. These and related applications may be utilized in the context of a clinical system for the treatment of neuropsychiatric disorders. FIG. 7 shows the steps performed in this system. In the first step, a patient is evaluated for need for OFC stimulation-based treatment, on the basis of a number of assessments including clinical neuropsychiatric assessments, cognitive assessments, measures of anatomical, biophysical, and/or functional brain features and/or connectivity, and other related evaluations. In the second step, patients selected for treatment are evaluated for electrode placement on the basis of the preceding assessments and related measures. In the third step, patients undergo electrode and/or electrode-integrated stimulation device implantation. This step may include a tailored electrode configuration for OFC recordings (tailored array shape, electrode number, electrode size, and/or electrode spacing). In the fourth step, patients undergo initial activation of OFC stimulation, alone or in combination with stimulation of other brain areas, for example via an electrode-integrated stimulation device. This step may involve open-loop system-identification procedures to evaluate parameters for open- and closed-loop stimulation, for example through the characterization of input-output relationships and/or transformation functions that relate OFC stimulation to recordings in other brain areas. In the fifth and sixth steps, stimulation site(s) are selected and open- and/or closed-loop stimulation parameters and configurations are tuned on the basis of therapeutic, functional/behavioral and/or neurophysiological measures, potentially including quantitative and/or qualitative self-report of symptoms, performance on cognitive tasks, effects of stimulation on the neurophysiological state of relevant brain circuitry, effects on relevant neural biomarkers, or the like. Through the use of an array of effect measures such as the foregoing, especially those involving neurophysiological recording, a rational and directed approach to paramerization is possible that includes testing a wide variety of stimulation conditions. Steps five and six are repeated as necessary to optimize safety and therapeutic effectiveness.

Example 3: Open-Loop Stimulation for Symptom Relief

In the example shown in FIG. 1A, stimulation is delivered to at least one electrode (aka contact) located on the surface of the OFC, with electrodes configured individually or as part of a strip or surface array (as shown); in the example in FIG. 1B, stimulation is delivered to at least one electrode located within the OFC and under the cortical surface, with electrode or electrodes configured as part of a depth electrode array. In both the surface-electrode and depth-electrode configurations, stimulation is delivered from the pulse generator, continuously, periodically or intermittently, with the purpose of alleviating or preventing further neurophysiological disease symptoms. In this example, stimulation is performed in an "open loop," under a regimen or set of parameters that is not automatically modified by the neurophysiological brain state.

In this example, as depicted in FIG. 8, stimulation may be delivered to provide acute alleviation of disease symptoms and/or chronic relief or prevention of disease symptoms. Based on study observations cited below, effective stimulation parameters might be found at or near values of about 25 Hz-500 Hz frequency (e.g., about 50-150 Hz, such as, 100 Hz frequency), 1 mA-30 mA (e.g., about 3-6 mA) current, and 10 μs-1 msec (e.g., about 75-125 μs, such as, 100 μs) pulse width, applied continuously for a period of about 1 min-30 min (e.g., about 5 min-15 min, such as, 10 min). Likewise, various stimulation methodologies and configurations may be found effective in the case of this example, and potentially include single-site or multi-site stimulation, either solely within the OFC or inclusive of additional brain areas; un-patterned or patterned stimulation; surface and/or depth electrodes used individually or in combination; stimulation delivered unilaterally or bilaterally; and related variations.

The above variations in parameterization and configuration of OFC stimulation may also be applied to the examples given below.

Figure 9:
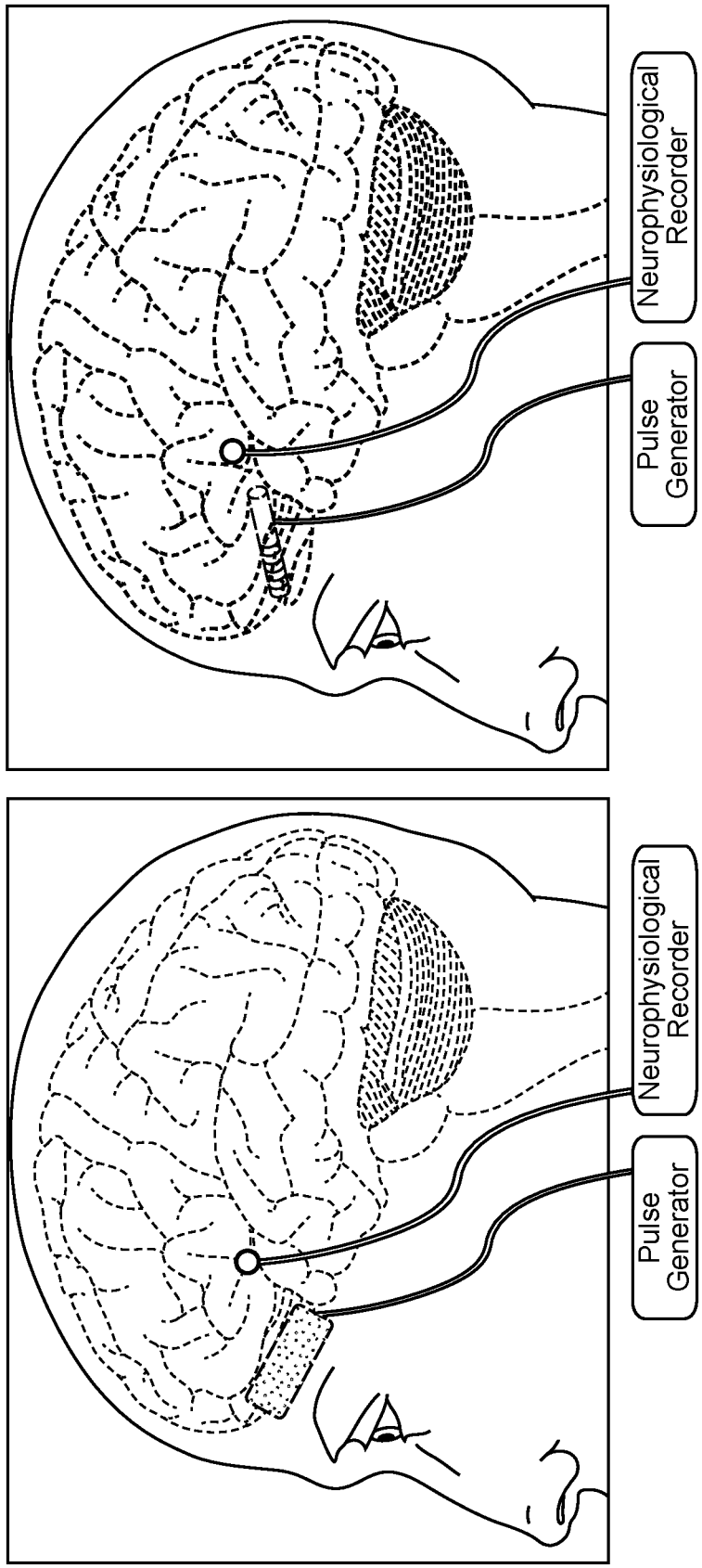
FIG. 9 depicts device configurations and a process for open-loop OFC stimulation to achieve symptom control, in combination with neural recording.
Figure 9:
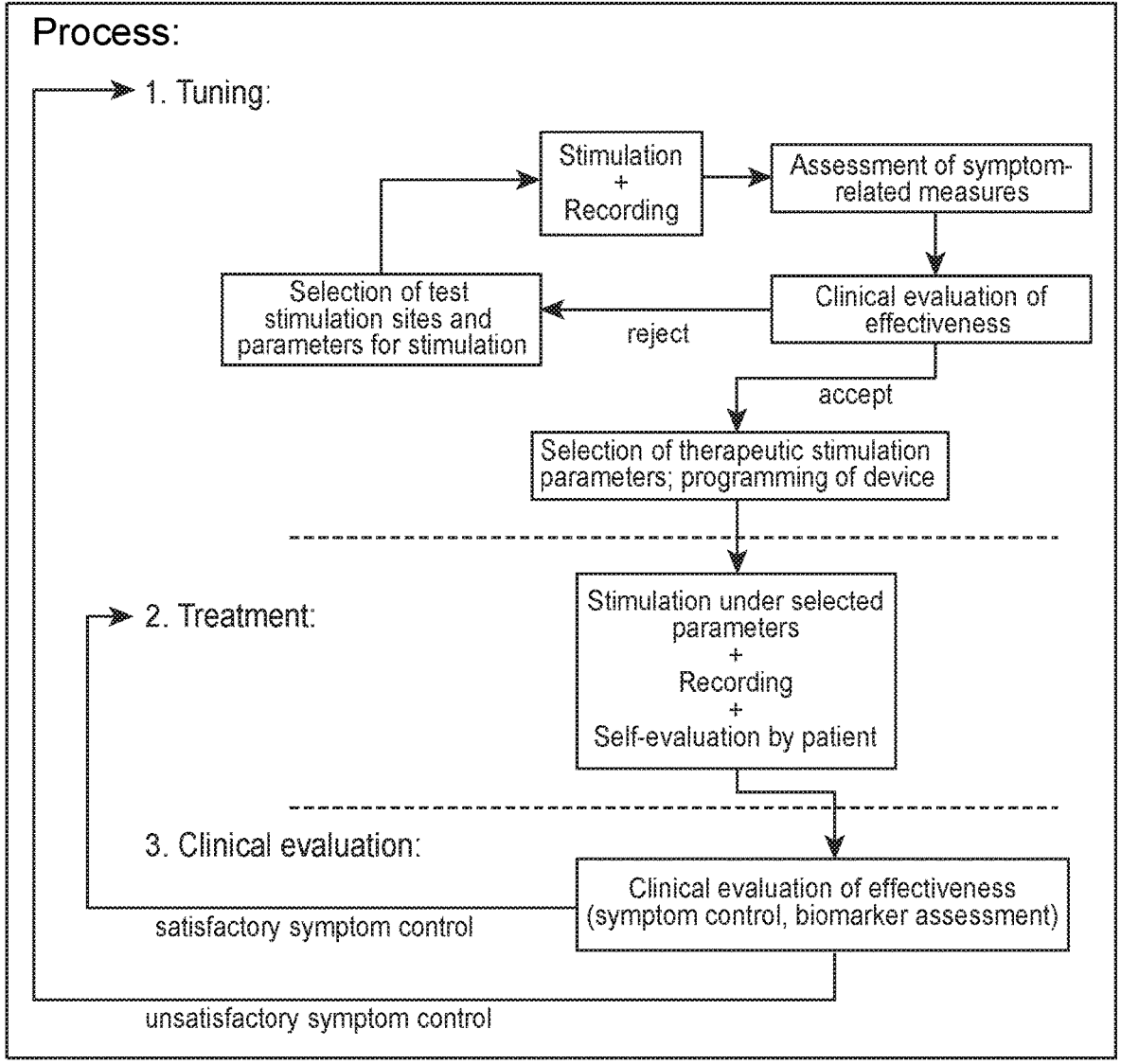

Example 4: Open-Loop Stimulation for Symptom Relief, in Combination with Recording In another example, open-loop stimulation is delivered to the OFC to provide acute alleviation of neuropsychiatric disease symptoms and/or chronic relief or prevention of disease symptoms, as described above with the exception that a neurophysiological recording device is employed in conjunction with the pulse generator to allow recording of brain activity to track and assess brain state and/or the effects of therapeutic stimulation. FIG. 9A shows schematic depictions of a surface electrode array and a depth electrode array in a stimulation-recording configuration. In this example, a stimulation program is originated by the pulse generator and delivered to the OFC region through an electrode or electrodes in contact with the brain and connected to the generator by an implantable lead. Concurrently, a recording electrode or electrodes, located at the OFC and/or in other brain regions, senses site-specific neurophysiological activity and transmits these electrical signals to a neurophysiological recorder that is connected to the electrodes via an implantable lead. As depicted in FIG. 9B, these signals are in turn transmitted to clinicians and/or researchers to provide information about the patient's neurophysiological brain state, dependent or independent of stimulation, that may be useful for clinical assessment and/or treatment planning.

Example 5: Closed-Loop Stimulation for Symptom Relief

In another example, stimulation is delivered to the OFC to provide acute alleviation of neuropsychiatric disease symptoms and/or chronic relief or prevention of disease symptoms, as described above with the exception that stimulation is performed in a closed loop, wherein stimulation parameters are automatically modified by the neurophysiological brain state. In this example, a neurophysiological recording device provides data representing the neurophysiological brain state to a controller device, which employs a control algorithm to provide modulatory feedback to the pulse generator. In this way, stimulation to the OFC is delivered in a fashion that is adaptive to clinically-relevant brain states. FIG. 10A shows schematic depictions of a surface electrode array and a depth electrode array in closed-loop configurations. In this example, a stimulation program is originated by the pulse generator and delivered to the OFC region through an electrode or electrodes in contact with the brain and connected to the generator by an implantable lead. Concurrently, a recording electrode or electrodes, located within the OFC and/or in other brain regions, senses site-specific neurophysiological activity and transmits these electrical signals to a neurophysiological recorder that is connected to the electrodes via an implantable lead. These signals are in turn transmitted to a controller device that is programmed to output a modulatory signal to the pulse generator based on a control algorithm. Thus, parameters of stimulation within the OFC, alone or in combination with stimulation at other sites, are updated in response to the brain state at a given time. FIG. 10B depicts a process whereby closed-loop OFC stimulation is clinically employed for symptom relief.

Figure 11:
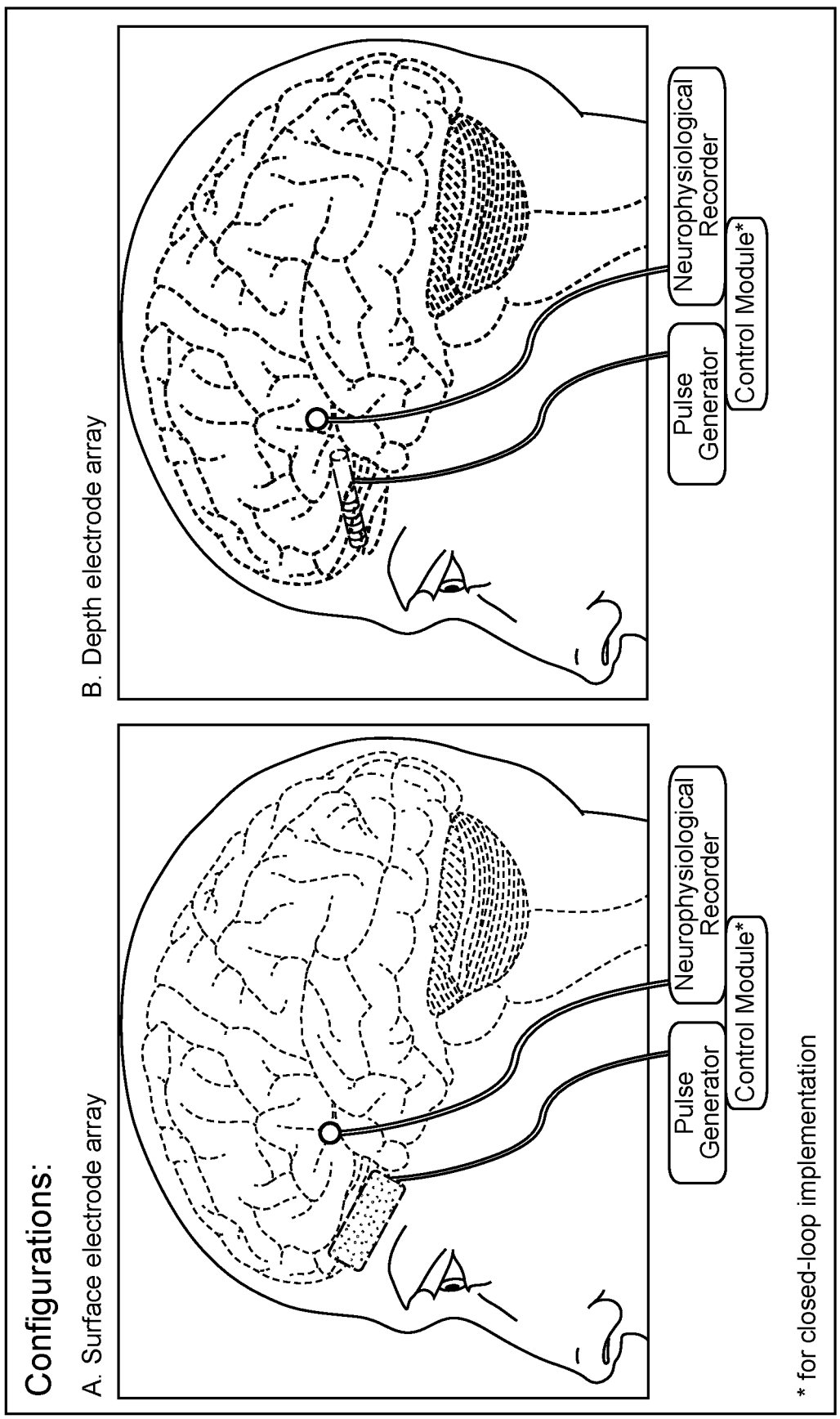
FIG. 11 depicts device configurations and a process for open- or closed-loop OFC stimulation to achieve lasting symptom control via neuroplastic change.
Figure 11:
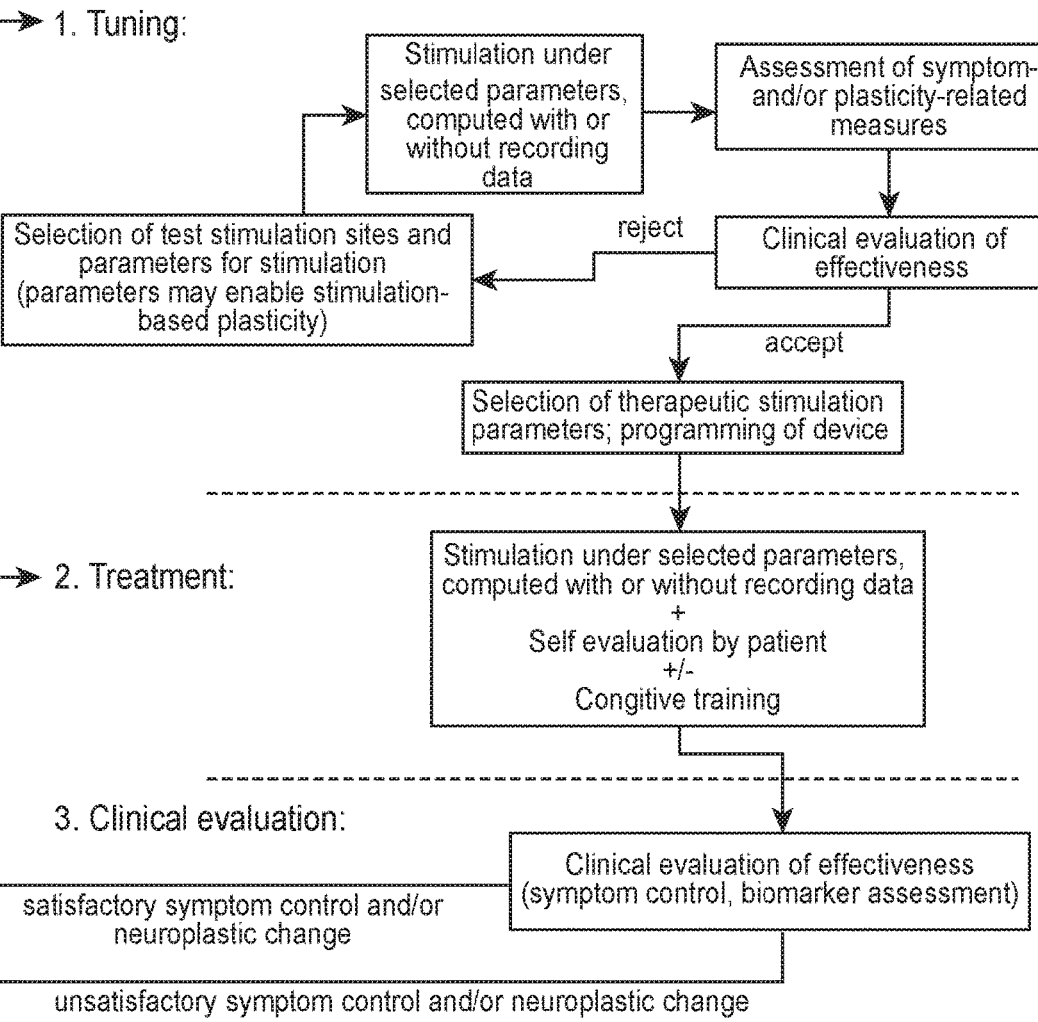

Example 6: Open- or Closed-Loop Stimulation for Effecting Neuroplastic Change for Lasting Resolution of Symptoms In another example, stimulation is delivered to the OFC to provide neuromodulation or neuroplastic change that results in lasting resolution of neuropsychiatric disease symptoms. Using approaches described above for open-loop and closed-loop stimulation, stimulation parameters and configurations are employed with the goal of using OFC stimulation to direct lasting plastic change in disease-relevant circuitry. In this example, OFC stimulation, alone or in combination with stimulation in other brain areas, may be used to generally promote plasticity in a circuit or circuits that are subsequently modulated through cognitive training, with the effect of potentiating and/or accelerating training-based strengthening (learning) of adaptive neural activity patterns and/or weakening (unlearning) of maladaptive neural activity patterns. Alternatively, OFC stimulation, alone or in combination with stimulation in other brain areas, may be used to directly enact stimulation-driven neuroplasticity, for example through Hebbian or non-Hebbian mechanisms of spike-timing-dependent-plasticity and/or state-dependent induced plasticity. The goal of such stimulation would be to directly strengthen, weaken, or otherwise modulate or modify the behavior, activity, and/or function of disease-relevant circuitry so as to provide lasting resolution of neuropsychiatric symptoms. In this example, as depicted in FIG. 11, stimulation-enabled neuroplastic change could be achieved through stimulation of OFC in open- or closed-loop paradigms.

Figure 12:
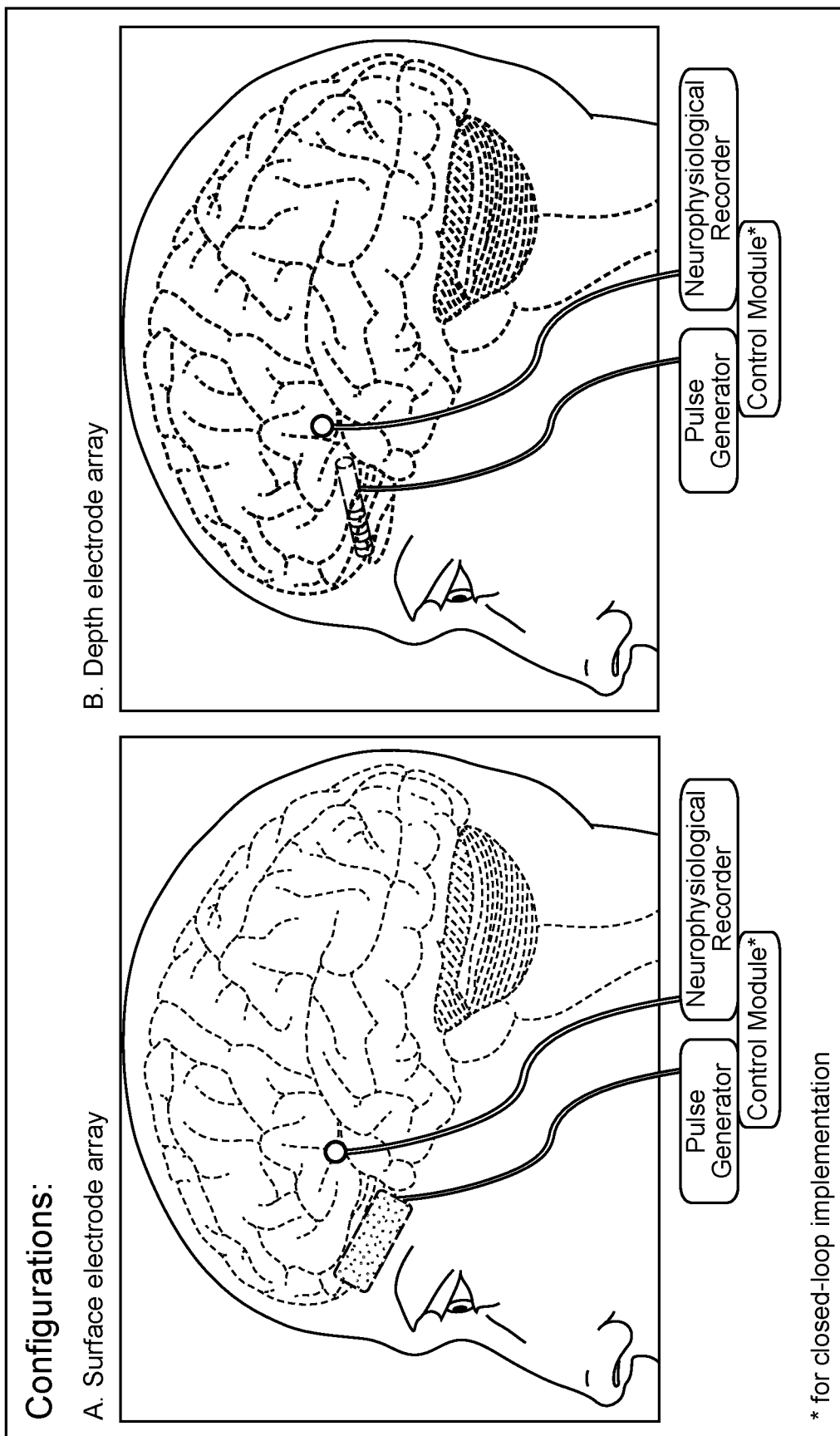
FIG. 12 depicts device configurations and a process for open- or closed-loop OFC stimulation to evaluate candidate biomarkers of symptoms or disease.

Example 7: Open- or Closed-Loop Stimulation to Evaluate the Clinical Relevance of Candidate Biomarkers of Symptoms or Disease In another example, candidate biomarkers of symptoms or disease are discovered through the identification of neural and/or other physiological or behavioral correlates of mood, symptoms or disease states, and open- or closed-loop stimulation of OFC, alone or in combination with other brain sites, is used to evaluate the degree to which these biomarkers are valid for an individual patient. In this example, candidate biomarkers are identified on the basis of correlating recorded brain activity or other physiologic measures with mood, symptoms or disease state. This correlation process may involve tracking natural mood, symptom and/or disease states with ambulatory tracking techniques, and/or may involve the external driving of mood or symptom states through customized and controlled environmental interventions, such as virtual or augmented reality tasks, therapist-based interviews, or the like. Resulting candidate biomarkers may involve OFC and/or other brain sites, or other aspects of physiology. In this example, as depicted in FIG. 12, open- or closed-loop stimulation involving OFC that results in alleviation of poor mood, symptom or disease state(s) may inform the validity of candidate biomarkers by testing their correlation with changing values of these states in the context of therapeutic intervention.

Example 8: Open- or Closed-Loop Stimulation to Effect Change in a Biomarker

Figure 13:
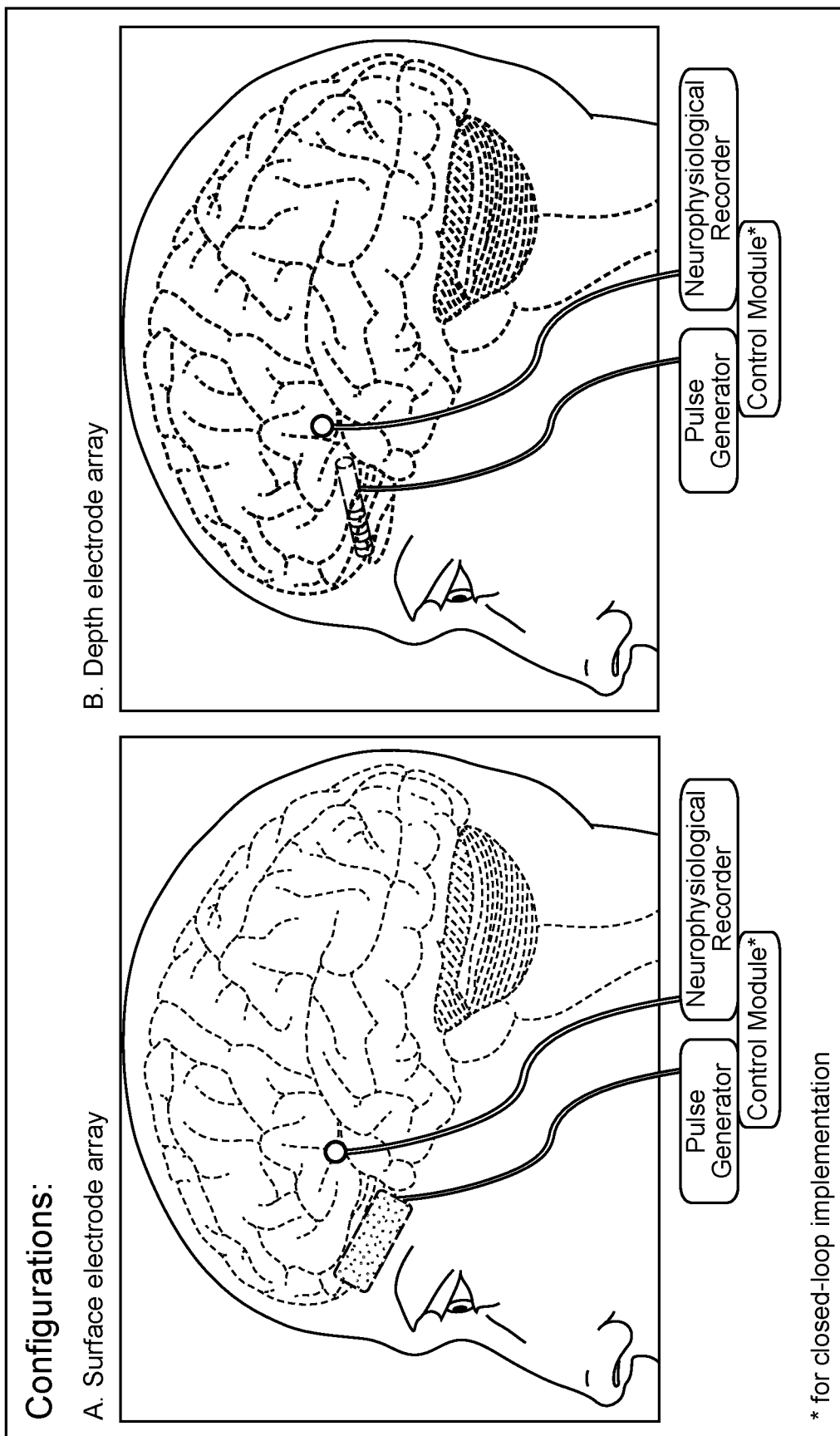
FIG. 13 depicts device configurations and a process for open- or closed-loop OFC stimulation to effect change in a biomarker.

In another example, as depicted in FIG. 13, open- or closed-loop stimulation involving OFC, alone or in combination with other brain sites, is used to target a biomarker of mood, symptom and/or disease state with the goal of diminishing or eliminating the presence of the biomarker and its associated symptom or disease state. In this example, a validated biomarker, which may be neural, physiological, and/or behavioral, could in turn be used to measure the effectiveness of a given set of stimulation parameters.

In a related example, closed-loop stimulation involving OFC, alone or in combination with other brain sites, is used such that a neurophysiologic biomarker is itself a control signal for modulating the parameters of closed-loop stimulation. Likewise, a validated biomarker could in turn be used to measure the effectiveness of a given closed-loop control algorithm that is based in whole or in part on that biomarker.

In either case above, OFC stimulation aimed at modulating a validated biomarker could be used in a prodromal or pre-symptomatic state to prevent the onset of symptoms and/or major disease in patients experiencing remission or those who are otherwise at high risk for disease onset.

Figure 14:
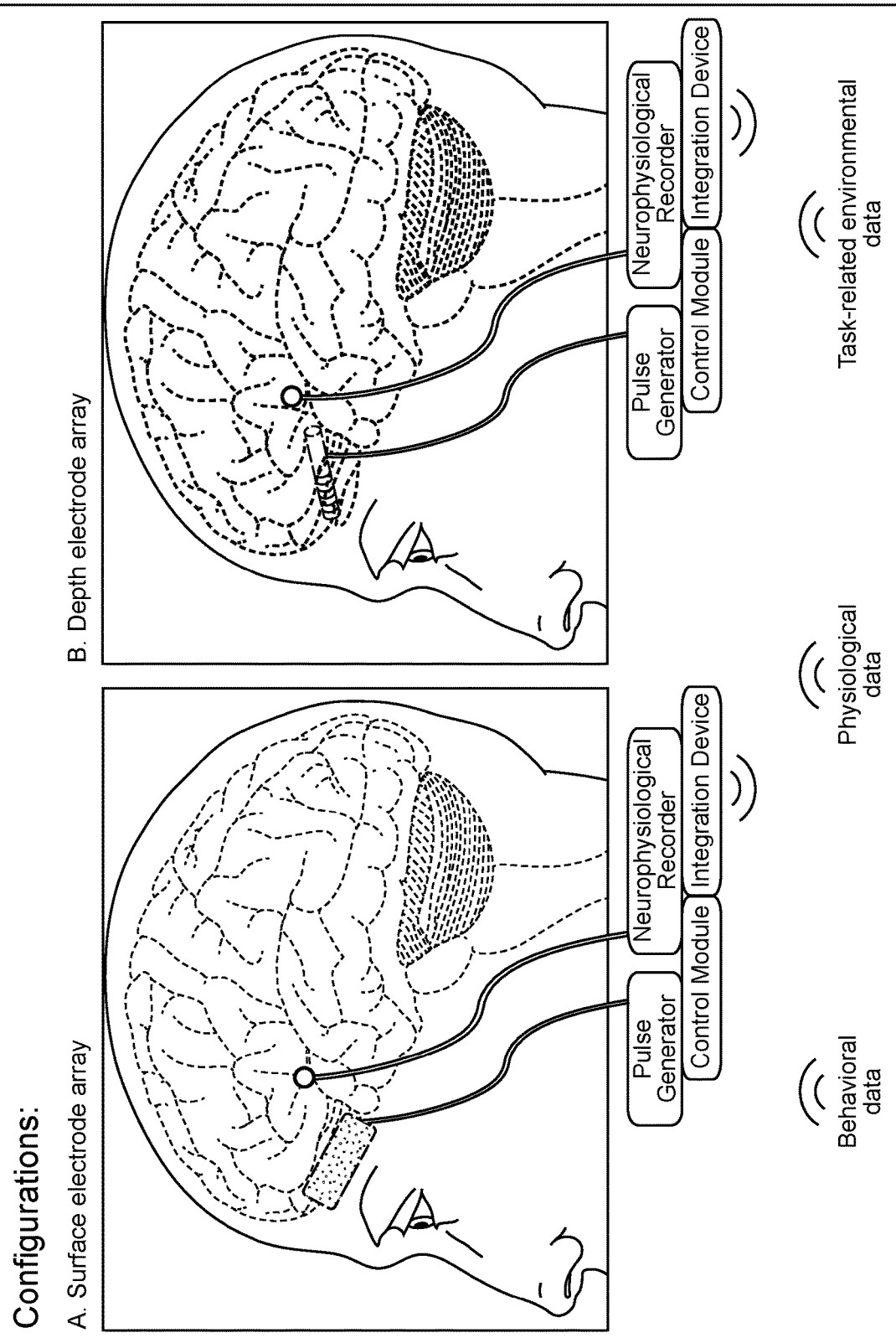
FIG. 14 depicts device configurations and a process for open- or closed-loop OFC stimulation incorporating a wireless or other device to integrate behavioral or physiological sensing, or signals from the environment, into the stimulation regime.

Example 9: Open- or Closed-Loop Stimulation Device to Incorporate Behavioral or Physiological Sensing, or Signals from the Environment In another example, depicted in FIG. 14, additional signals are incorporated into the control matrix for open- or closed-loop stimulation involving OFC, alone or in combination with other brain regions. In the case of open-loop stimulation, this signal communication and incorporation process may involve a wireless device that automatically modulates stimulation parameters based on signal input. In the case of closed-loop stimulation, this signal communication and incorporation may involve a wireless device that automatically adjusts the closed-loop control algorithm. In either case, incorporation of behavioral, physiologic or environmental sensing may be used to optimize the therapeutic benefit of open- and closed-loop stimulation regimes in a way that is responsive to dynamic real-life conditions.

Example 10: OFC Stimulation to Inform Disease Assessment or Diagnosis

Figure 15:
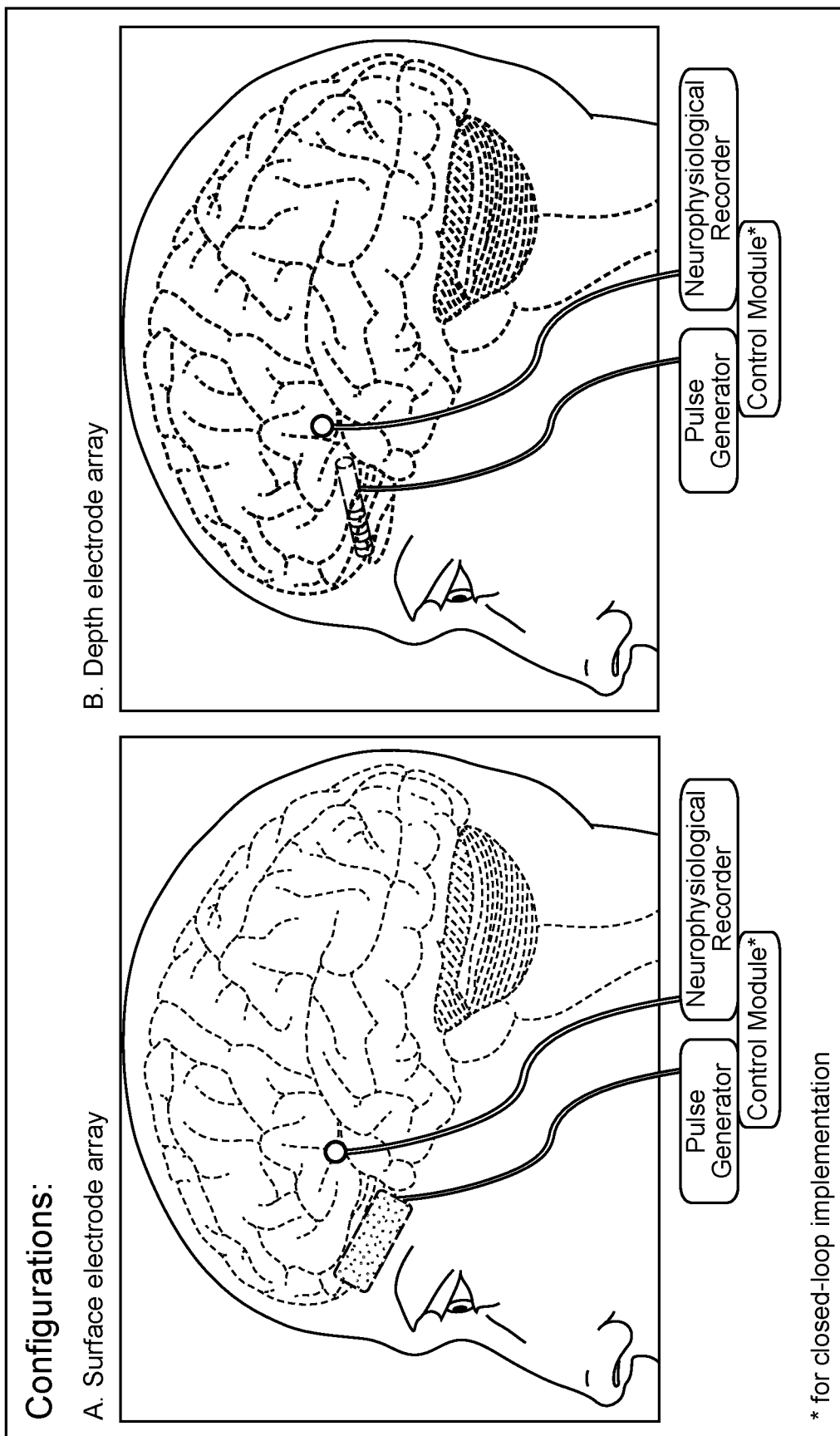
FIG. 15 depicts device configurations and a process for open- or closed-loop OFC stimulation to inform disease assessment or diagnosis, or to enable clinical prognosis or assessment of disease risk.

In another example, depicted in FIG. 15, stimulation is delivered to the OFC to enable or inform clinical assessment or diagnosis of neuropsychiatric disorders. In this example, OFC stimulation, alone or in combination with stimulation in other brain regions, and using open- and/or closed-loop approaches as described above, is used to illuminate the basis or characteristics of the disease state in an individual patient. OFC stimulation may provide such information on the basis of observed effects of stimulation, potentially with a range of parameters and/or in different site configurations. Informative assessment or diagnostic information in this example may include effects of stimulation on clinical or behavioral measures and/or effects of stimulation on the behavior, activity, and/or function of disease-relevant circuitry as determined through neurophysiological recordings, functional brain imaging, or related methods. The clinical evaluation and therapeutic system described above could be adapted for use in this example.

Example 11: OFC Stimulation to Enable Clinical Prognosis or Assessment of Disease Risk In another example, also depicted in FIG. 15, stimulation is delivered to the OFC to enable clinical prognosis or disease risk assessment. In this example, OFC stimulation, alone or in combination with stimulation in other brain regions, and using open- and/or closed-loop approaches as described above, is used to provide information that will provide insight into an individual patient's clinical prognosis and/or disease risk as it relates to one or more neuropsychiatric disorders. OFC stimulation may provide such information on the basis of observed effects of stimulation, potentially with a range of parameters and/or in different site configurations. Informative prognostic and/or risk assessment in this example may include effects of stimulation on clinical or behavioral measures and/or effects of stimulation on the behavior, activity, and/or function of disease-relevant circuitry as determined through neurophysiological recordings, functional brain imaging, or related methods. The clinical evaluation and therapeutic system described above could be adapted for use in this example.

Example 12: Stimulation Across 6 Distinct Brain Regions

In these studies, epilepsy patients were consented for participation in clinical research studies examining the effect of brain stimulation on mood and affect. Prior to the stimulation studies, these patients had undergone intracranial electrode placement to facilitate seizure monitoring and functional mapping in advance of resective epilepsy surgery.

In a first series of studies, stimulation was performed over a wide range of sites across the mesolimbic system, including OFC, dorsal and ventral anterior cingulate cortex (dACC, vACC), insula, amygdala, and hippocampus. Five neurosurgical patients participated. Findings are summarized in FIG. 21. Over a total of 335 stimulation trials testing a range of stimulation parameters across 6 distinct brain regions thought to play a role in mood and affect, no mood changes were reported with the exception of one stimulation trial in which mild anxiety was reported.

Example 13: Longer Duration Stimulation and Standardized Assessment

In a second series of studies, stimulation was performed for longer duration and included sham-stimulation blocks. Nine neurosurgical epilepsy patients participated. All patients completed standardized assessments for trait depression and anxiety (Beck Depression and Anxiety Inventories, BDI and BAI) at least several days prior to the stimulation studies. Controlled stimulation studies were structured so as to incorporate sham blocks (no stimulation) and experimental blocks (continuous stimulation at individual mesolimbic sites) of 10-minute duration each. Stimulation was bipolar and except where noted performed at 100 Hz. Patients were blind to stimulation conditions. During each sham and experimental stimulation block, patients completed a questionnaire quantifying subjective mood (e.g., Immediate Mood Scalar, IMS) and also verbally responded to open-ended questions eliciting their self-reported mood state.

FIG. 22 summarizes the effect of stimulation at various sites on self-reported mood in the second study. Six of the nine patients reported an improvement in mood compared to sham conditions upon stimulation of OFC. Notably, stimulation of no other brain sites, including ventral or dorsal anterior cingulate, posterior cingulate, amygdala or hippocampus, elicited improvements in mood, nor did any sham stimulations. Patients reporting mood improvement are here designated "responders," while those reporting no mood improvement are designated "non-responders." Lateral OFC corresponds to BA10, BA11, and BA47. Medial OFC corresponds to BA11.

FIG. 23 summarizes the mood report findings for the nine patients. All responders reported symptoms of anxiety and/or depression at the start of the study and during the initial sham stimulation block. In these cases, moods subsequently improved specifically upon OFC stimulation. Notably, OFC stimulation appeared to restore a normal mood state, as no indications of mania or unusual behavior appeared. In the case of the responder EC105, an escalating series of stimulation currents was tested and resulted in increasingly improved mood, suggesting a possible dose-dependency of mood effect on stimulation current.

Notably, in contrast to the responders, all three non-responders reported feeling calm and/or happy, or indicated positive mood scores on the IMS, at the beginning of the experiment and throughout the sham and stimulation blocks.

Figure 16:
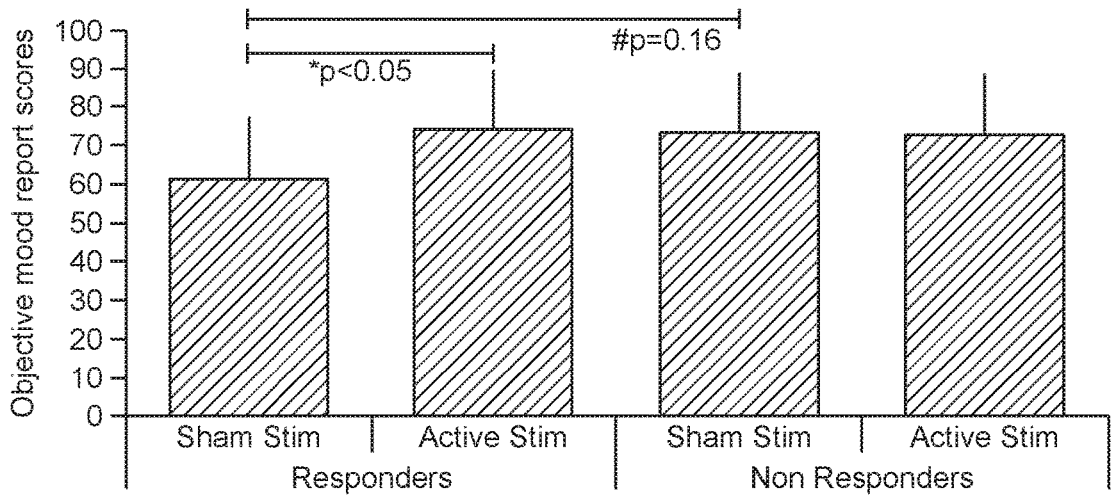
FIG. 16 depicts a comparison of quantified mood conditions in responders and non-responders participating in a clinical study. Responders show a statistically significant increase in normalized mood score (improved mood) during OFC stimulation compared to sham stimulation. No such increase is seen in non-responders. Comparison of mean normalized quantiative mood report scores, showing that responders tend to have lower scores (more negative mood qualities) than do non-responders during sham conditions. Note that these measures reflect quantitative mood scores that are distinct from subjects' verbal self-reports of mood (c.f.

FIG. 16 shows a comparison of quantified mood conditions in responders vs. non-responders. Consistent with the absence of observed mania or hyper-arousal, mean self-reported mood scores among responders increased to a level comparable to that reported by the non-responders throughout the experiment, suggesting a normalizing effect of OFC stimulation on mood.

Figure 17:
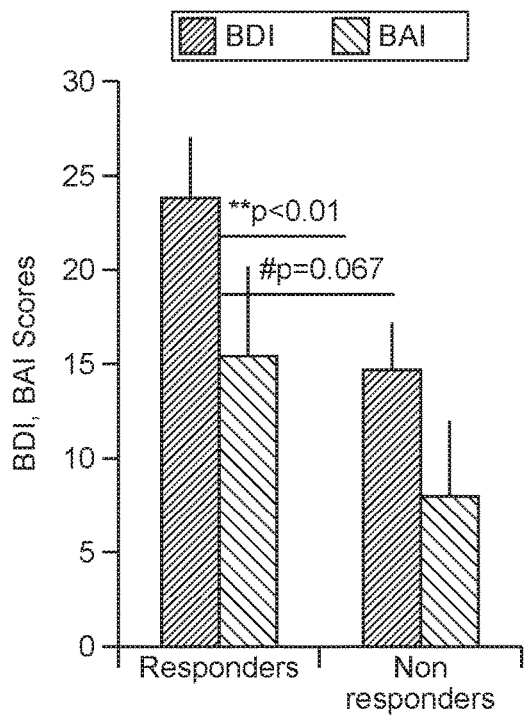
FIG. 17 depicts a comparison of BDI and BAI scores in responders and non-responders participating in a clinical study. Responders have higher baseline trait Depression and Anxiety scores.

Response to LOFC stimulation appears to relate to trait characteristics as well as state characteristics. FIG. 17 shows a comparison of BDI and BAI scores among responders and non-responders, illustrating that as a group responders exhibit significantly higher (worse) BDI scores compared to non-responders; a similar trend is seen for BAI scores in these two groups.

Figure 18:
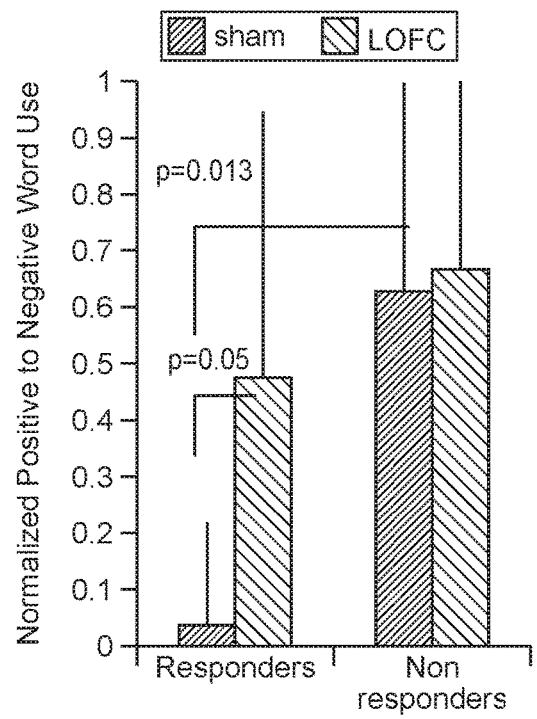
FIG. 18 depicts a comparison of positive word usage during sham and lateral OFC (LOFC) stimulation in responders and non-responders participating in a clinical study. Responders use fewer positive words relative to negative words under sham conditions, and significantly increase their use of positive words with LOFC stimulation. Data is shown here as normalized ratio of positive word use to negative word use, (scale of −1 (all negative words used) to +1 (all positive words used), (i.e. (positive percentage minus negative percentage)/(positive percentage plus negative percentage)). Percentages are from total words spoken for each patient for each stimulation condition.

FIG. 18 shows a comparison of word usage during the subjective self-report as an indication of mood and/or affect during the sham and OFC stimulation blocks. Consistent with the narrative and quantified self-reports of mood state, the normalized proportion of positive words used during the first sham stimulation block was significantly lower among responders than non-responders. Likewise, the proportion of positive words used by responders significantly increased upon OFC stimulation, while it remained nearly unchanged among non-responders.

FIGS. 19 and 20 show sites of bipolar stimulation in responders and non-responders, respectively. The electrodes were positioned in BA10, BA11, and/or BA47. As seen in FIG. 16, a range of stimulation sites within the OFC are effective, indicating no clear anatomical specificity for the effect within this region. Instances of response with OFC were observed with both left- and right-hemisphere stimulation. A similar range of OFC sites elicited no effect in non-responders.

Example 14: Biomarkers Responsive to Treatment

Several biomarkers of mood were been identified. These biomarkers correspond to signals from the OFC, as well as other locations, such as amygdala, hippocampus, cingulate, frontal pole, and lateral frontal lobe. These markers may be used as control signals for closed loop operation. These biomarkers provide direct, real-time physiological correlation between electrical signals (e.g., field potential recordings of neural activity) and mood state of a patient. Electrical signals from one or more of OFC, amygdala, hippocampus, cingulate, frontal pole, and lateral frontal lobe include features that correlate with an individual's mood in real time. Furthermore, these electrical signals are modulated by the OFC stimulation, as disclosed herein. In other words, these signals provide feedback control as these signals are modulated by OFC stimulation. Thus, these signals can be used in a closed loop system to monitor effectiveness of OFC stimulation and if needed, modulate the treatment. The features in the electrical signals (e.g., field potential) recordings relate to the overall power, power in specific frequency ranges (e.g. Alpha, delta, beta, gamma, and/or high gamma) in specific brain locations listed above, and/or coherence patterns between signals recorded in those locations.

Example 15: Mood Effects of OFC Stimulation

A modular experimental design (FIG. 24A, B) and extensive electrode coverage in all subjects (FIG. 24C) allowed us to assess the mood effects of stimulation in numerous brain regions, including limbic and paralimbic structures previously implicated in mood regulation.

Figure 25C:
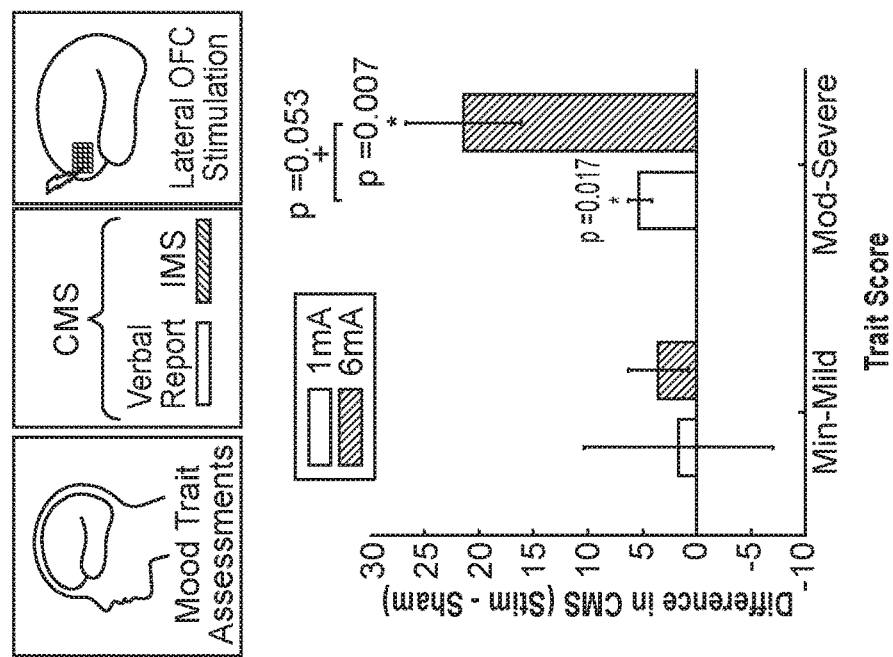
FIGS. 25A-25C show that OFC stimulation produces dose-dependent mood improvement in subjects with moderate-severe baseline mood trait.
Figure 25B:
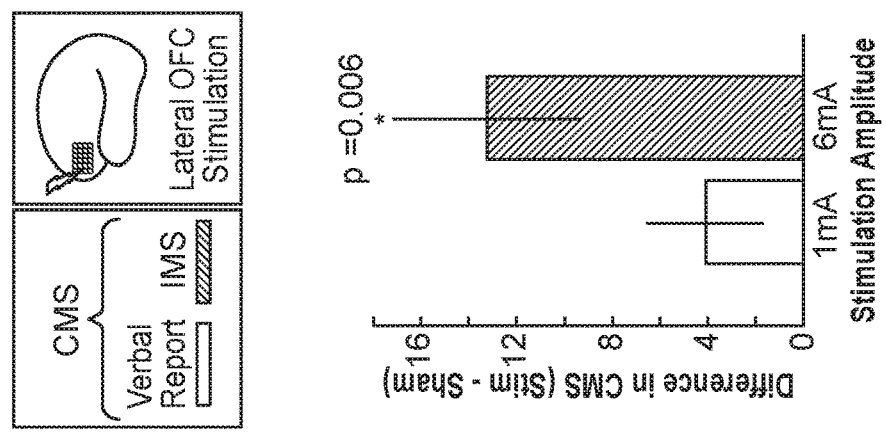
Figure 25A:
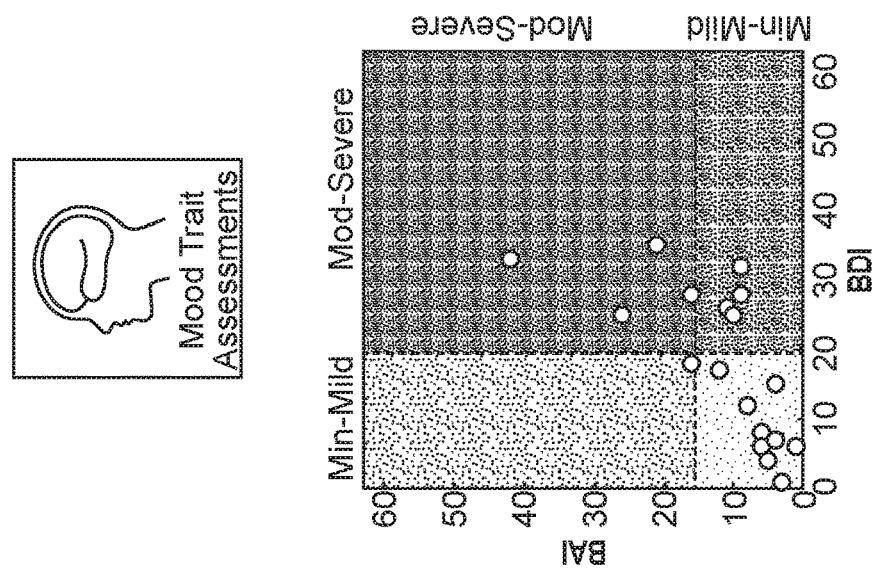

Subjects had baseline depression and anxiety traits that ranged from mild to severe (FIG. 25A). Over a wide range of stimulation parameters (0.2-100 Hz, pulse width 100-1000 µs, 1-10 mA, duration 1-200 s), subjects generally did not report acute stimulation-induced changes in mood state, though stimulation of amygdala occasionally evoked dysphoria or other unpleasant symptoms, as previously described (J. R. Smith et. al., Epilepsy Behav 8, 534-541 (2006); L. Mazzola, et al., J Clin Neurophysiol 34, 307-314 (2017)). By contrast, during OFC stimulation (100 Hz, 100 µs pulse width, 1 or 6 mA, duration 100-200 sec; hereafter referred to as 'continuous' stimulation), subjects' verbal reports often reflected marked mood improvement (Table S2). For example, one subject (EC87) used mostly negative words to describe their mood state during sham (0 mA) stimulation ("nervous," "scared," "apprehensive"), but, during OFC stimulation (6 mA), used mostly positive words ("calm," "positive," "relaxed"). Composite mood scores (CMS) reflected such changes, increasing relative to baseline levels recorded during sham stimulation. Across subjects, we observed increased CMS (see Methods) with higher current stimulation (FIG. 2B; 1 mA, $t(5)=1.66$, $p=0.158$; 6 mA, $t(12)=3.33$, $p=0.006$), indicating dose-dependent improvement in mood state. This group effect was driven by subjects with moderate or severe baseline mood trait (FIG. 2C; t-tests indicating increase in CMS compared to sham only significant for subjects in the moderate-severe group: 1 mA, $t(3)=4.82$, $p=0.017$; 6 mA, $t(6)=4.02$, $p=0.007$; two-sample t-test between stimulation amplitudes trend-level significant for only the moderate-severe group $t(9)=-2.23$, $p=0.053$). Subjects with minimal or mild baseline mood trait did not show significant mood improvement. This finding is consistent with previous work on TRD showing that patient-specific factors, including measures of disease severity, predict response to brain stimulation (A. L. Crowell et al., *Front Integr Neurosci* 9, 41 (2015)).

FIG. 24. Experimental design and locations of stimulated sites. (A) Experimental timeline: Subjects completed the Beck Anxiety Index (BAI) and Beck Depression Index II (BDI) to assay trait anxiety and depression prior to electrode implantation for seizure monitoring. Mood was assessed during continuous intracranial electroencephalography (iEEG) using the Immediate Mood Scaler (IMS). Stimulation studies were conducted, and electrodes were then explanted. (B) Overview of stimulation experiments. iEEG was continuously recorded while stimulation was delivered at different sites. At each stimulation site, verbal report and IMS score were combined to provide a Composite Mood Score (CMS). Stimulation was delivered in charge-balanced biphasic pulses of 100 μS pulse width, 100 Hz frequency, and amplitudes of 1 or 6 mA. (C) MNI template brain with all recording electrodes across study subjects. Colored markers indicate electrodes which were verified to be in target regions based on review of co-registered CT and MRI, while gray markers indicate non-target region electrodes. Cingulate, orbitofrontal cortex (OFC), insula, amygdala, and hippocampus.

FIG. 25. OFC stimulation produces dose-dependent mood improvement in subjects with moderate-severe baseline mood trait. (A) Subjects ranged from exhibiting minimal or mild (Min-Mild) to moderate (Mod-Severe) trait anxiety and depression. Subjects exhibited Min-Mild scores on both the BAI and BDI, or Min-Mild on one scale and Mod-Severe on the other, or Mod-Severe scores on both scales. (B) CMS changed with OFC 6 mA stimulation relative to sham. (C) The mood-improving effects of OFC stimulation were specific to subjects with Mod-Severe trait anxiety and depression. T-tests showed that changes in CMS in the mod-severe trait group drove the significant differences between sham and *verum* stimulation (p-values shown in graph).

Example 16: Specificity of Mood Effects

Stimulation of other limbic and paralimbic regions generally did not result in such robust mood improvement. However, in line with previous studies (H. S. Mayberg, et al., *Neuron* 45, 651-660 (2005); K. S. Choi, et al., *JAMA Neurol* 72, 1252-1260 (2015)), cingulate cortex stimulation did improve mood state, though variability was greater than for OFC stimulation. Stimulation of lateral OFC was more effective for mood improvement than medial OFC, likely due to distinct functions of these subregions (P. Fettes, et al., *Front Syst Neurosci* 11, 25 (2017); P. H. Rudebeck, et al., Ann N Y Acad Sci 1239, 1-13 (2011)). Speech rate during verbal report was not affected by OFC stimulation, indicating that the intervention did not produce symptoms of hypomania or other supraphysiological mood states, as has been observed with DBS of other brain regions (S. Kohl, et al., BMC Psychiatry 14, 214 (2014); K. W. Scangos, K. Shahlaie, Biol Psychiatry 82, e39-e41 (2017)). Furthermore, OFC stimulation generally did not affect CMS of individuals who did not report low mood symptoms during the baseline sham period, suggesting that OFC stimulation normalizes mood state and does not produce non-specific mood elevation.

Example 17: White Matter Connectivity of OFC

The ability of DBS to alleviate mood symptoms is thought to depend on large-scale brain networks whose activity is modulated by stimulation at the target site (B. W. Dunlop, et al. Am J Psychiatry, appiajp201616050518 (2017); H. Johansen-Berg, et al., Cereb Cortex 18, 1374-1383 (2008)). OFC is comprised of multiple functionally distinct subregions with medial-lateral and anterior-posterior organization (M. L. Kringelbach, et al., *Prog Neurobiol* 72, 341-372 (2004), P. H. Rudebeck, E. A. Murray. *Neuron* 84, 1143-1156 (2014); P. H. Rudebeck et al., 2011 (supra)). These subregions connect variably to other prefrontal cortices, ventral striatum, and limbic structures (P. Fettes, et al. (supra). Using residual bootstrap probabilistic diffusion tractography (J. I. Berman et al., *Neuroimage* 39, 215-222 (2008)), we found that sites stimulated within OFC in our study are in proximity to frontal cortico-cortical fibers, frontostriatal fibers, and fibers connecting OFC with mesial temporal structures (uncinate fasciculus). Thus, OFC has a pattern of connectivity to cortical and subcortical regions (A. T. Drysdale, et al., *Nat Med* 23, 28-38 (2017)) that may be critical for mediating the mood-improving effect of OFC stimulation (P. Riva-Posse et al. Mol Psychiatry, (2017); P. Riva-Posse, et al., Biol Psychiatry 76, 963-969 (2014)).

Example 18: Neural Activity During Spontaneous Mood Fluctuation

To further understand how OFC stimulation might have this effect, we asked how changes in mood state are reflected in neurophysiology, especially in OFC. Subjects serially reported their mood state using the IMS at variable intervals in the days prior to stimulation studies (FIG. 24A; mean total number of IMS timepoints per subject±SD=12.48±11.21; mean number of IMS timepoints per day+SD=2.16±2.12) In most subjects, IMS scores showed considerable variation during this time, which facilitated regression analysis with features of neural activity. We extracted segments of iEEG activity surrounding each IMS timepoint and examined first-order neural features during this natural (spontaneous) fluctuation in mood (FIG. 26A). Normalized OFC power negatively correlated with IMS in theta and alpha frequency bands but not in higher frequencies; this frequency-specific inverse relationship between mood state and OFC power was seen only in subjects with moderate-severe baseline mood traits (FIG. 26B, C). Of note, individual mean IMS scores did not differ significantly between subjects with minimal-mild and moderate-severe mood traits, so the neurophysiological differences between these groups cannot be explained by distinct distributions of mood scores.

Number of IMS timepoints used in correlations for each subject:

| | |
|---|---|
| EC81 | 3 |
| EC82 | 16 |
| EC84 | 16 |
| EC87 | 12 |
| EC91 | 2 |
| EC92 | 3 |
| EC96 | 2 |
| EC99 | 3 |
| EC108 | 12 |
| EC113 | 5 |
| EC122 | 13 |
| EC125 | 12 |
| EC129 | 8 |
| EC133 | 6 |
| EC137 | 18 |
| EC139 | 3 |
| EC150 | 20 |
| EC152 | 7 |
| EC153 | 3 |

FIG. 26. OFC low frequency power negatively correlates with natural mood fluctuation in subjects with moderate-severe baseline mood trait. (A) Four minutes of iEEG were extracted surrounding each IMS timepoint. Time-averaged log power in OFC was calculated on each iEEG segment and correlated with IMS. (B) Across all IMS points in subjects with min-mild anxiety/depression, there were no significant correlations between IMS and OFC power. (C) In patients with mod-severe anxiety/depression, theta and alpha OFC powers exhibited negative correlations with IMS.

Example 19: Neural Activity in OFC During Stimulation

Having observed that OFC low frequency power and mood state vary inversely during natural mood fluctuations, we hypothesized that mood improvement would be associated with decreased low frequency power during OFC stimulation. To test this, we developed an approach to analyze OFC activity during stimulation. Neural responses during electrical stimulation are typically hampered by stimulus-related artifact that can obscure much or all of the underlying signal (L. F. Heffer, et al., J Neurosci Methods 170, 277-284 (2008); U. Hoffmann, et al. Conf Proc IEEE Eng Med Biol Soc 2011, 7159-7162 (2011); Y. Sun, et al., J Neurosci Methods 237, 33-40 (2014)). Therefore, we developed artifact rejection techniques (Methods) that enabled evaluation of low frequency neural activity during stimulation. Spectral analysis revealed that OFC stimulation suppresses low frequency power (FIG. 27A). This suppression was significant for theta range frequencies ($p=0.03$) but not for alpha ($p=0.18$; FIG. 27B) or beta frequencies ($p=0.56$). Power in only the theta frequency range increased at trend-level after offset of stimulation ($p=0.07$; FIG. 27B). Thus, local neurophysiological changes during OFC stimulation mirror changes in this region seen during spontaneous mood fluctuation, suggesting that the mood effects of OFC stimulation may involve circuits that mediate natural mood variation. However, Pearson correlation analysis revealed that percent change in CMS is not significantly correlated to percent change in power from pre-stim to stim: $r(6)=0.500$, $p=0.212$, so OFC power alone does not provide a direct readout of mood state.

FIG. 27. Local neurophysiological effects of OFC stimulation. (A) Low-frequency power is suppressed during OFC stimulation. Individual subject (EC125) example shown for 1 mA (left) and 6 mA (right) stimulation. Stimulation onset (black line) and offset (red line). (B) Percent change in OFC power was calculated from pre-stim to stim (left) and stim to post-stim (right). OFC theta power decreased from pre-stim to stim ($p=0.03$) and trend-level increase from stim to post-stim ($p=0.07$), while alpha and beta powers were not significantly changed (alpha, $p=0.18$ and $p=0.22$; beta, $p=0.56$ and $p=0.94$). (C) Single-pulse stimulation (SPS) in OFC before and after OFC continuous stimulation to assess changes in local excitability. (D) OFC SPS before (green) and after (magenta) OFC continuous stimulation in a representative subject (EC153) showing that evoked potentials increase after continuous stimulation. (E) Across 4 subjects, peak amplitude of evoked potentials increased after continuous stimulation. Each circle represents evoked potential from an individual pulse of SPS.

Example 20: Single-Pulse Stimulation in OFC

A complementary approach to characterizing the neurophysiological effects of OFC stimulation involves analyzing neural activity immediately before and after stimulation (E. Formaggio, et al., Front Neuroeng 6, 1 (2013)), though this necessarily assumes that stimulation-induced effects outlast the stimulus itself. Trains of high-amplitude single pulses (see Methods) applied to OFC before OFC continuous stimulation evoked local responses within 100 ms of pulse onset (FIG. 27C). After OFC continuous stimulation, identical trains of single pulses evoked potentiated responses (FIG. 27C, D, E) reflecting increased cortical excitability, as has been described following high-frequency repetitive transcranial magnetic stimulation (D. Veniero, et al., J Neurophysiol 104, 1578-1588 (2010)). Continuous stimulation of a site remote to OFC (precentral gyms) did not potentiate single pulse-evoked responses in OFC, indicating that the effect is specific to OFC stimulation. Of note, abnormal single-pulse responses have been reported as a marker of epileptogenic cortex (A. Valentin, et al., Neurology 65, 426-435 (2005); A. Valentin, et al. Lancet Neurol 4, 718-726 (2005)), but none of our subjects had seizures arising from OFC.

Example 21: Network Effects of OFC Stimulation

Figure 28A:
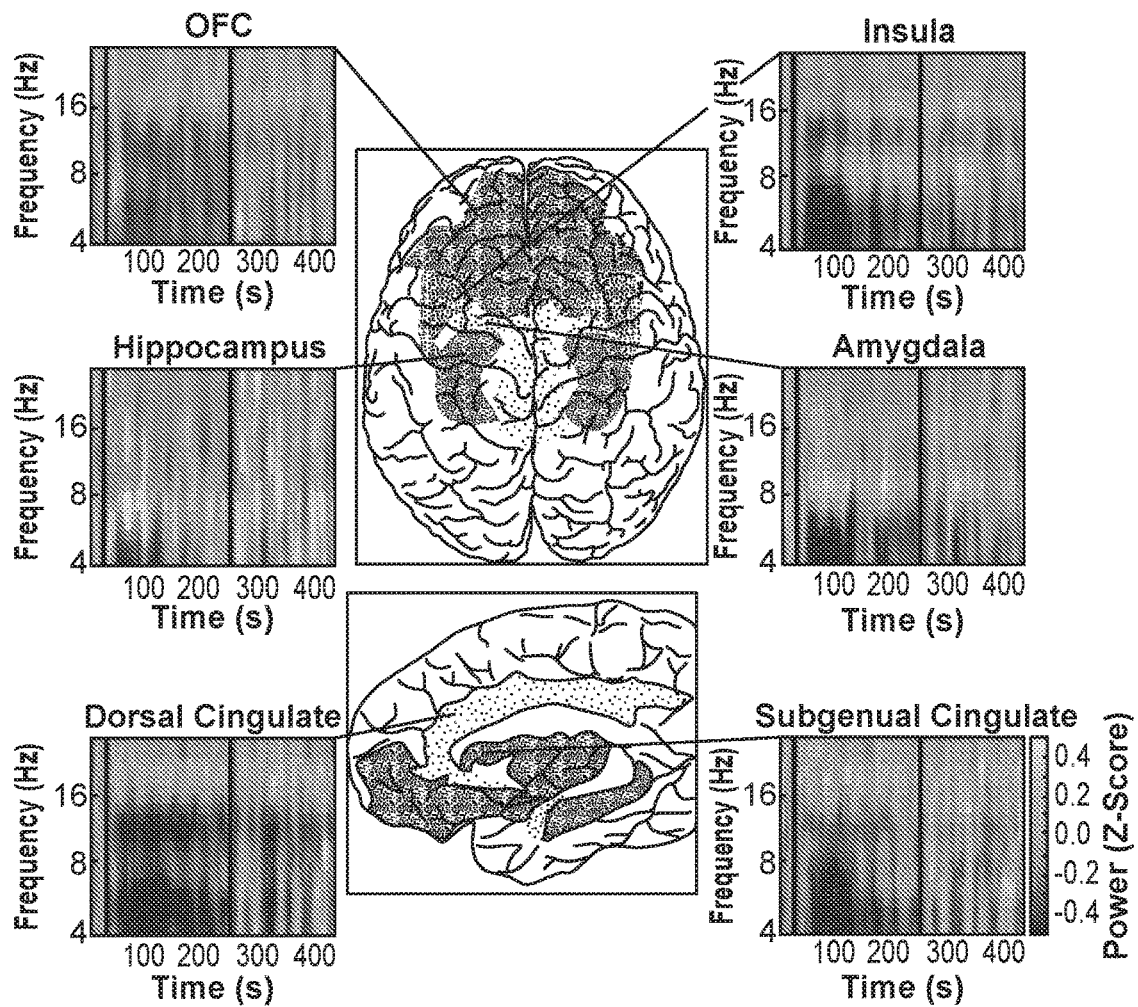
FIGS. 28A-28B illustrate network-level neurophysiological effects of OFC stimulation.
Figure 28B:
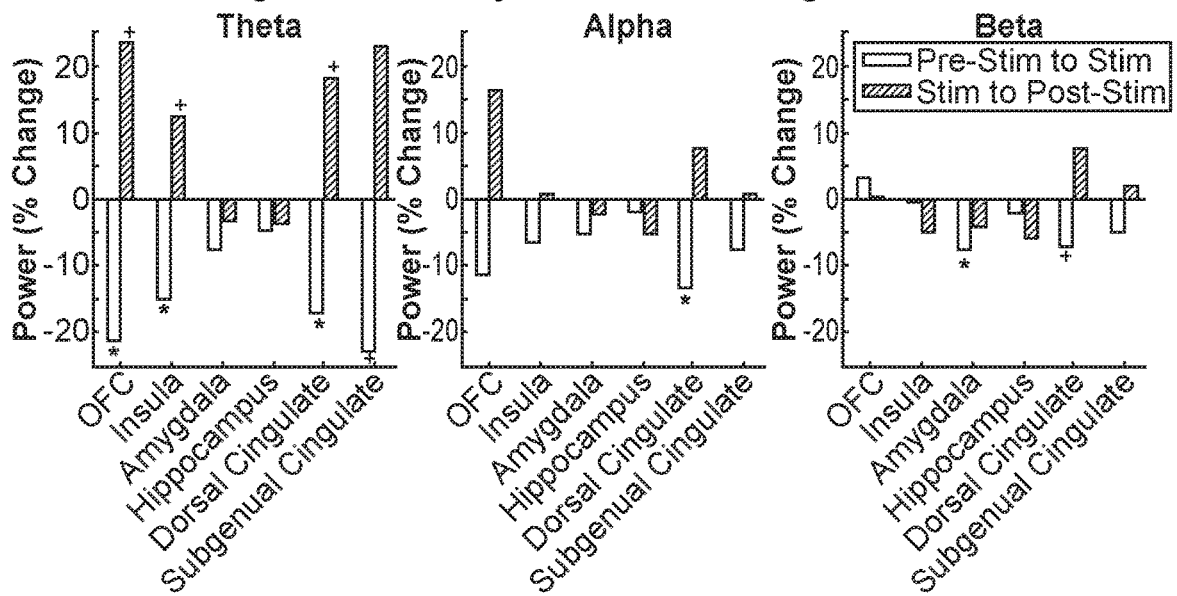

Affective states arise from a distributed network of brain regions (S. A. Guillory, et al., Soc Cogn Affect Neurosci 9, 1880-1889 (2014)), and, given the effects of OFC stimulation on local cortical excitability, we next examined effects on activity in other sites sampled by intracranial electrodes (FIG. 28A). Spectral analysis revealed that OFC stimulation suppressed low frequency power broadly across insula, dorsal cingulate, and subgenual cingulate, with greatest effects seen in the theta frequency band in OFC, insula, and cingulate cortices (FIG. 28B). Statistically significant decreases in beta range frequencies were also seen in amygdala and at trend-level in dorsal cingulate during OFC stimulation (FIG. 28B). Following offset of stimulation, low frequency power showed increases that were generally proportional to the initial decrease across all studied regions (FIG. 28B). Although causality cannot be inferred from our data, taken together these findings suggest that mood improvement observed during OFC stimulation may be mediated through a combination of local and network-level changes in neural activity.

Power, Pre-Stim to Stim:

| Brain Region | Theta | Alpha | Beta |
| --- | --- | --- | --- |
| OFC | $t(9) = -2.61$, $p = 0.028$ | $t(9) = -1.44$, $p = 0.183$ | $t(9) = 0.61$, $p = 0.560$ |
| Insula | $t(10) = -2.30$, $p = 0.044$ | $t(10) = -1.30$, $p = 0.224$ | $t(10) = -0.03$, $p = 0.980$ |
| Amygdala | $t(8) = -1.19$, $p = 0.268$ | $t(8) = -0.89$, $p = 0.401$ | $t(8) = -3.58$, $p = 0.007$ |
| Hippocampus | $t(11) = -0.90$, $p = 0.390$ | $t(11) = -0.32$, $p = 0.758$ | $t(11) = -0.54$, $p = 0.598$ |
| Dorsal Cingulate | $t(10) = -3.06$, $p = 0.012$ | $t(10) = -2.64$, $p = 0.025$ | $t(10) = -1.95$, $p = 0.079$ |
| Subgenual Cingulate | $t(3) = -2.44$, $p = 0.092$ | $t(3) = -0.96$, $p = 0.409$ | $t(3) = -1.57$, $p = 0.216$ |

Power, Stim to Post-Stim:

| Brain Region | Theta | Alpha | Beta |
| --- | --- | --- | --- |
| OFC | $t(9) = 2.03$, $p = 0.073$ | $t(9) = 1.31$, $p = 0.223$ | $t(9) = 0.08$, $p = 0.939$ |
| Insula | $t(10) = 1.89$, $p = 0.088$ | $t(10) = 0.25$, $p = 0.805$ | $t(10) = -1.01$, $p = 0.337$ |
| Amygdala | $t(8) = -0.58$, $p = 0.576$ | $t(8) = -0.63$, $p = 0.543$ | $t(8) = -0.87$, $p = 0.410$ |
| Hippocampus | $t(11) = -0.87$, $p = 0.402$ | $t(11) = -1.46$, $p = 0.172$ | $t(11) = -1.61$, $p = 0.135$ |
| Dorsal Cingulate | $t(10) = 2.06$, $p = 0.066$ | $t(10) = 1.49$, $p = 0.168$ | $t(10) = 0.90$, $p = 0.391$ |
| Subgenual Cingulate | $t(3) = 1.66$, $p = 0.196$ | $t(3) = 0.05$, $p = 0.962$ | $t(3) = 0.74$, $p = 0.514$ |

FIG. 28. Network-level neurophysiological effects of OFC stimulation. (A) Spectrograms from one subject show suppression of low-frequency power in several mood-relevant brain regions sampled by intracranial electrodes. (B) Across all subjects, most significant changes in power from pre-stim to stim (white bars) and stim to post-stim (black bars) were in the theta frequency band.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. our data, taken together these findings suggest that mood improvement observed during OFC stimulation may be mediated through a combination of local and network-level changes in neural activity.

Power, Pre-Stim to Stim:

| Brain Region | Theta | Alpha | Beta |
| --- | --- | --- | --- |
| OFC | $t(9) = -2.61$, $p = 0.028$ | $t(9) = -1.44$, $p = 0.183$ | $t(9) = 0.61$, $p = 0.560$ |
| Insula | $t(10) = -2.30$, $p = 0.044$ | $t(10) = -1.30$, $p = 0.224$ | $t(10) = -0.03$, $p = 0.980$ |
| Amygdala | $t(8) = -1.19$, $p = 0.268$ | $t(8) = -0.89$, $p = 0.401$ | $t(8) = -3.58$, $p = 0.007$ |
| Hippocampus | $t(11) = -0.90$, $p = 0.390$ | $t(11) = -0.32$, $p = 0.758$ | $t(11) = -0.54$, $p = 0.598$ |
| Dorsal Cingulate | $t(10) = -3.06$, $p = 0.012$ | $t(10) = -2.64$, $p = 0.025$ | $t(10) = -1.95$, $p = 0.079$ |
| Subgenual Cingulate | $t(3) = -2.44$, $p = 0.092$ | $t(3) = -0.96$, $p = 0.409$ | $t(3) = -1.57$, $p = 0.216$ |

Power, Stim to Post-Stim:

| Brain Region | Theta | Alpha | Beta |
| --- | --- | --- | --- |
| OFC | $t(9) = 2.03$, $p = 0.073$ | $t(9) = 1.31$, $p = 0.223$ | $t(9) = 0.08$, $p = 0.939$ |
| Insula | $t(10) = 1.89$, $p = 0.088$ | $t(10) = 0.25$, $p = 0.805$ | $t(10) = -1.01$, $p = 0.337$ |
| Amygdala | $t(8) = -0.58$, $p = 0.576$ | $t(8) = -0.63$, $p = 0.543$ | $t(8) = -0.87$, $p = 0.410$ |
| Hippocampus | $t(11) = -0.87$, $p = 0.402$ | $t(11) = -1.46$, $p = 0.172$ | $t(11) = -1.61$, $p = 0.135$ |
| Dorsal Cingulate | $t(10) = 2.06$, $p = 0.066$ | $t(10) = 1.49$, $p = 0.168$ | $t(10) = 0.90$, $p = 0.391$ |
| Subgenual Cingulate | $t(3) = 1.66$, $p = 0.196$ | $t(3) = 0.05$, $p = 0.962$ | $t(3) = 0.74$, $p = 0.514$ |

FIG. 28. Network-level neurophysiological effects of OFC stimulation. (A) Spectrograms from one subject show suppression of low-frequency power in several mood-relevant brain regions sampled by intracranial electrodes. (B) Across all subjects, most significant changes in power from pre-stim to stim (white bars) and stim to post-stim (black bars) were in the theta frequency band.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for treating a neuropsychiatric disorder in a subject, the method comprising:
    positioning one or more electrodes at Brodmann Area 11, Brodmann Area 47, or a combination thereof of orbitofrontal cortex region of brain of the subject; and
    applying electrical stimulation only to Brodmann Area 11, Brodmann Area 47, or a combination thereof via the one or more electrodes in a manner effective to treat the neuropsychiatric disorder in the subject.

2. The method of claim 1, wherein the method comprises applying electrical stimulation to Brodmann Area 11.

3. The method of claim 1, wherein the method comprises applying electrical stimulation to Brodmann Area 47.

4. The method of claim 1, wherein the one or more electrodes are placed on a surface of Brodmann Area 11 or Brodmann Area 47.

5. The method of claim 1, wherein the one or more electrodes are placed within Brodmann Area 11 or Brodmann Area 47.

6. The method of claim 1, wherein the one or more electrodes are a non-brain penetrating surface electrode array.

7. The method of claim 1, wherein the one or more electrodes are a brain-penetrating electrode array.

8. The method of claim 1, wherein the neuropsychiatric disorder comprises depression, wherein applying the electrical stimulation treats depression.

9. The method of claim 1, wherein the neuropsychiatric disorder comprises anxiety, wherein applying the electrical stimulation treats anxiety.

10. The method of claim 9, wherein the anxiety is generalized anxiety disorder (GAD) or post-traumatic stress disorder (PTSD).

11. The method of claim 1, wherein the neuropsychiatric disorder is Addiction, Anorexia, Obsessive-Compulsive Disorder (OCD), Bipolar Disorder (BD), or chronic pain.

12. The method of claim 1, wherein the electrical stimulation is applied unilaterally.

13. The method of claim 1, wherein the electrical stimulation is applied bilaterally.

14. The method of claim 1, wherein the electrical stimulation is applied at least two times, wherein the electrical stimulation is spatially and/or temporally different.

15. The method of claim 1, wherein the method further comprises assessing effectiveness of the treatment in the subject.

16. The method of claim 1, wherein the method comprises applying electrical stimulation to Brodmann Area 11 and Brodmann Area 47.

17. The method of claim 1, wherein the neuropsychiatric disorder is chronic-pain-related-distress, wherein the method further comprises measuring chronic-pain-related-distress in the subject by a Visual Analog Scale.

18. A method for ameliorating a symptom of a neuropsychiatric disorder in a subject, the method comprising:
    positioning one or more electrodes at Brodmann Area 11, Brodmann Area 47, or a combination thereof of orbitofrontal cortex region of brain of the subject; and
    applying electrical stimulation only to Brodmann Area 11, Brodmann Area 47, or a combination thereof via the one or more electrodes in a manner effective to ameliorate the symptom of the neuropsychiatric disorder in the subject.

19. The method of claim 18, wherein the symptom comprises depression and wherein applying the electrical stimulation ameliorates depression.

20. The method of claim 19, wherein depression is measured by Beck Depression Inventories (BDI) score and applying the electrical stimulation is effective in reducing the BDI score.

21. The method of claim 18, wherein the symptom comprises anxiety and wherein applying the electrical stimulation ameliorates anxiety.

22. The method of claim 21, wherein the neuropsychiatric disorder is generalized anxiety disorder (GAD) or post-traumatic stress disorder (PTSD).

23. The method of claim 21, wherein anxiety is measured by Beck Anxiety Inventories (BAI) score and applying the electrical stimulation is effective in reducing the BAI score.

24. The method of claim 18, wherein the method comprises applying electrical stimulation to Brodmann Area 11.

25. The method of claim 18, wherein the method comprises applying electrical stimulation to Brodmann Area 47.

26. The method of claim 18, wherein the one or more electrodes are a non-brain penetrating electrode array.

27. The method of claim 18, wherein the one or more electrodes are a brain-penetrating electrode array.

28. The method of claim 18, wherein the neuropsychiatric disorder is addiction, anorexia, Obsessive-Compulsive Disorder (OCD), Bipolar Disorder (BD), or chronic pain.

29. The method of claim 18, wherein the method further comprises assessing effectiveness of the treatment in the subject.

30. The method of claim 18, wherein the method comprises applying electrical stimulation to Brodmann Area 11 and Brodmann Area 47.

\* \* \* \* \*